(12) United States Patent
Asai et al.

(10) Patent No.: US 8,466,290 B2
(45) Date of Patent: Jun. 18, 2013

(54) STAT3 INHIBITOR CONTAINING QUINOLINECARBOXAMIDE DERIVATIVE AS ACTIVE INGREDIENT

(75) Inventors: Akira Asai, Shizuoka (JP); Kenji Matsuno, Shizuoka (JP); Naohisa Ogo, Shizuoka (JP); Takane Yokotagawa, Tokyo (JP); Osamu Takahashi, Tokyo (JP); Yasuto Akiyama, Shizuoka (JP); Tadashi Ashizawa, Shizuoka (JP); Tadashi Okawara, Kumamoto (JP)

(73) Assignees: Pharma IP General Incorporated Association, Mishima-shi (JP); Pharma Design, Inc., Tokyo (JP); Shizuoka Prefecture, Shizuoka (JP); Kumamoto Health Science University, Kumamoto-shi (JP); Kabushiki Kaisha Yakult Honsha, Tokyo (JP)

( * ) Notice: Subject to any disclaimer, the term of this patent is extended or adjusted under 35 U.S.C. 154(b) by 31 days.

(21) Appl. No.: 13/003,441

(22) PCT Filed: Jul. 10, 2009

(86) PCT No.: PCT/JP2009/003235
§ 371 (c)(1),
(2), (4) Date: Mar. 30, 2011

(87) PCT Pub. No.: WO2010/004761
PCT Pub. Date: Jan. 14, 2010

(65) Prior Publication Data
US 2011/0172429 A1    Jul. 14, 2011

(30) Foreign Application Priority Data

Jul. 10, 2008    (JP) .................................. 2008-180433

(51) Int. Cl.
*C07D 215/38*    (2006.01)

(52) U.S. Cl.
USPC ........................................................ 546/159

(58) Field of Classification Search
USPC .......................................... 546/159; 514/312
See application file for complete search history.

(56) References Cited

U.S. PATENT DOCUMENTS

| | | | |
|---|---|---|---|
| 7,034,049 B1 | 4/2006 | Pevarello et al. | |
| 7,049,324 B1 | 5/2006 | Saha et al. | |
| 7,271,179 B2 | 9/2007 | Bemis et al. | |
| 7,279,469 B2 | 10/2007 | Pierce et al. | |
| 7,511,061 B2 | 3/2009 | Saha et al. | |
| 2004/0152730 A1* | 8/2004 | Farina et al. | 514/314 |
| 2005/0182093 A1 | 8/2005 | Farina et al. | |
| 2008/0014189 A1 | 1/2008 | Pierce et al. | |
| 2008/0033000 A1* | 2/2008 | Chang et al. | 514/266.4 |
| 2008/0103150 A1 | 5/2008 | Saha et al. | |
| 2008/0312435 A1 | 12/2008 | Saito et al. | |
| 2009/0054445 A1 | 2/2009 | Albert et al. | |
| 2009/0069301 A1 | 3/2009 | Milburn et al. | |

FOREIGN PATENT DOCUMENTS

| | | |
|---|---|---|
| JP | 2003 507329 | 2/2003 |
| JP | 2003 514804 | 4/2003 |
| JP | 2004 529145 | 9/2004 |
| JP | 2006 513192 | 4/2006 |
| JP | 2006 515313 | 5/2006 |
| WO | 2004 078731 | 9/2004 |
| WO | 2006 051704 | 5/2006 |
| WO | 2006 094237 | 9/2006 |
| WO | 2007 086799 | 8/2007 |
| WO | WO 2008/044667 A1 | 4/2008 |

OTHER PUBLICATIONS

Rizk, Med Chem Res, vol. 14(5), pp. 260-273, 2005.*
Extended Search Report issued Feb. 7, 2012 in European Patent Application No. 09794208.0-2101/2325181.
Rizk, O. H. et al., "Synthesis Of Some New Antimicrobial Thiadiazolyl And Oxadiazolyl Quinoline Derivatives", Medicinal Chemistry Research, vol. 14, No. 5, pp. 260-273, (2005).
Ihle, J. N. et al., "Jaks And Stats In Signaling By The Cytokine Receptor Superfamily", Reviews, TIG, vol. 11, No. 2, pp. 69-74, (Feb. 1995).
Yang, C-H et al., "STAT3 Complements Defects In An Interferon-Resistant Cell Line: Evidence For An Essential Role For STAT3 In Interferon Signaling And Biological Activities", Cell Biology, Proc. Natl. Acad. Sci, vol. 95, pp. 5568-5572, (May 1998).
Darnell, J. E. et al., "Jak-STAT Pathways And Transcriptional Activation In Response To IFNs and Other Extracellular Signaling Proteins", Articles, Science, vol. 264, pp. 1415-1421, (Jun. 3, 1994).
Zhong, Z. et al., "Stat3 And Stat4: Members Of The Family Of Signal Transducers And Activators Of Transcription", Biochemistry, Proc. Nitl. Acad. Sci, vol. 91 pp. 4806-4810, (May 1994).

(Continued)

Primary Examiner — D M Seaman
(74) Attorney, Agent, or Firm — Oblon, Spivak, McClelland, Maier & Neustadt, L.L.P.

(57) ABSTRACT

The present invention provides a STATS inhibitor containing as an active ingredient, a quinolinecarboxamide derivative represented by the formula (I) (in the formula, W represents a bond or an alkylene chain; X represents O, S, or $NR^{34}$; and $R^1$ to $R^8$ and $R^{34}$ each represent H, halogen, alkyl, phenyl, furyl, thienyl, or the like), or a pharmacologically acceptable salt thereof.

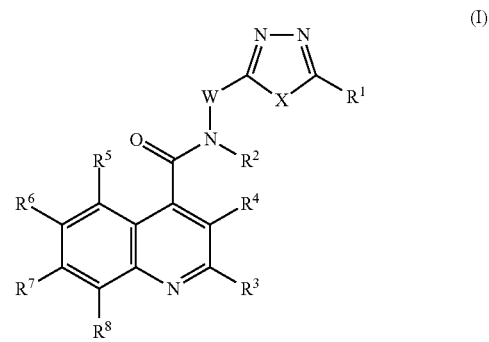

30 Claims, No Drawings

OTHER PUBLICATIONS

Niu, G. et al., "Gene Therapy With Dominant-Negative Stat3 Suppresses Growth Of The Murine Melanoma B16 Tumor In Vivo[1]", Cancer Research, vol. 59, pp. 5059-5063, (Oct. 15, 1999).

Gouilleux-Gruart, V. et al., "Activated Stat Related Transcription Factors In Acute Leukemia", Leukemia and Lymphoma, vol. 28, pp. 83-88 (Feb. 17, 1997).

Yu, C-L et al., "Constitutive Activation Of The Janus Kinase-STAT Pathway In T Lymphoma Overexpressing The Lck Protein Tyrosin Kinase[1]", The Journal of Immunology, vol. 159, pp. 5206-5210, (1997).

Yu, C-L et al., "Enhanced DNA-Binding Activity Of A Stat3-Related Protein In Cells Transformed By the Src Oncoprotein", Science, vol. 269, pp. 81-83, (Jul. 7, 1995).

Turkson, J. et al., "Stat3 Activation By Src Induces Specific Gene Regulation And Is Required For Cell Transformation", Molecular and Cellular Biology, vol. 18, No. 5, pp. 2545-2552, (May 1998).

Migone, T-S et al., "Constitutively Activated Jak-STAT Pathway In T Cells Transformed With HTLV-I", Reports, Science, vol. 269, pp. 79-81, (Jul. 7, 1995).

Grandis, J. R. et al., "Requirement of Stat3 but not Stat1 Activation For Epidermal Growth Factor Receptor-Mediated Cell Growth In Vitro", J. Clin. Invest., vol. 102, No. 7, pp. 1385-1392, (Oct. 1998).

Schust, J. et al., "Stattic: A Small-Molecule Inhibitor Of STAT3 Activation And Dimerization", Chemistry and Biology, vol. 13, pp. 1235-1242, (Nov. 2006).

Coleman, D. R. et al., "Investigation Of The Binding Determinants Of Phosphopeptides Targeted To The Src Homology 2 Domain Of the Signal Transducer And Activator Of Transcription 3. Development of A High-Affinity Peptide Inhibitor", J. Med. Chem., vol. 48, pp. 6661-6670, (Sep. 16, 2005).

International Search Report issued Aug. 4, 2009 in PCT/JP09/003235 filed Jul. 10, 2009.

* cited by examiner

STAT3 INHIBITOR CONTAINING QUINOLINECARBOXAMIDE DERIVATIVE AS ACTIVE INGREDIENT

TECHNICAL FIELD

The present invention relates to a STAT3 inhibitor containing a quinolinecarboxamide derivative or a pharmacologically acceptable salt thereof as an active ingredient, and to a novel quinolinecarboxamide derivative.

BACKGROUND ART

STAT (signal transducers and activators of transcription), a transcriptional regulator, is a DNA-binding protein whose activity is regulated by stimulations of various cytokines (IL-6, interferon, etc.) or growth factors (EGF, PDGF, etc.). Upon binding of cytokines to their receptors, JAK (Janus protein tyrosine kinase) kinase is activated to phosphorylate tyrosine in STAT (see e.g., Non Patent Documents 1 and 2). Moreover, upon binding of growth factors to their receptors, tyrosine kinase possessed by the growth factor receptors themselves phosphorylates STAT (see e.g., Non Patent Document 3). The phosphorylated STAT is activated by dimerization via its Src homology 2 (SH2) domain. The activated STAT moves into the nucleus where it specifically recognizes and binds particular DNA sequences in the gene promoter regions to induce the transcriptions of many genes. Specifically, STAT is a mediator essential for signal transduction pathways from cell surface to the nucleus and is deeply involved in cell growth or differentiation, etc.

For STAT, 6 different members (STAT1, STAT2, STAT3, STAT4, STAT5, and STAT6) and some isoforms (STAT1α, STAT1β, STAT3α, and STAT3β) are known.

Of them, STAT3 is expressed in the majority of cytomas (see e.g., Non Patent Document 4). Its constitutive activation and overexpression are observed in various cancer cells such as breast cancer, lung cancer, prostatic cancer, head and neck cancer, skin cancer, pancreatic cancer, and ovarian cancer cells, and in cancer cells such as myeloma, breast cancer, prostatic cancer, brain tumor, head and neck cancer, melanoma, leukemia lymphoma, and multiple myeloma cells (see e.g., Non Patent Documents 5, 6, and 7). The growth or invasion of these cancer cells is considered to depend on STAT3. Moreover, the abnormal or constitutive expression of STAT3 is also involved in cellular transformation (see e.g., Non Patent Documents 8, 9, and 10). Thus, STAT3 is probably useful as a target molecule for these cancer types. Its inhibitor is therefore expected as an anticancer agent.

It has been reported that an antisense oligonucleotide complementary to the translation initiation region of STAT3 actually inhibits TGF-α-stimulated cell growth induced by an epidermal growth factor receptor (EGFR) (see e.g., Non Patent Document 11). It has also been reported that inhibition of STAT3 functions (using antisense, RNAi, peptides, or the like) can suppress the growth of cancer cells and induce apoptosis. This suggests that a STAT3 inhibitor can serve as a therapeutic or preventive drug for cancer.

For example, 6-nitrobenzo[b]thiophene-1,1-dioxide (see e.g., Non Patent Document 12) and a phosphorylated oligopeptide (see e.g., Non Patent Document 13) are known as compounds inhibiting STAT3.

A 3-aminopyrazole derivative represented by the following formula (A):

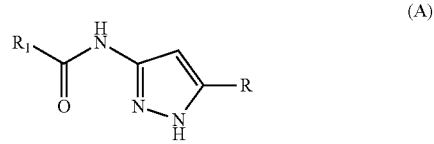

(wherein R represents an alkyl group, a cycloalkyl group, or the like, and $R_1$ represents an alkyl group, a heterocyclic group, an aryl group, or the like) [0010] is known as a therapeutic drug for cancer and cell proliferative disorder (see e.g., Patent Document 1). Examples of the aryl group include a phenyl group as well as aromatic heterocyclic groups such as pyridyl and quinolyl.

Moreover, a quinoline derivative represented by, for example, the following formula (B):

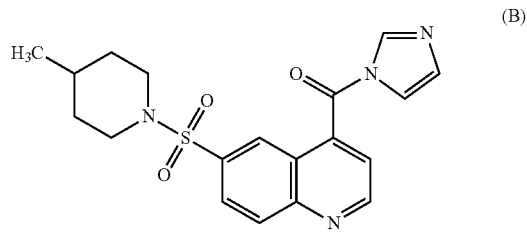 [SMILES: CC1CCN(S(=O)(=O)c2ccc3nccc(C(=O)n4ccnc4)c3c2)CC1]

is known to have caspase inhibitory activity (see e.g., Patent Document 2).

Furthermore, a (thiadiazolyl)quinolinecarboxamide derivative represented by, for example, the following formula (C):

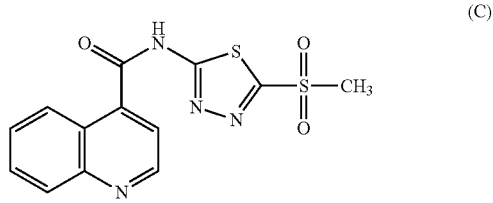 [SMILES: CS(=O)(=O)c1nnc(NC(=O)c2ccnc3ccccc23)s1]

is known to have antimicrobial or antifungal effect (see e.g., Non Patent Document 14).

PRIOR ART DOCUMENT

Patent Document

Patent Document 1: JP-A-2003-507329
Patent Document 2: International Publication No. WO2004/078731

Non Patent Document

Non Patent Document 1: Trends in Genetics, 1995, 11, 69-74
Non Patent Document 2: Proc. Natl. Acad. Sci. USA, 1998, 95, 5568-5572
Non Patent Document 3: Science, 1994, 264, 1415-1421
Non Patent Document 4: Proc. Natl. Acad. Sci. USA, 1994, 91, 4806-4810

Non Patent Document 5: Cancer Res., 1999, 59, 5059-5063
Non Patent Document 6: Leuk. Lymphoma, 1997, 28, 83-88
Non Patent Document 7: J. Immunol., 1997, 159, 5206-5210
Non Patent Document 8: Science, 1995, 269, 81-83
Non Patent Document 9: Mol. Cell. Biol., 1998, 18, 2545-2552
Non Patent Document 10: Science, 1995, 269, 79-81
Non Patent Document 11: J. Clin., Invest. 1998, 102, 1385-1392
Non Patent Document 12: Chemistry & Biology, 2006, 13, 1235-1242
Non Patent Document 13: J. Med. Chem., 2005, 48, 6661-6670
Non Patent Document 14: Med. Chem. Res., 2005, 14, 260-273

SUMMARY OF INVENTION

Problems to be Solved by the Invention

It is an object of the present invention is to provide a STAT3 inhibitor containing a quinolinecarboxamide derivative or a pharmacologically acceptable salt thereof as an active ingredient. It is also an object of the present invention is to provide an anticancer agent containing the STAT3 inhibitor as an active ingredient, and a novel quinolinecarboxamide derivative.

Means for Solving the Problems

As described above, the constitutive activation and overexpression of STAT3 are observed in many cancer cells, and the growth or invasion of these cancer cells is thought to depend on STAT3. Therefore, the present inventors have searched for a compound inhibiting STAT3 and consequently completed the present invention by finding that a quinolinecarboxamide derivative represented as a compound (I) has STAT3 inhibitory activity.

Specifically, the present invention relates to:
(1) a STAT3 inhibitor containing as an active ingredient, a quinolinecarboxamide derivative represented by the formula (I) or a pharmacologically acceptable salt thereof:

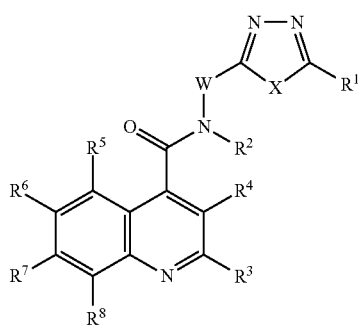

(I)

wherein
$R^1, R^2, R^3, R^4, R^5, R^6, R^7$, and $R^8$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q_1) NR^{11}R^{12}$ [wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)_m R^{16}$ (wherein m represents 0, 1, or 2, and $R^{16}$ is as defined above in $R^9$), $SO_2NR^{17}R^{19}$ (wherein $R^{17}$ and $R^{18}$ are the same or different and are as defined above in $R^{11}$ and $R^{12}$, respectively), $NR^{19}R^{20}$ [wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group], $N(R^{24})C(=Q^2)NR^{25}R^{26}$ [wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively], $N(R^{28}) SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}, R^{32}$, and $R^{33}$ are the same or different and are each as defined above in $R^9$), a nitro group, a cyano group, or a halogen atom, wherein any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring;
W represents a single bond or a substituted or unsubstituted alkylene group; and
X represents an oxygen atom, a sulfur atom, or $NR^{34}$ (wherein $R^{34}$ is as defined above in $R^9$).

Moreover, the present invention relates to:
(2) the STAT3 inhibitor according to (1), wherein X is an oxygen atom, the STAT3 inhibitor containing as an active ingredient, a quinolinecarboxamide derivative represented by the following formula (Ia) or a pharmacologically acceptable salt thereof:

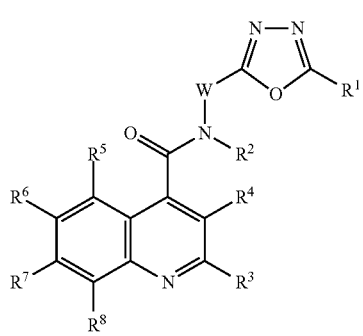

(Ia)

wherein R¹, R², R³, R⁴, R⁵, R⁶, R⁷, R⁸, and W are as defined above;

(3) the STAT3 inhibitor according to (2), containing as an active ingredient, a quinolinecarboxamide derivative wherein W is a single bond, or a pharmacologically acceptable salt thereof;

(4) the STAT3 inhibitor according to (3), containing as an active ingredient, a quinolinecarboxamide derivative wherein R¹ and R³ are the same or different and each are a substituted or unsubstituted aryl group, a substituted or unsubstituted aromatic heterocyclic group, a styryl group, or an alkoxy group, or a pharmacologically acceptable salt thereof;

(5) the STAT3 inhibitor according to (4) containing as an active ingredient, a quinolinecarboxamide derivative wherein the aryl group is a phenyl group or a naphthyl group, or a pharmacologically acceptable salt thereof;

(6) the STAT3 inhibitor according to (4), containing as an active ingredient, a quinolinecarboxamide derivative wherein the aromatic heterocyclic group is a furyl group or a thienyl group, or a pharmacologically acceptable salt thereof;

(7) the STAT3 inhibitor according to any of (4) to (6), containing as an active ingredient, a quinolinecarboxamide derivative wherein R¹ is a furyl group, and R³ is a substituted or unsubstituted phenyl group, a substituted or unsubstituted naphthyl group, a substituted or unsubstituted furyl group, a substituted or unsubstituted thienyl group, or a styryl group, or a pharmacologically acceptable salt thereof;

(8) the STAT3 inhibitor according to (7), containing as an active ingredient, a quinolinecarboxamide derivative wherein R⁶ is a fluorine atom, a chlorine atom, a bromine atom, a methyl group, a phenyl group, a hydroxyphenyl group, a thienyl group, a pyridyl group, a methoxy group, or a trifluoromethoxy group, or a pharmacologically acceptable salt thereof;

(9) the STAT3 inhibitor according to (4) or (5), containing as an active ingredient, a quinolinecarboxamide derivative wherein R¹ is a substituted or unsubstituted phenyl group, and R³ is a phenyl group, or a pharmacologically acceptable salt thereof;

(10) the STAT3 inhibitor according to (9), containing as an active ingredient, a quinolinecarboxamide derivative wherein R⁶ is a chlorine atom or a trifluoromethoxy group, or a pharmacologically acceptable salt thereof;

(11) the STAT3 inhibitor according to any of (2) to (10), containing as an active ingredient, a quinolinecarboxamide derivative wherein R² is a hydrogen atom, or a pharmacologically acceptable salt thereof;

(12) the STAT3 inhibitor according to (1), wherein X is a sulfur atom, the STAT3 inhibitor containing as an active ingredient, a quinolinecarboxamide derivative represented by the following formula (Ib) or a pharmacologically acceptable salt thereof:

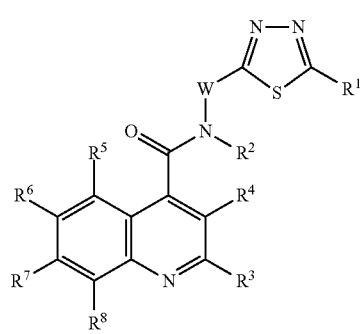

(Ib)

wherein R¹, R², R³, R⁴, R⁵, R⁶, R⁷, R⁸, and W are as defined above;

(13) the STAT3 inhibitor according to (12), containing as an active ingredient, a quinolinecarboxamide derivative wherein W is a single bond, or a pharmacologically acceptable salt thereof;

(14) the STAT3 inhibitor according to (13), containing as an active ingredient, a quinolinecarboxamide derivative wherein R¹ and R³ are the same or different and each are a substituted or unsubstituted aryl group or a substituted or unsubstituted aromatic heterocyclic group, or a pharmacologically acceptable salt thereof;

(15) the STAT3 inhibitor according to (14), containing as an active ingredient, a quinolinecarboxamide derivative wherein R¹ is a pyridyl group, and R³ is a substituted or unsubstituted phenyl group, a substituted or unsubstituted furyl group, a substituted or unsubstituted thienyl group, or a pyridyl group, or a pharmacologically acceptable salt thereof; and

(16) the STAT3 inhibitor according to any of (12) to (15), containing as an active ingredient, a quinolinecarboxamide derivative wherein R² is a hydrogen atom, or a pharmacologically acceptable salt thereof.

Moreover, the present invention relates to:

(17) an anticancer agent containing a STAT3 inhibitor according to any of (1) to (16) as an active ingredient.

Moreover, the present invention relates to:

(18) a quinolinecarboxamide derivative represented by the formula (I-1) or a pharmacologically acceptable salt thereof:

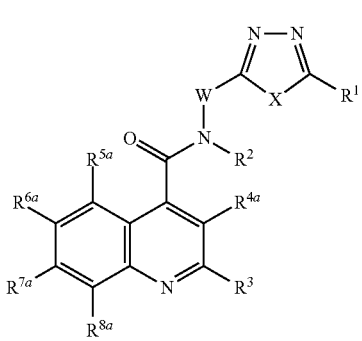

(I-1)

wherein
R¹, R², R³, R⁴ᵃ, R⁵ᵃ, R⁶ᵃ, R⁷ᵃ, and R⁸ᵃ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ [wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)mR^{15}$ (wherein m represents 0, 1, or 2, and $R^{15}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ [wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group], $N(R^{24})C(=Q^2)NR^{25}R^{26}$ [wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively], $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, and any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring, wherein at least one group of $R^{4a}$, $R^{5a}$, $R^{6a}$, $R^{7a}$, and $R^{8a}$ represents a group other than a hydrogen atom;

W represents a single bond or a substituted or unsubstituted alkylene group; and X represents an oxygen atom, a sulfur atom, or $NR^{34}$ (wherein $R^{34}$ is as defined above in $R^9$);

(19) the quinolinecarboxamide derivative according to (18) or a pharmaceutically acceptable salt thereof, wherein the compound represented by the formula (I-1) wherein X is an oxygen atom, W is a single bond, and $R^2$ is a hydrogen atom is represented by the following formula (I-1a):

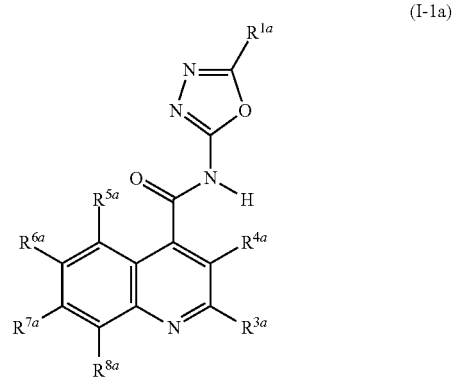

(I-1a)

wherein $R^{1a}$ and $R^{3a}$ are the same or different and each represent a substituted or unsubstituted aryl group or a substituted or unsubstituted aromatic heterocyclic group, and $R^{4a}$, $R^{5a}$, $R^{6a}$, $R^{7a}$, and $R^{8a}$ are as $R_{8a}$ fined above;

(20) the quinolinecarboxamide derivative according to (19), wherein in $R^{1a}$ and $R^{3a}$, the aryl group is a phenyl group, and the aromatic heterocyclic group is a furyl group or a thienyl group, or a pharmacologically acceptable salt thereof;

(21) the quinolinecarboxamide derivative according to (19) or (20), wherein $R^{1a}$ is a furyl group, and $R^{3a}$ is a substituted or unsubstituted phenyl group, a furyl group, or a thienyl group, or a pharmacologically acceptable salt thereof;

(22) the quinolinecarboxamide derivative according to any of (19) to (21), wherein at least one group of $R^{4a}$, $R^{5a}$, $R^{6a}$, $R^{7a}$, and $R^{8a}$ is a fluorine atom, a chlorine atom, a bromine atom, a methyl group, a phenyl group, a hydroxyphenyl group, a thienyl group, a pyridyl group, a methoxy group, or a trifluoromethoxy group, or a pharmacologically acceptable salt thereof;

(23) the quinolinecarboxamide derivative according to (19) or (20), wherein $R^{1a}$ is a substituted or unsubstituted phenyl group, and $R^{3a}$ is a phenyl group, or a pharmacologically acceptable salt thereof; and

(24) the quinolinecarboxamide derivative according to any of (19), (20), and (23), wherein $R^{6a}$ is a chlorine atom or a trifluoromethoxy group, or a pharmacologically acceptable salt thereof.

Furthermore, the present invention relates to:

(25) a quinolinecarboxamide derivative represented by the formula (I-2) or a pharmacologically acceptable salt thereof:

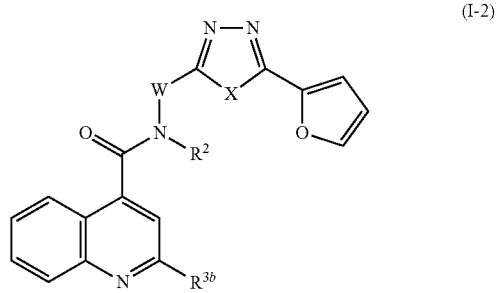

(I-2)

wherein R³ᵇ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group other than a phenyl group, a substituted or unsubstituted aralkyl group, a substituted or unsubstituted aromatic heterocyclic group other than 2-thienyl, a substituted or unsubstituted aromatic heterocyclic alkyl group, COR⁹ (wherein R⁹ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR¹⁰ (wherein R¹⁰ is as defined above in R⁹), (=Q₁)NR¹¹R¹² [wherein Q¹ represents an oxygen atom, a sulfur atom, or NR¹³ (wherein R¹³ is as defined above in R⁹), and R¹¹ and R¹² are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by R¹¹ and R¹² together represents a nitrogen-containing heterocyclic group], OR¹⁴ (wherein R¹⁴ is as defined above in R⁹), OCOR¹⁵ (wherein R¹⁵ is as defined above in R⁹), S(O)ₘR¹⁶ (wherein m represents 0, 1, or 2, and R¹⁶ is as defined above in R⁹), SO₂NR¹⁷R¹⁸ (wherein R¹⁷ and R¹⁹ are the same or different and are as defined above in R¹¹ and R¹², respectively), NR¹⁹R²⁰ [wherein R¹⁹ and R²⁰ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR²¹ (wherein R²¹ is as defined above in R⁹), COOR²² (wherein R²² is as defined above in R⁹), or SO₂R²³ (wherein R²³ is as defined above in R⁹), or a group which is formed by linking R¹⁹ and R²⁰ together represents a nitrogen-containing heterocyclic group], N(R²⁴)C(=Q²)NR²⁵R²⁶ [wherein Q² represents an oxygen atom, a sulfur atom, NR²⁷ (wherein R²⁷ is as defined above in R⁹), NCN, CHNO₂, or C(CN)₂, R²⁴ is as defined above in R⁹, and R²⁵ and R²⁶ are the same or different and are as defined above in R¹¹ and R¹², respectively], N(R²⁸) SO₂NR²⁹R³⁰ (wherein R²⁸ is as defined above in R⁹, and R²⁹ and R³⁰ are the same or different and are as defined above in R¹¹ and R¹², respectively), SiR³¹R³²R³³ (wherein R³¹, R³², and R³³ are the same or different and are each as defined above in R⁹), a nitro group, a cyano group, or a halogen atom; and R², W, and X are as defined above; and

(26) the quinolinecarboxamide derivative according to (25) or a pharmacologically acceptable salt thereof, wherein the compound represented by the formula (I-2) wherein X is an oxygen atom, W is a single bond, and R² is a hydrogen atom is represented by the following formula (I-2a):

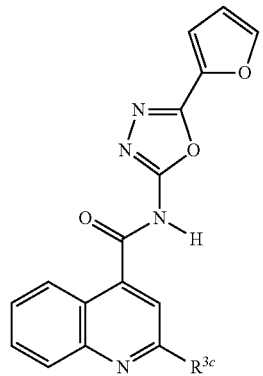

(I-2a)

wherein R³ᶜ represents a substituted phenyl group, a substituted or unsubstituted naphthyl group, a substituted or unsubstituted furyl group, a substituted thienyl group, a styryl group, or an alkoxy group.

Effects of the Invention

A quinolinecarboxamide derivative (I) used in the present invention has excellent STAT3 inhibitory activity, which has been unknown so far, and has activity as an anticancer agent for various cancers.

MODE FOR CARRYING OUT THE INVENTION

Hereinafter, the definition of each group in a compound (I) used as a STAT3 inhibitor of the present invention will be exemplified specifically. However, they are shown as preferable examples of the present invention and do not limit the present invention, as a matter of course.

Examples of the alkyl moieties of alkyl and alkoxy groups include linear or branched alkyl having 1 to 12 carbon atoms, specifically, methyl, ethyl, propyl, isopropyl, butyl, isobutyl, sec-butyl, tert-butyl, pentyl, isopentyl, neopentyl, hexyl, heptyl, octyl, nonyl, decyl, undecyl, and dodecyl.

A cycloalkyl group is a 3- to 12-membered cycloalkyl group which may contain a saturated or partially unsaturated bond, and may be a monocyclic cycloalkyl group or a polycyclic condensed cycloalkyl group containing a plurality of the monocyclic cycloalkyl groups condensed or the monocyclic cycloalkyl group condensed with an aryl or aromatic heterocyclic group. Examples of the monocyclic cycloalkyl group include monocyclic cycloalkyl having 3 to 8 carbon atoms, specifically, cyclopropyl, cyclobutyl, cyclopentyl, cyclohexyl, cycloheptyl, cyclooctyl, cyclododecyl, and 1-cyclohexenyl. Examples of the polycyclic cycloalkyl group include polycyclic cycloalkyl having 5 to 12 carbon atoms, specifically, pinanyl, adamantyl, bicyclo[3.3.1]octyl, and bicyclo[3.1.1]heptyl.

Examples of an alkenyl group include linear or branched alkenyl having 2 to 12 carbon atoms, specifically, vinyl, allyl, 1-propenyl, isopropenyl, methacryl, butenyl, 1,3-butadienyl, crotyl, pentenyl, hexenyl, heptenyl, decenyl, and dodecenyl.

Examples of an alkynyl group include linear or branched alkynyl having 2 to 12 carbon atoms, specifically, ethynyl, propargyl, 1-propynyl, isopropynyl, 2-butynyl, pentynyl, 2-penten-4-ynyl, hexynyl, heptynyl, decynyl, and dodecynyl.

An alicyclic heterocyclic group is a 3- to 8-membered alicyclic heterocyclic group which contains at least one or more identical or different heteroatoms, for example, nitrogen, oxygen, and sulfur and may contain a saturated or partially unsaturated bond, and may be a monocyclic alicyclic heterocyclic group or a polycyclic condensed alicyclic heterocyclic group containing a plurality of the monocyclic heterocyclic groups condensed or the monocyclic heterocyclic group condensed with an aryl or aromatic heterocyclic group. Examples of the monocyclic alicyclic heterocyclic group can specifically include aziridinyl, pyrrolidinyl, imidazolidinyl, imidazolinyl, pyrazolidinyl, pyrazolinyl, dihydrothiazolyl, tetrahydrofuranyl, 1,3-dioxolanyl, thiolanyl, oxazolidinyl, thiazolidinyl, piperidino, piperidinyl, piperazinyl, homopiperidinyl, morpholino, morpholinyl, thiomorpholinyl, pyranyl, oxathianyl, oxadiazinyl, thiadiazinyl, dithiazinyl, azepinyl, and dihydroazocinyl. Examples of the polycyclic condensed alicyclic heterocyclic group can specifically include indolinyl, isoindolinyl, chromanyl, isochromanyl, and quinuclidinyl.

Examples of an aryl group can include aryl having 6 to 14 carbon atoms, specifically, phenyl, naphthyl, anthryl, and phenanthryl.

The aryl moiety of an aralkyl group is as defined above in the aryl group, and the alkyl moiety thereof is as defined above in the alkyl group. Examples thereof can include aralkyl having 7 to 15 carbon atoms, specifically, benzyl, phenethyl, phenylpropyl, phenylbutyl, benzhydryl, trityl, naphthylmethyl, naphthylethyl, and phenylcyclopropyl.

An aromatic heterocyclic group is a 5- or 6-membered aromatic heterocyclic group which contains at least one or more identical or different heteroatoms, for example, nitrogen, oxygen, and sulfur. The heterocyclic group may be a monocyclic heterocyclic group or a polycyclic condensed aromatic heterocyclic group (e.g., a bicyclic or tricyclic heterocyclic group) containing a plurality of the monocyclic heterocyclic groups condensed or the monocyclic heterocyclic group condensed with an aryl group. Specific examples of the monocyclic aromatic heterocyclic group include furyl, thienyl, pyrrolyl, imidazolyl, pyrazolyl, triazolyl, tetrazolyl, oxazolyl, isoxazolyl, oxadiazolyl, thiazolyl, thiadiazolyl, isothiazolyl, pyridyl, pyrimidinyl, pyrazinyl, pyridazinyl, and triazinyl. Examples of the polycyclic condensed aromatic heterocyclic group can include benzofuryl, benzothienyl, indolyl, isoindolyl, indazolyl, benzimidazolyl, benzotriazolyl, benzoxazolyl, benzothiazolyl, carbazolyl, purinyl, quinolyl, isoquinolyl, quinazolinyl, phthalazinyl, quinoxalinyl, cinnolinyl, naphtylidinyl, pyridopyrimidinyl, pyrimidopyrimidinyl, pteridinyl, acridinyl, thianthrenyl, phenoxathinyl, phenoxazinyl, phenothiazinyl, and phenazinyl.

The aromatic heterocyclic moiety of an aromatic heterocyclic alkyl group is as defined above in the aromatic heterocyclic group, and the alkyl moiety thereof is as defined above in the alkyl group. Examples thereof can include aromatic heterocyclic alkyl containing at least one or more heteroatoms, specifically, pyridylmethyl, pyridylethyl, furanylmethyl, and thienylmethyl.

A nitrogen-containing heterocyclic group is, of the alicyclic or aromatic heterocyclic groups, a heterocyclic group containing at least one nitrogen atom as a heteroatom. Specific examples thereof can include aziridinyl, pyrrolidinyl, piperidino, homopiperidinyl, piperazinyl, homopiperazinyl, morpholino, thiomorpholinyl, pyrrolyl, imidazolyl, pyrazolyl, triazolyl, tetrazolyl, indolyl, indazolyl, benzimidazolyl, and benzotriazolyl.

A halogen atom means each of fluorine, chlorine, bromine, and iodine atoms.

Examples of an alicyclic hydrocarbon ring include an alicyclic hydrocarbon ring corresponding to the cycloalkyl group having 5 to 8 carbon atoms, specifically, cyclopentane, cyclohexane, and cyclooctane.

Examples of an alicyclic heterocyclic ring can include a 5- to 8-membered alicyclic heterocyclic ring corresponding to the alicyclic heterocyclic group, specifically, pyrroline, pyrrolidine, imidazoline, imidazolidine, pyrazoline, pyrazolidine, dihydrothiazole, tetrahydrofuran, dioxolane, thiolane, piperidine, piperazine, morpholine, thiomorpholine, pyrane, oxathiane, oxadiazine, thiadiazine, and dithiazine.

Examples of an aromatic hydrocarbon ring can include an aromatic hydrocarbon ring corresponding to the aryl group having 6 to 14 carbon atoms, specifically, benzene, naphthalene, and anthracene.

Examples of an aromatic heterocyclic ring can include a 5- to 6-membered aromatic heterocyclic ring corresponding to the aromatic heterocyclic group, specifically, monocyclic aromatic heterocyclic rings such as furan, thiophene, pyrrole, oxazole, isoxazole, thiazole, thiadiazole, isothiazole, imidazole, pyrazole, triazole, pyridine, pyrazine, pyrimidine, and pyridazine, and condensed aromatic heterocyclic rings such as benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, and quinoxaline.

Examples of an alkylene group include linear or branched alkylene having 1 to 12 carbon atoms, specifically, methylene, ethylene, propylene, trimethylene, tetramethylene, pentamethylene, hexamethylene, heptamethylene, octamethylene, nonamethylene, decamethylene, undecamethylene, and dodecamethylene.

Moreover, these groups respectively represent all of their possible positional isomers, if any.

Substituents for the alkyl group, the alkenyl group, the alkynyl group, the cycloalkyl group, the alicyclic heterocyclic group, the aryl group, the aralkyl group, the aromatic heterocyclic group, the aromatic heterocyclic alkyl group, the nitrogen-containing heterocyclic group, the alicyclic hydrocarbon ring, the alicyclic heterocyclic ring, the aromatic hydrocarbon ring, the aromatic heterocyclic ring, and the alkylene group are appropriately selected from, for example, an alkyl group, an alkenyl group, an alkynyl group, a cycloalkyl group, an alicyclic heterocyclic group, an aryl group, an aralkyl group, an aromatic heterocyclic group, an aromatic heterocyclic alkyl group, $OR^a$, $NR^bR^c$, $S(O)qR^d$ (wherein q represents 0, 1, or 2), $COR^e$, $COOR^f$, $OCOR^g$, $CONR^hR^i$, $NR^jCOR^k$, $NR^lCOOR^m$, $NR''SO_2R^o$, $C(=NR^p)NR^qR^r$, $NR^sSO_2NR^tR^u$, $SO_2NR^vR^w$, a nitro group, a cyano group, and a halogen atom. In this context, $R^a$ to $R^w$ are the same or different and each represent a hydrogen atom, an alkyl group, an alkenyl group, an alkynyl group, a cycloalkyl group, an alicyclic heterocyclic group, an aryl group, an aralkyl group, an aromatic heterocyclic group, an aromatic heterocyclic alkyl group, or the like, and $R^b$ and $R^c$, $R^h$ and $R^i$, $R^q$ and $R^r$, $R^t$ and $R^u$, and $R^v$ and $R^w$ may be linked together to form a nitrogen-containing heterocyclic group.

The alkyl, alkenyl, alkynyl, cycloalkyl, alicyclic heterocyclic, aryl, aralkyl, aromatic heterocyclic, aromatic heterocyclic, and nitrogen-containing heterocyclic groups are as defined above.

Moreover, the alkyl, alkenyl, alkynyl, cycloalkyl, alicyclic heterocyclic, aryl, aralkyl, aromatic heterocyclic, aromatic heterocyclic, and nitrogen-containing heterocyclic groups as substituents may further have a substituent. Examples of this substituent include the same as the substituents exemplified above.

The number of substitutions by these substituents may be the number of hydrogen atoms present in each group (these hydrogen atoms may be substituted by identical or different substituents), at the maximum, and is preferably 1 to 10, more preferably 1 to 5.

The compound represented by the formula (I) used as the STAT3 inhibitor of the present invention (hereinafter, referred to as a compound (I); the same holds true for compounds represented by other formula numbers) is useful as an anticancer agent. Any compound (I) can be used as an anticancer agent without particular limitations.

In the compound (I) used as a STAT3 inhibitor, for example, X is an oxygen atom, i.e., this compound (I) is preferably a quinolinecarboxamide derivative represented by the following formula (Ia):

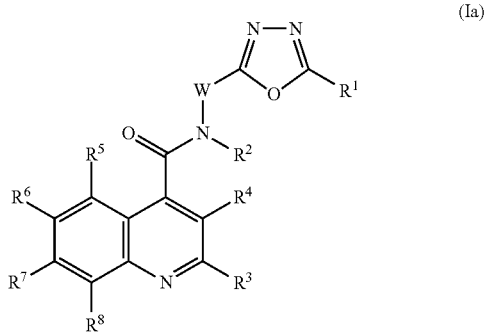

(Ia)

wherein $R^1$, $R^2$, $R^3$, $R^4$, $R^5$, $R^6$, $R^7$, $R^8$, and W are as defined above.

A particularly preferable compound (Ia) is a quinolinecarboxamide derivative wherein W is a single bond, and $R^2$ is a hydrogen atom. Moreover, a more preferable compound (Ia) is a compound wherein $R^1$ and $R^3$ are the same or different and each represent a substituted or unsubstituted aryl group, a substituted or unsubstituted aromatic heterocyclic group, a styryl group, or an alkoxy group. Specific examples of the aryl group include phenyl and naphthyl groups. Examples of the aromatic heterocyclic group include furyl and thienyl groups. Examples of the alkoxy group include a butoxy group. An even more preferable compound (Ia) is a compound wherein $R^1$ is a furyl group, and $R^3$ is a substituted or unsubstituted phenyl group, a substituted or unsubstituted furyl group, or a substituted or unsubstituted thienyl group. Examples of a substituent for the substituted phenyl group include: alkyl groups such as a methyl group; substituted or unsubstituted alkoxy groups such as methoxy and difluoromethoxy groups; halogen atoms such as fluorine and chlorine atoms; a hydroxyl group; alkoxycarbonyl groups such as tert-butoxycarbonyl; an amino group; a nitro group; and a cyano group. Examples of a substituent for the substituted furyl and thienyl groups include: alkyl groups such as a methyl group; and halogen atoms such as a chlorine atom. A further preferable compound (Ia) is a compound wherein $R^6$ is a fluorine atom, a chlorine atom, a bromine atom, a methyl group, a phenyl group, a hydroxyphenyl group, a thienyl group, a pyridyl group, a methoxy group, or a trifluoromethoxy group. Moreover, a compound wherein $R^1$ is a substituted or unsubstituted phenyl group, and $R^3$ is a phenyl group is preferable. Examples of a substituent for the substituted phenyl group include: alkoxy groups such as a methoxy group; halogen atoms such as a chlorine atom; and a nitro group.

Specific examples of these compounds (Ia) include compounds described later in Tables 1 to 14 and 17. The compounds (Ia) are particularly preferably N-[5-(2-furyl)-1,3,4-oxadiazol-2-yl]-2-phenyl-4-quinolinecarboxamide (compound Ia-1), N-[5-(3-furyl)-1,3,4-oxadiazol-2-yl]-2-phenyl-4-quinolinecarboxamide (compound Ia-2), 2-phenyl-N-(5-phenyl-1,3,4-oxadiazol-2-yl)-4-quinolinecarboxamide (compound Ia-3), N-[5-(4-chlorophenyl)-1,3,4-oxadiazol-2-yl]-2-phenyl-4-quinolinecarboxamide (compound Ia-5), N-[5-(4-nitrophenyl)-1,3,4-oxadiazol-2-yl]-2-phenyl-4-quinolinecarboxamide (compound Ia-7), 2-phenyl-N-[5-(3-pyridyl)-1,3,4-oxadiazol-2-yl]-4-quinolinecarboxamide (compound Ia-9), N-[(5-phenyl-1,3,4-oxadiazol-2-yl)methyl]-4-quinolinecarboxamide (compound Ia-10), N-[5-(2-furyl)-1,3,4-oxadiazol-2-yl]-2-piperidino-4-quinolinecarboxamide (compound Ia-14), N-[5-(2-furyl)-1,3,4-oxadiazol-2-yl]-2-(3-nitrophenyl)-4-quinolinecarboxamide (compound Ia-16), 2-(4-cyanophenyl)-N-[5-(2-furyl)-1,3,4-oxadiazol-2-yl]-4-quinolinecarboxamide (compound Ia-17), 2-(2-furyl)-N-[5-(2-furyl)-1,3,4-oxadiazol-2-yl]-4-quinolinecarboxamide (compound Ia-18), 2-(5-chloro-2-thienyl)-N-[5-(2-furyl)-1,3,4-oxadiazol-2-yl]-4-quinolinecarboxamide (compound Ia-19), 6-chloro-N-[5-(2-furyl)-1,3,4-oxadiazol-2-yl]-2-phenyl-4-quinolinecarboxamide (compound Ia-22), N-[5-(2-furyl)-1,3,4-oxadiazol-2-yl]-6-methoxy-2-phenyl-4-quinolinecarboxamide (compound Ia-23), 7-bromo-N-[5-(2-furyl)-1,3,4-oxadiazol-2-yl]-2-phenyl-4-quinolinecarboxamide (compound Ia-24), N-[5-(2-furyl)-1,3,4-oxadiazol-2-yl]-8-methyl-2-phenyl-4-quinolinecarboxamide (compound Ia-25), 7-chloro-N-[5-(2-furyl)-1,3,4-oxadiazol-2-yl]-8-methyl-2-phenyl-4-quinolinecarboxamide (compound Ia-26), N-[5-(2-furyl)-1,3,4-oxadiazol-2-yl]-8-methyl-2-(4-tolyl)-4-quinolinecarboxamide (compound Ia-27), 7-chloro-2-(2-furyl)-N-[5-(2-furyl)-1,3,4-oxadiazol-2-yl]-8-methyl-4-quinolinecarboxamide (compound Ia-28), N-[5-(2-furyl)-1,3,4-oxadiazol-2-yl]-6-methyl-2-(2-thienyl)-4-quinolinecarboxamide (compound Ia-29), 6-chloro-N-[5-(2-furyl)-1,3,4-oxadiazol-2-yl]-2-(2-thienyl)-4-quinolinecarboxamide (compound Ia-30), 8-chloro-N-[5-(2-furyl)-1,3,4-oxadiazol-2-yl]-2-(2-thienyl)-4-quinolinecarboxamide (compound Ia-32), N-[5-(2-furyl)-1,3,4-oxadiazol-2-yl]-6,8-dimethyl-2-(2-thienyl)-4-quinolinecarboxamide (compound Ia-33), 2-(1-butoxy)-N-[5-(2-furyl)-1,3,4-oxadiazol-2-yl]-4-quinolinecarboxamide (compound Ia-35), 2-(2-chlorophenyl)-N-[5-(2-furyl)-1,3,4-oxadiazol-2-yl]-4-quinolinecarboxamide (compound Ia-37), N-[5-(2-furyl)-1,3,4-oxadiazol-2-yl]-2-(2-hydroxyphenyl)-4-quinolinecarboxamide (compound Ia-38), 2-(2-aminophenyl)-N-[5-(2-furyl)-1,3,4-oxadiazol-2-yl]-4-quinolinecarboxamide (compound Ia-40), 2-(3-chlorophenyl)-N-[5-(2-furyl)-1,3,4-oxadiazol-2-yl]-4-quinolinecarboxamide (compound Ia-41), N-[5-(2-furyl)-1,3,4-oxadiazol-2-yl]-2-(3-methoxyphenyl)-4-quinolinecarboxamide (compound Ia-42), 2-(3-cyanophenyl)-N-[5-(2-furyl)-1,3,4-oxadiazol-2-yl]-4-quinolinecarboxamide (compound Ia-43), 2-(3-tert-butoxycarbonylphenyl)-N-[5-(2-furyl)-1,3,4-oxadiazol-2-yl]-4-quinolinecarboxamide (compound Ia-44), 2-(4-fluorophenyl)-N-[5-(2-furyl)-1,3,4-oxadiazol-2-yl]-4-quinolinecarboxamide (compound Ia-46), 2-(4-chlorophenyl)-N-[5-(2-furyl)-1,3,4-oxadiazol-2-yl]-4-quinolinecarboxamide (compound Ia-47), N-[5-(2-furyl)-1,3,4-oxadiazol-2-yl]-2-(4-methylphenyl)-4-quinolinecarboxamide (compound Ia-48), 2-(4-difluoromethoxyphenyl)-N-[5-(2-furyl)-1,3,4-oxadiazol-2-yl]-4-quinolinecarboxamide (compound Ia-49), N-[5-(2-furyl)-1,3,4-oxadiazol-2-yl]-2-(4-hydroxyphenyl)-4-quinolinecarboxamide (compound Ia-50), N-[5-(2-furyl)-1,3,4-oxadiazol-2-yl]-2-(4-methoxyphenyl)-4- quinolinecarboxamide (compound Ia-51), N-[5-(2-furyl)-1, 3,4-oxadiazol-2-yl]-2-(4-nitrophenyl)-4-quinolinecarboxamide (compound Ia-52), 2-(4-tert-butoxycarbonylphenyl)-N-[5-(2-furyl)-1,3,4-oxadiazol-2-yl]-4-quinolinecarboxamide (compound Ia-53), N-[5-(2-furyl)-1,3,4-oxadiazol-2-yl]-2-(2,4-dimethylphenyl)-4-quinolinecarboxamide (compound Ia-56), N-[5-(2-furyl)-1, 3,4-oxadiazol-2-yl]-2-(3,4-dimethoxyphenyl)-4-quinolinecarboxamide (compound Ia-57), N-[5-(2-furyl)-1, 3,4-oxadiazol-2-yl]-2-(3,4-methylenedioxyphenyl)-4-quinolinecarboxamide (compound Ia-58), N-[5-(2-furyl)-1, 3,4-oxadiazol-2-yl]-2-(1-naphthyl)-4-quinolinecarboxamide (compound Ia-60), N-[5-(2-furyl)-1, 3,4-oxadiazol-2-yl]-2-(6-methoxy-2-naphthyl)-quinolinecarboxamide (compound Ia-61), N-[5-(2-furyl)-1, 3,4-oxadiazol-2-yl]-2-(5-methyl-2-furyl)-4-quinolinecarboxamide (compound Ia-64), N-[5-(2-furyl)-1, 3,4-oxadiazol-2-yl]-2-trans-styryl-4-quinolinecarboxamide (compound Ia-65), 6-fluoro-N-[5-(2-furyl)-1,3,4-oxadiazol-2-yl]-2-phenyl-4-quinolinecarboxamide (compound Ia-67), 6-bromo-N-[5-(2-furyl)-1,3,4-oxadiazol-2-yl]-2-phenyl-4-quinolinecarboxamide (compound Ia-68), N-[5-(2-furyl)-1, 3,4-oxadiazol-2-yl]-6-methyl-2-phenyl-4-quinolinecarboxamide (compound Ia-70), N-[5-(2-furyl)-1,3,4-oxadiazol-2-yl]-2-phenyl-6-trifluoromethoxy-4-quinolinecarboxamide (compound Ia-71), 7-chloro-N-[5-(2-furyl)-1,3,4-oxadiazol-2-yl]-2-phenyl-4-quinolinecarboxamide (compound Ia-72), 6,8-dichloro-N-[5-(2-furyl)-1,3,4-oxadiazol-2-yl]-2-phenyl-4-quinolinecarboxamide (compound Ia-74), N-[5-(2-furyl)-1,3,4-oxadiazol-2-yl]-2,6-diphenyl-4-quinolinecarboxamide (compound Ia-75), N-[5-(2-furyl)-1,3,4-oxadiazol-2-yl]-2-phenyl-6-(4-pyridyl)-4-quinolinecarboxamide (compound Ia-76), 8-chloro-2-(2-furyl)-N-[5-(2-furyl)-1,3,4-oxadiazol-2-yl]-4-quinolinecarboxamide (compound Ia-79), N-(5-benzyl-1,3,4-oxadiazol-2-yl)-2-phenyl-4-quinolinecarboxamide (compound Ia-83), N-[5-(5-nitro-2-furyl)-1,3,4-oxadiazol-2-yl]-2-phenyl-4-quinolinecarboxamide (compound Ia-84), N-[5-(2-furyl)-1,3,4-oxadiazol-2-yl]-6-[2-(dimethylamino)ethoxy]-2-phenyl-4-quinolinecarboxamide (compound Ia-88), N-[5-(2-furyl)-1,3,4-oxadiazol-2-yl]-6-(2-methoxyethoxy)-2-phenyl-4-quinolinecarboxamide (compound Ia-89), 6-benzyloxy-N-[5-(2-furyl)-1,3,4-oxadiazol-2-yl]-2-phenyl-4-quinolinecarboxamide (compound Ia-90), N-[5-(2-furyl)-1,3,4-oxadiazol-2-yl]-2-phenyl-6-propionylamino-4-quinolinecarboxamide (compound Ia-93), 6-butyrylamino-N-[5-(2-furyl)-1,3,4-oxadiazol-2-yl]-2-phenyl-4-quinolinecarboxamide (compound Ia-94), N-[5-(2-furyl)-1,3,4-oxadiazol-2-yl]-6-(4-hydroxyphenyl)-2-phenyl-4-quinolinecarboxamide (compound Ia-98), N-[5-(2-furyl)-1,3,4-oxadiazol-2-yl]-6-(3-thienyl)-2-phenyl-4-quinolinecarboxamide (compound Ia-99), N-[5-(2-furyl)-1, 3,4-oxadiazol-2-yl]-6-(3-pyridyl)-2-phenyl-4-quinolinecarboxamide (compound Ia-100), 6-chloro-2-phenyl-N-(5-phenyl-1,3,4-oxadiazol-2-yl)-4-quinolinecarboxamide (compound Ia-110), N-(5-phenyl-1,3, 4-oxadiazol-2-yl)-2-phenyl-6-trifluoromethoxy-4-quinolinecarboxamide (compound Ia-111), 6-chloro-N-[5-(2-chlorophenyl)-1,3,4-oxadiazol-2-yl]-2-phenyl-4-quinolinecarboxamide (compound Ia-112), N-[5-(2-chlorophenyl)-1,3,4-oxadiazol-2-yl]-2-phenyl-6-trifluoromethoxy-4-quinolinecarboxamide (compound Ia-113), N-[5-(4-methoxyphenyl)-1,3,4-oxadiazol-2-yl]-2-phenyl-6-trifluoromethoxy-4-quinolinecarboxamide (compound Ia-117), N-[5-(5-chloro-2-thienyl)-1,3,4-oxadiazol-2-yl]-2-phenyl-4-quinolinecarboxamide (compound Ia-b), N-[5-(4-methoxyphenyl)-1,3,4-oxadiazol-2-yl]-2-phenyl-4-quinolinecarboxamide (compound Ia-d), and N-(5-phenyl-1, 3,4-oxadiazol-2-yl)-2-(2-thienyl)-4-quinolinecarboxamide (compound Ia-j), etc.

Moreover, in the compound (I) used as a STAT3 inhibitor, for example, X is a sulfur atom, i.e., this compound (I) is preferably a quinolinecarboxamide derivative represented by the following formula (Ib):

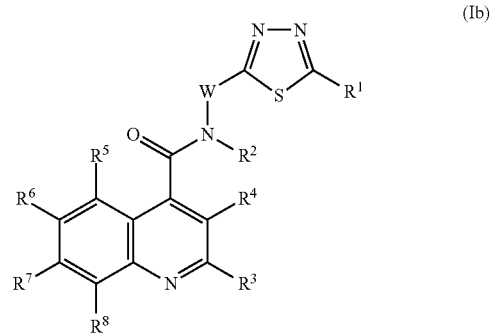

wherein $R^1$, $R^2$, $R^3$, $R^4$, $R^5$, $R^6$, $R^7$, $R^8$, and W are as defined above.

A particularly preferable compound (Ib) is a quinolinecarboxamide derivative wherein W is a single bond, and $R^2$ is a hydrogen atom. Moreover, a more preferable compound (Ib) is a compound wherein $R^1$ and $R^3$ are the same or different and each represent a substituted or unsubstituted aryl group or a substituted or unsubstituted aromatic heterocyclic group. Specific examples of the aryl group include a phenyl group. Examples of the aromatic heterocyclic group include furyl, thienyl, and pyridyl groups. An even more preferable compound (Ib) is a compound wherein $R^1$ is a pyridyl group, and $R^3$ is a substituted or unsubstituted phenyl group, a substituted or unsubstituted furyl group, a substituted or unsubstituted thienyl group, or a substituted or unsubstituted pyridyl group. Examples of a substituent for the substituted phenyl, furyl, thienyl, and pyridyl groups include: alkyl groups such as a methyl group; and alkoxy groups such as methoxy and isopropoxy groups.

Specific examples of these compounds (Ib) include compounds described later in Tables 15 and 18. The compounds (Ib) are particularly preferably N-(5-bromo-1,3,4-thiadiazol-2-yl)-2-phenyl-4-quinolinecarboxamide (compound Ib-2), N-[5-(2-furyl)-1,3,4-thiadiazol-2-yl]-2-phenyl-4-quinolinecarboxamide (compound Ib-4), 2-phenyl-N-[5-(4-pyridyl)-1,3,4-thiadiazol-2-yl]-6-trifluoromethoxy-4-quinolinecarboxamide (compound Ib-8), 2-(2,5-dimethoxyphenyl)-N-[5-(4-pyridyl)-1,3,4-thiadiazol-2-yl]-4-quinolinecarboxamide (compound Ib-c), 6-chloro-2-(3-pyridyl)-N-[5-(4-pyridyl)-1, 3,4-thiadiazol-2-yl]-4-quinolinecarboxamide (compound Ib-d), 2-(5-methyl-2-furyl)-N-[5-(4-pyridyl)-1,3,4-thiadiazol-2-yl]-4-quinolinecarboxamide (compound Ib-e), and 6-chloro-2-(2,5-dimethyl-3-thienyl)-N-[5-(4-pyridyl)-1,3,4-thiadiazol-2-yl]-4-quinolinecarboxamide (compound Ib-f), etc.

Furthermore, in the compound (I) used as a STAT3 inhibitor, for example, X is N—R$^{34}$, i.e., this compound (I) is preferably a quinolinecarboxamide derivative represented by the following formula (Ic):

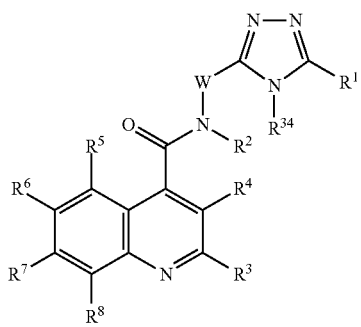

wherein R$^1$, R$^2$, R$^3$, R$^4$, R$^5$, R$^6$, R$^7$, R$^8$, R$^{34}$, and W are as defined above.

A particularly preferable compound (Ic) is a quinolinecarboxamide derivative wherein W is a single bond, and R$^2$ is a hydrogen atom. Moreover, a more preferable compound (Ic) is a compound wherein R$^3$ is a substituted or unsubstituted aryl group. Specific examples of the aryl group include a phenyl group. Specific examples of these compounds (Ic) include compounds described later in Table 16. The compounds (Ic) are particularly preferably 2-phenyl-N-(1,3,4-triazol-2-yl)-4-quinolinecarboxamide (compound Ic-1), etc.

Examples of a pharmacologically acceptable salt of the compound (I) include pharmacologically acceptable acid-addition salts, metal salts, ammonium salts, organic amine-addition salts, and amino acid-addition salts. Examples of the pharmacologically acceptable acid-addition salts include salts of inorganic acids such as hydrochloric acid, hydrobromic acid, sulfuric acid, nitric acid, phosphoric acid, and boric acid, or organic acids such as carboxylic acids (e.g., formic acid, acetic acid, propionic acid, fumaric acid, malonic acid, succinic acid, maleic acid, tartaric acid, citric acid, and benzoic acid), sulfonic acids (e.g., methanesulfonic acid and p-toluenesulfonic acid), and amino acids (e.g., glutamic acid and aspartic acid). Examples of the pharmacologically acceptable metal salts include: salts of alkali metals such as lithium, sodium, and potassium; salts of alkaline earth metals such as magnesium and calcium; and salts of metals such as aluminum and zinc. Examples of the pharmacologically acceptable ammonium salts include salts of ammonium or tetramethylammonium. Examples of the pharmacologically acceptable organic amine salts include salts of triethylamine, piperidine, morpholine, or toluidine. Examples of the pharmacologically acceptable amino acid-addition salts include lysine-, glycine-, and phenylalanine-addition salts.

Next, a production method of the compound (I) will be described. The compound can be produced using a routine method or the acid amide synthesis method described in a document (e.g., The Chemical Society of Japan, ed., "Experimental Chemistry Guidebook 16, 5th ed., Synthesis of Organic compounds IV, Carboxylic Acid/Amino acid/Peptide", Maruzen Co., Ltd., March 2005, p. 118-146 and p. 258-270).

Production Method 1

The compound (I) can be produced according to the following reaction steps:

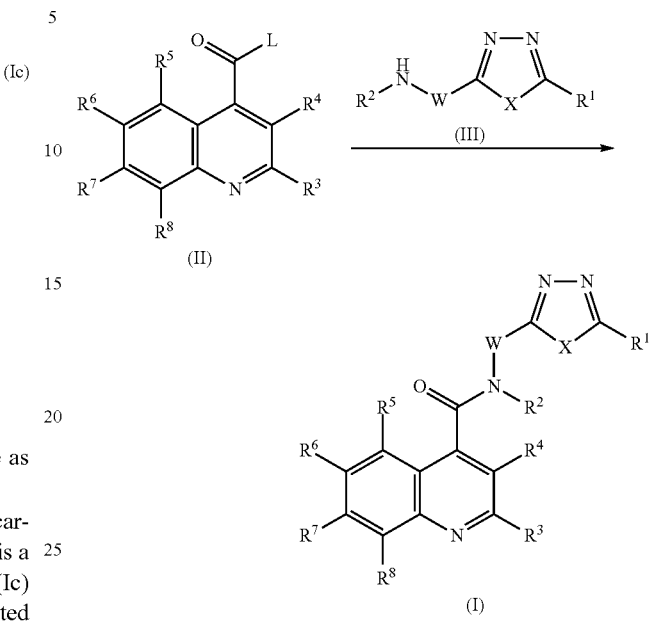

wherein L represents a leaving group, and W, X, and R$^1$ to R$^8$ are as defined above.

Examples of the leaving group defined as L include a halogen atom, a hydroxyl group, a substituted or unsubstituted alkoxy group, a substituted or unsubstituted aryloxy group, and a substituted or unsubstituted alkylcarbonyloxy group. The halogen atom is as defined above. The alkyl moieties of the alkoxy and alkylcarbonyloxy groups are as defined above in the alkyl group. Examples thereof include alkoxy and alkylcarbonyloxy groups having 1 to 12 carbon atoms. Moreover, the aryl moieties of the aryloxy and arylcarbonyloxy groups are as defined above in the aryl group. Examples thereof include aryloxy and arylcarbonyloxy groups having 6 to 12 carbon atoms. Examples of substituents include a halogen atom and a nitro group. The halogen atom is as defined above. Specific examples of the leaving group can include: alkoxy groups such as methoxy; aryloxy groups such as pentafluorophenoxy and 4-nitrophenoxy; and alkylcarbonyloxy groups such as pivaloyloxy.

The compound (I) can be obtained by reacting a compound (II) with a compound (III) at a temperature of −78° C. to the boiling point of a solvent used for 5 minutes to 48 hours in an appropriate inert solvent, for example, halogenated hydrocarbon (e.g., chloroform and dichloromethane), aromatic hydrocarbon (e.g., benzene and toluene), an ether solvent (e.g., diethyl ether, tetrahydrofuran (THF), and 1,4-dioxane), an aprotic polar solvent (e.g., N,N-dimethylformamide (DMF), N-methylpyrrolidone (NMP), and dimethyl sulfoxide (DMSO)), a basic solvent (e.g., pyridine and quinoline), or a mixed solvent thereof, in the presence of a base.

The present reaction requires a base, in some cases. In this case, examples of the base include: organic bases such as triethylamine and pyridine; inorganic bases such as potassium carbonate, potassium bicarbonate, tripotassium phosphate, sodium hydroxide, and sodium hydride; and metal alkoxides such as sodium methoxide and potassium tert-butoxide.

In the present reaction, a condensing agent may be allowed to coexist, particularly when L is a hydroxyl group. A condensing agent described in the paper, for example, a carbodiimide-type condensing agent (e.g., DCC and WSCI), a phosphonium-type condensing agent (e.g., BOP), a guanidium salt-type condensing agent (e.g., HATU), DMT-MM, CDI, or DPP-Cl can be used as the condensing agent.

The compounds (II) and (III) are commercially available or can be obtained according to a method described in documents, etc. (for the compound (II), J. Med. Chem., 1997, 40, 1794-1807; and for the compound (III), Tetrahedron Lett., 2006, 47, 4889-4891 and 2004, 45, 7157-7161), a method described in Production or Reference Examples, or an equivalent thereto.

Production Method 2

The compound (Ia) which is the compound (I) wherein $R^2$ represents a hydrogen atom, W represents a single bond, and X is an oxygen atom, and the compound (Ib) which is the compound (I) wherein W is a single bond, and X is a sulfur atom can also be produced according to the following reaction steps:

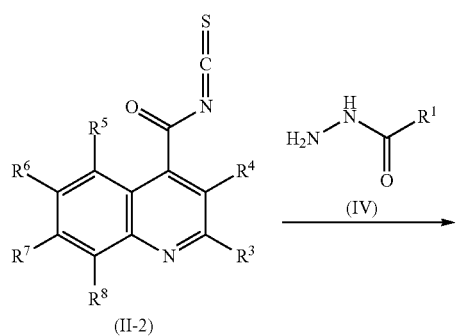

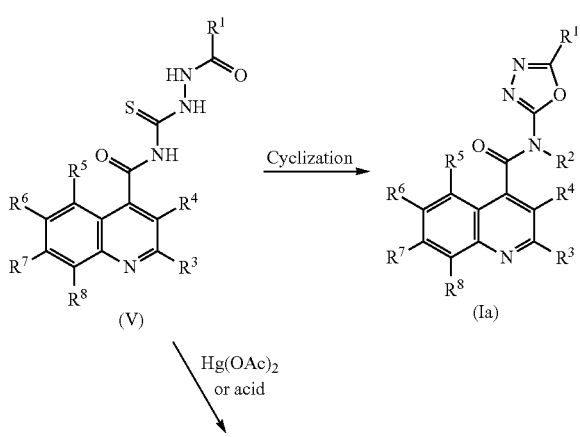

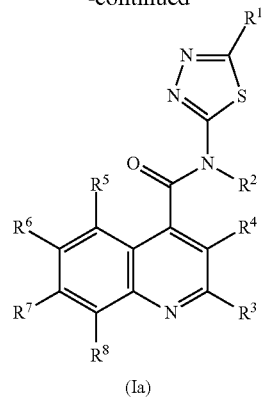

(Ia)

wherein $R^1$ to $R^8$ are as defined above.

The compound (Ia) can be obtained by converting a compound (II-2) and a compound (IV) to a compound (V) by condensation and then subjecting the compound (V) to annelation in the presence of alkylsulfonyl chloride, alkylsulfonic anhydride, arylsulfonyl chloride, or an oxidizing agent.

The alkyl moieties of the alkylsulfonyl chloride and the alkylsulfonic anhydride are as defined above in the alkyl group and include alkyl groups having 1 to 12 carbon atoms. Moreover, the aryl moiety of the arylsulfonyl chloride is as defined above in the aryl group and includes aryl groups having 6 to 12 carbon atoms. Examples of substituents include an alkyl group, a trifluoromethyl group, a halogen atom, and a nitro group. The alkyl group and the halogen atom are as defined above. Specific examples thereof can include methanesulfonyl chloride, trifluoromethanesulfonic anhydride, and toluenesulfonyl chloride.

Moreover, examples of the oxidizing agent can include iodine.

Moreover, the compound (Ib) can be obtained by subjecting the compound (V) to annelation in the presence of $Hg(OAc)_2$ or an acid catalyst.

In this case, examples of acids as the acid catalyst include: mineral acids such as hydrochloric acid, sulfuric acid, and phosphoric acid; organic acids such as acetic acid, methanesulfonic acid, trifluoromethanesulfonic acid, benzenesulfonic acid, and p-toluenesulfonic acid; and Lewis acids such as titanium tetrachloride, boron trifluoride, and aluminum chloride.

These reactions can be performed at a temperature of −78° C. to the boiling point of a solvent used for 5 minutes to 48 hours in an appropriate inert solvent, for example, halogenated hydrocarbon (e.g., chloroform and dichloromethane), aromatic hydrocarbon (e.g., benzene and toluene), an ether solvent (e.g., diethyl ether, tetrahydrofuran (THF), and 1,4-dioxane), an aprotic polar solvent (e.g., N,N-dimethylformamide (DMF), N-methylpyrrolidone (NMP), and dimethyl sulfoxide (DMSO)), a basic solvent (e.g., pyridine and quinoline), water, or a mixed solvent thereof.

The present reaction requires a base, in some cases. In this case, examples of the base include: organic bases such as triethylamine and pyridine; inorganic bases such as potassium carbonate, potassium bicarbonate, tripotassium phosphate, sodium hydroxide, and sodium hydride; and metal alkoxides such as sodium methoxide and potassium tert-butoxide.

The compounds (II-2) and (IV) are commercially available or can be produced according to, a routine method, a method described in documents (e.g., for the compound (II-2), the acyl isothiocyanate synthesis method described in The Chemical Society of Japan, ed., "Experimental Chemistry Guidebook 20, 4th ed., Organic Synthesis II", Maruzen Co. Ltd., July 1992, p. 488), a method described in Production or Reference Examples, or an equivalent thereto.

In each of these production methods, when the defined groups are altered under the conditions of the performed method or are inappropriate for performing the method, the compound of interest can be obtained using protective group introduction and elimination methods (see e.g., Protective Groups in Organic Synthesis, T. W. Greene, John Wiley & Sons Inc., 1981), etc., routinely used in organic synthetic chemistry. Moreover, the conversion of a functional group contained in each substituent can also be performed by a method known in the art (e.g., Comprehensive Organic Transformations, R. C. Larock, 1989), in addition to the production methods. Some compounds (I) can further be converted as synthesis intermediates to another derivative (I).

The intermediates and the compound of interest in each of the production methods can be isolated and purified by a purification method routinely used in organic synthetic chemistry, for example, neutralization, filtration, extraction, washing, drying, concentration, recrystallization, and various chromatography techniques. Moreover, the intermediates may be subjected to next reaction without being particularly purified.

Some compounds (I) can have isomers. In the present invention, all of possible isomers and their mixtures can be used as anticancer agents.

To obtain a salt of the compound (I), the compound (I) obtained in the form of a salt can be purified directly. Alternatively, the compound (I) obtained in a free form can be dissolved or suspended in an appropriate organic solvent to form a salt by a usual method by the addition of an acid or a base.

Moreover, the compound (I) and the pharmacologically acceptable salt thereof may be present in the form of adducts with water or various solvents. These adducts can also be used as the STAT5 inhibitor of the present invention.

Specific examples of the compound (I) obtained by the production methods are shown in Tables 1 to 16.

TABLE 1

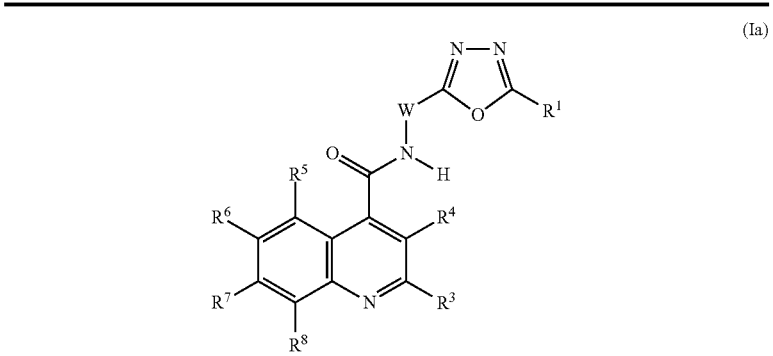

TABLE 1-continued (Ia) Structure: 1,3,4-oxadiazole (with R¹) — W — NH — C(=O) — quinoline (R³ at 2-position, R⁴ at 3-position, R⁵ at 5, R⁶ at 6, R⁷ at 7, R⁸ at 8)

| Compound No. | W | R¹ | R³ | R⁴ | R⁵ | R⁶ | R⁷ | R⁸ |
|---|---|---|---|---|---|---|---|---|
| Ia-7 | Single bond | 4-nitrophenyl | phenyl | H | H | H | H | H |
| Ia-8 | Single bond | pyridin-2-yl | phenyl | H | H | H | H | H |
| Ia-9 | Single bond | pyridin-3-yl | phenyl | H | H | H | H | H |
| Ia-10 | $CH_2$ | phenyl | phenyl | H | H | H | H | H |

TABLE 2

(Ia) Structure: 1,3,4-oxadiazole (with R¹) directly attached — NH — C(=O) — quinoline (R³ at 2, R⁴ at 3, R⁵ at 5, R⁶ at 6, R⁷ at 7, R⁸ at 8)

| Compound No. | R¹ | R³ | R⁴ | R⁵ | R⁶ | R⁷ | R⁸ |
|---|---|---|---|---|---|---|---|
| Ia-11 | furan-2-yl | H | H | H | H | H | H |
| Ia-12 | furan-2-yl | Cl | H | H | H | H | H |
| Ia-13 | furan-2-yl | Br | H | H | H | H | H |
| Ia-14 | furan-2-yl | piperidin-1-yl | H | H | H | H | H |
| Ia-15 | furan-2-yl | 3-hydroxyphenyl | H | H | H | H | H |

TABLE 2-continued (Ia) structure: 1,3,4-oxadiazole (with R¹) connected via NH-C(=O) to quinoline bearing R³-R⁸.

| Compound No. | R¹ | R³ | R⁴ | R⁵ | R⁶ | R⁷ | R⁸ |
|---|---|---|---|---|---|---|---|
| Ia-16 | 2-furyl | 3-nitrophenyl | H | H | H | H | H |
| Ia-17 | 2-furyl | 4-cyanophenyl | H | H | H | H | H |
| Ia-18 | 2-furyl | 2-furyl | H | H | H | H | H |
| Ia-19 | 2-furyl | 5-chloro-2-thienyl | H | H | H | H | H |

TABLE 3

(Ia)

| Compound No. | R¹ | R³ | R⁴ | R⁵ | R⁶ | R⁷ | R⁸ |
|---|---|---|---|---|---|---|---|
| Ia-20 | 2-furyl | 4-pyridyl | H | H | H | H | H |
| Ia-21 | 2-furyl | —CH=CH—CH=CH— | | H | H | H | H |
| Ia-22 | 2-furyl | phenyl | H | H | Cl | H | H |
| Ia-23 | 2-furyl | phenyl | H | H | OMe | H | H |
| Ia-24 | 2-furyl | phenyl | H | H | H | Br | H |
| Ia-25 | 2-furyl | phenyl | H | H | H | H | Me |
| Ia-26 | 2-furyl | phenyl | H | H | H | Cl | Me |
| Ia-27 | 2-furyl | 4-methylphenyl | H | H | H | H | Me |
| Ia-28 | 2-furyl | 2-furyl | H | H | H | Cl | Me |

TABLE 4

(Ia) Structure with R¹ on oxadiazole, amide linked to quinoline with R³-R⁸

| Compound No. | R¹ | R³ | R⁴ | R⁵ | R⁶ | R⁷ | R⁸ |
|---|---|---|---|---|---|---|---|
| Ia-29 | 2-furyl | 2-thienyl | H | H | Me | H | H |
| Ia-30 | 2-furyl | 2-thienyl | H | H | Cl | H | H |
| Ia-31 | 2-furyl | 2-thienyl | H | H | H | H | Me |
| Ia-32 | 2-furyl | 2-thienyl | H | H | H | H | Cl |
| Ia-33 | 2-furyl | 2-thienyl | H | H | Me | H | Me |
| Ia-34 | 2-furyl | OH | H | H | H | H | H |
| Ia-35 | 2-furyl | On—Bu | H | H | H | H | H |
| Ia-36 | 2-furyl | 2-F-phenyl | H | H | H | H | H |
| Ia-37 | 2-furyl | 2-Cl-phenyl | H | H | H | H | H |
| Ia-38 | 2-furyl | 2-HO-phenyl | H | H | H | H | H |

TABLE 5

(Ia) Structure with 2-furyl on oxadiazole, amide linked to quinoline with R³-R⁸

| Compound No. | R³ | R⁴ | R⁵ | R⁶ | R⁷ | R⁸ |
|---|---|---|---|---|---|---|
| Ia-39 | 2-O₂N-phenyl | H | H | H | H | H |
| Ia-40 | 2-H₂N-phenyl | H | H | H | H | H |
| Ia-41 | 3-Cl-phenyl | H | H | H | H | H |
| Ia-42 | 3-MeO-phenyl | H | H | H | H | H |
| Ia-43 | 3-CN-phenyl | H | H | H | H | H |
| Ia-44 | 3-(COOt-Bu)-phenyl | H | H | H | H | H |
| Ia-45 | 3-COOH-phenyl | H | H | H | H | H |
| Ia-46 | 4-F-phenyl | H | H | H | H | H |

TABLE 6

Structure (Ia): quinoline with R3-R8 substituents, C(=O)-NH linked to 1,3,4-oxadiazole-furan

| Compound No. | R³ | R⁴ | R⁵ | R⁶ | R⁷ | R⁸ |
|---|---|---|---|---|---|---|
| Ia-47 | 4-Cl-C₆H₄- | H | H | H | H | H |
| Ia-48 | 4-Me-C₆H₄- | H | H | H | H | H |
| Ia-49 | 4-OCHF₂-C₆H₄- | H | H | H | H | H |
| Ia-50 | 4-OH-C₆H₄- | H | H | H | H | H |
| Ia-51 | 4-OMe-C₆H₄- | H | H | H | H | H |
| Ia-52 | 4-NO₂-C₆H₄- | H | H | H | H | H |
| Ia-53 | 4-COOt-Bu-C₆H₄- | H | H | H | H | H |
| Ia-54 | 4-COOH-C₆H₄- | H | H | H | H | H |
| Ia-55 | 4-SO₂NH₂-C₆H₄- | H | H | H | H | H |
| Ia-56 | 2,4-di-Me-C₆H₃- | H | H | H | H | H |
| Ia-57 | 2,4-di-OMe-C₆H₃- | H | H | H | H | H |

TABLE 7

Structure (Ia): same scaffold

| Compound No. | R³ | R⁴ | R⁵ | R⁶ | R⁷ | R⁸ |
|---|---|---|---|---|---|---|
| Ia-58 | benzo[1,3]dioxol-5-yl | H | H | H | H | H |
| Ia-59 | cyclopropyl | H | H | H | H | H |
| Ia-60 | naphthalen-1-yl | H | H | H | H | H |
| Ia-61 | 6-OMe-naphthalen-2-yl | H | H | H | H | H |
| Ia-62 | pyridin-2-yl | H | H | H | H | H |
| Ia-63 | pyridin-3-yl | H | H | H | H | H |
| Ia-64 | 5-Me-furan-2-yl | H | H | H | H | H |
| Ia-65 | (E)-styryl (-CH=CH-Ph) | H | H | H | H | H |
| Ia-66 | phenyl | Me | H | H | H | H |
| Ia-67 | phenyl | H | H | F | H | H |

TABLE 8

(Ia)

| Compound No. | R³ | R⁴ | R⁵ | R⁶ | R⁷ | R⁸ |
|---|---|---|---|---|---|---|
| Ia-68 | phenyl | H | H | Br | H | H |
| Ia-69 | phenyl | H | H | I | H | H |
| Ia-70 | phenyl | H | H | Me | H | H |
| Ia-71 | phenyl | H | H | OCF₃ | H | H |
| Ia-72 | phenyl | H | H | H | Cl | H |
| Ia-73 | phenyl | H | H | H | H | Cl |
| Ia-74 | phenyl | H | H | Cl | H | Cl |
| Ia-75 | phenyl | H | H | phenyl | H | H |
| Ia-76 | phenyl | H | H | 4-pyridyl | H | H |
| Ia-77 | 4-chlorophenyl | H | H | Cl | H | H |
| Ia-78 | 5-methylthiophen-2-yl | H | H | Br | H | H |
| Ia-79 | furan-2-yl | H | H | H | H | Cl |

TABLE 9

(Ia)

| Compound No. | R¹ | R³ | R⁴ | R⁵ | R⁶ | R⁷ | R⁸ |
|---|---|---|---|---|---|---|---|
| Ia-80 | furan-2-yl | phenyl | H | H | H | Me | H |
| Ia-81 | Me | H | H | H | H | H | H |
| Ia-82 | Et | H | H | H | H | H | H |

TABLE 9-continued
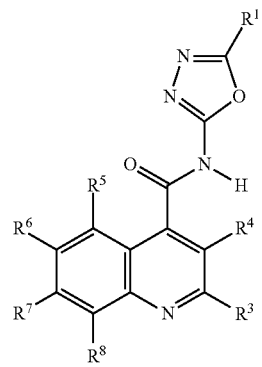
(Ia)
| Compound No. | R¹ | R³ | R⁴ | R⁵ | R⁶ | R⁷ | R⁸ |
|---|---|---|---|---|---|---|---|
| Ia-83 | 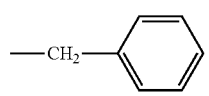 | H | H | H | H | H | H |
| Ia-84 | 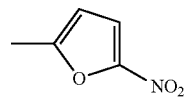 | H | H | H | H | H | H |
| Ia-85 | COOEt | H | H | H | H | H | H |
| Ia-86 | 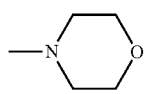 | H | H | H | H | H | H |
| Ia-87 | 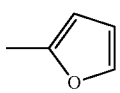 | 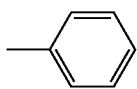 | H | H | OH | H | H |
| Ia-88 | 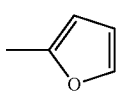 | 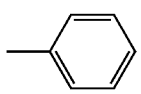 | H | H | OCH₂CH₂NMe₂ | H | H |
| Ia-89 | 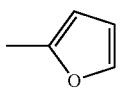 | 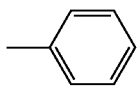 | H | H | OCH₂CH₂OMe | H | H |

TABLE 10

(Ia) Structure with R³–R⁸ substituents on quinoline-carboxamide-oxadiazole-furan scaffold.

| Compound No. | R³ | R⁴ | R⁵ | R⁶ | R⁷ | R⁸ |
|---|---|---|---|---|---|---|
| Ia-90 | phenyl | H | H | OCH₂-phenyl | H | H |
| Ia-91 | phenyl | H | H | OCOCH₃ | H | H |
| Ia-92 | phenyl | H | H | NHCOCH₃ | H | H |
| Ia-93 | phenyl | H | H | NHCOC₂H₅ | H | H |
| Ia-94 | phenyl | H | H | NHCOC₃H₇ | H | H |
| Ia-95 | phenyl | H | H | CN | H | H |
| Ia-96 | phenyl | H | H | 2-F-phenyl | H | H |
| Ia-97 | phenyl | H | H | 4-F-phenyl | H | H |
| Ia-98 | phenyl | H | H | 4-OH-phenyl | H | H |
| Ia-99 | phenyl | H | H | 3-thienyl | H | H |
| Ia-100 | phenyl | H | H | 3-pyridyl | H | H |

TABLE 10-continued

| Compound No. | R³ | R⁴ | R⁵ | R⁶ | R⁷ | R⁸ |
|---|---|---|---|---|---|---|
| Ia-101 | 2-(AcHN)-phenyl | H | H | H | H | H |

TABLE 11

(Ia)

| Compound No. | R³ | R⁴ | R⁵ | R⁶ | R⁷ | R⁸ |
|---|---|---|---|---|---|---|
| Ia-102 | 2-(MeO₂SHN)-phenyl | H | H | H | H | H |
| Ia-103 | 4-NH₂-phenyl | H | H | H | H | H |
| Ia-104 | 4-Ac-phenyl | H | H | H | H | H |
| Ia-105 | 4-SMe-phenyl | H | H | H | H | H |
| Ia-106 | 4-SO₂Me-phenyl | H | H | H | H | H |
| Ia-107 | 2-thienyl | H | H | H | H | H |

TABLE 11-continued (Ia structure with furan-oxadiazole)

| Compound No. | R³ | R⁴ | R⁵ | R⁶ | R⁷ | R⁸ |
|---|---|---|---|---|---|---|
| Ia-108 | 2,5-dimethylthiophene (Me-thiophene-) | H | Me | H | Me | H |
| Ia-109 | 5-ethyl-2-thienyl (Et-thiophene-) | H | Me | H | Me | H |

TABLE 12

(Ia)

| Compound No. | R¹ | R⁴ | R⁵ | R⁶ | R⁷ | R⁸ |
|---|---|---|---|---|---|---|
| Ia-110 | phenyl | H | H | Cl | H | H |
| Ia-111 | phenyl | H | H | OCF₃ | H | H |
| Ia-112 | 2-methylphenyl | Cl | H | H | Cl | H |
| Ia-113 | 2-methylphenyl | Cl | H | H | OCF₃ | H |
| Ia-114 | 4-chlorophenyl | H | H | Cl | H | H |
| Ia-115 | 4-chlorophenyl | H | H | OCF₃ | H | H |
| Ia-116 | 4-methoxyphenyl | H | H | Cl | H | H |
| Ia-117 | 4-methoxyphenyl | H | H | OCF₃ | H | H |
| Ia-118 | 4-nitrophenyl | H | H | Cl | H | H |

TABLE 13

(Ia)

| Compound No. | R¹ | R⁴ | R⁵ | R⁶ | R⁷ | R⁸ |
|---|---|---|---|---|---|---|
| Ia-119 | 4-nitrophenyl | H | H | OCF₃ | H | H |

TABLE 13-continued

Structure (Ia): 5-R¹-1,3,4-oxadiazol-2-yl amide of 2-phenylquinoline-4-carboxamide with substituents R⁴, R⁵, R⁶, R⁷, R⁸ on the quinoline.

| Compound No. | R¹ | R⁴ | R⁵ | R⁶ | R⁷ | R⁸ |
|---|---|---|---|---|---|---|
| Ia-120 | 3-furyl | H | H | OCF₃ | H | H |
| Ia-121 | 2-thienyl | H | H | Cl | H | H |
| Ia-122 | 2-thienyl | H | H | OCF₃ | H | H |
| Ia-123 | 2,3-dimethyl-furan-yl (3-Me-2-furyl) | H | H | H | H | H |
| Ia-124 | 5-Me-2-furyl | H | H | H | H | H |
| Ia-125 | 3,5-dimethyl-2-furyl | H | H | H | H | H |
| Ia-126 | 2-benzofuranyl | H | H | H | H | H |

TABLE 14

Structure (Ia) with N–R² amide.

| Compound No. | R¹ | R² | R⁴ | R⁵ | R⁶ | R⁷ | R⁸ |
|---|---|---|---|---|---|---|---|
| Ia-127 | 4-Me-thiazol-2-yl (2-Me) | H | H | H | H | H | H |
| Ia-128 | 2,4-dimethyl-thiazol-5-yl (4-Me, 2-Me) | H | H | H | H | H | H |
| Ia-129 | 3-OMe-phenyl | H | H | H | H | H | H |
| Ia-130 | CH₂CN | H | H | H | H | H | H |
| Ia-131 | 2-furyl | Me | H | H | H | H | H |
| Ia-132 | tetrahydrofuran-2-yl | H | H | H | H | H | H |

TABLE 15

Structure (Ib): 1,3,4-thiadiazole (with R¹ at 5-position) linked via NH-C(=O) to a quinoline at the 4-position, with R³ at 2-position, R⁴ at 3-position, R⁵ at 5-position, R⁶ at 6-position, R⁷ at 7-position, R⁸ at 8-position.

| Compound No. | R¹ | R³ | R⁴ | R⁵ | R⁶ | R⁷ | R⁸ |
|---|---|---|---|---|---|---|---|
| Ib-1 | H | phenyl | H | H | H | H | H |
| Ib-2 | Br | phenyl | H | H | H | H | H |
| Ib-3 | phenyl | phenyl | H | H | H | H | H |
| Ib-4 | 2-furyl | phenyl | H | H | H | H | H |
| Ib-5 | 4-pyridyl | phenyl | H | H | H | H | H |
| Ib-6 | tetrahydrofuran-2-yl | phenyl | H | H | H | H | H |
| Ib-7 | 4-pyridyl | H | H | H | Cl | H | H |
| Ib-8 | 4-pyridyl | H | H | H | OCF₃ | H | H |
| Ib-9 | 2-furyl | H | H | H | Cl | H | H |
| Ib-10 | 2-furyl | H | H | H | OCF₃ | H | H |

TABLE 16

Structure (Ic): 1,2,4-triazole (with R¹) linked via W and NH-C(=O) to a quinoline at the 4-position, with R³ at 2-position, R⁴ at 3-position, R⁵ at 5-position, R⁶ at 6-position, R⁷ at 7-position, R⁸ at 8-position.

| Compound No. | W | R¹ | R³ | R⁴ | R⁵ | R⁶ | R⁷ | R⁸ |
|---|---|---|---|---|---|---|---|---|
| Ic-1 | Single bond | H | phenyl | H | H | H | H | H |
| Ic-2 | CH₂ | phenyl | phenyl | H | H | H | H | H |

Moreover, the names and structural formulas of commercially available compounds are exemplified below.

2-phenyl-N-[5-(2-thienyl)-1,3,4-oxadiazol-2-yl]-4-quinolinecarboxamide (Ia-a)

N-[5-(5-chloro-2-thienyl)-1,3,4-oxadiazol-2-yl]-2-phenyl-4-quinolinecarboxamide (Ia-b)

N-[5-(2-methoxyphenyl)-1,3,4-oxadiazol-2-yl]-2-phenyl-4-quinolinecarboxamide (Ia-c)

N-[5-(4-methoxyphenyl)-1,3,4-oxadiazol-2-yl]-2-phenyl-4-quinolinecarboxamide (Ia-d)

N-[5-(2-chlorophenyl)-1,3,4-oxadiazol-2-yl]-2-phenyl-4-quinolinecarboxamide (Ia-e)

N-[5-(2,5-dichlorophenyl)-1,3,4-oxadiazol-2-yl]-2-phenyl-4-quinolinecarboxamide (Ia-f)

N-[5-(3,4-ethylenedioxyphenyl)-1,3,4-oxadiazol-2-yl]-2-phenyl-4-quinolinecarboxamide (Ia-g)

N-[5-(4-methoxyphenyl)-1,3,4-oxadiazol-2-yl]-2-(2-thienyl)-4-quinolinecarboxamide (Ia-h)

N-(5-phenyl-1,3,4-oxadiazol-2-yl)-2-(4-tolyl)-4-quinolinecarboxamide (Ia-i)

N-(5-phenyl-1,3,4-oxadiazol-2-yl)-2-(2-thienyl)-4-quinolinecarboxamide (Ia-j)

TABLE 17
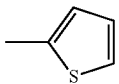
(Ia)
| Compound No. | R¹ | R³ | R⁴ | R⁵ | R⁶ | R⁷ | R⁸ |
|---|---|---|---|---|---|---|---|
| Ia-a | 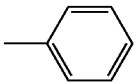 | 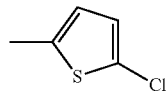 | H | H | H | H | H |
| Ia-b | 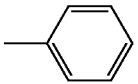 | 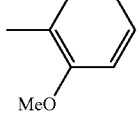 | H | H | H | H | H |
| Ia-c | 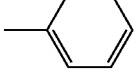 | 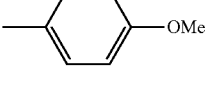 | H | H | H | H | H |
| Ia-d | 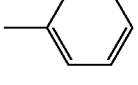 | 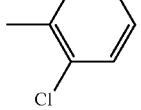 | H | H | H | H | H |
| Ia-e | 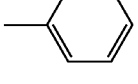 | 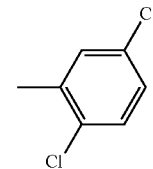 | H | H | H | H | H |
| Ia-f | 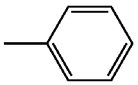 | 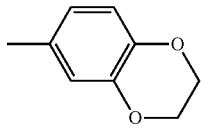 | H | H | H | H | H |
| Ia-g | 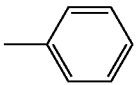 | 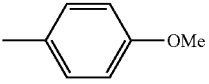 | H | H | H | H | H |
| Ia-h | 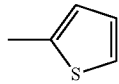 | 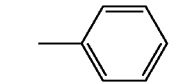 | H | H | H | H | H |
| Ia-i | 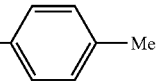 | 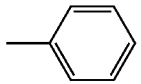 | H | H | H | H | H |
| Ia-j | 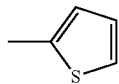 | | H | H | H | H | H |

2-phenyl-N-[5-(3-pyridyl)-1,3,4-thiadiazol-2-yl]-4-quinolinecarboxamide (Ib-a)
2-(3-isopropoxyphenyl)-N-[5-(4-pyridyl)-1,3,4-thiadiazol-2-yl]-4-quinolinecarboxamide (Ib-b)
2-(2,5-dimethoxyphenyl)-N-[5-(4-pyridyl)-1,3,4-thiadiazol-2-yl]-4-quinolinecarboxamide (Ib-c)
6-chloro-2-(3-pyridyl)-N-[5-(4-pyridyl)-1,3,4-thiadiazol-2-yl]-4-quinolinecarboxamide (Ib-d)
2-(5-methyl-2-furyl)-N-[5-(4-pyridyl)-1,3,4-thiadiazol-2-yl]-4-quinolinecarboxamide (Ib-e)
6-chloro-2-(2,5-dimethyl-3-thienyl)-N-[5-(4-pyridyl)-1,3,4-thiadiazol-2-yl]-4-quinolinecarboxamide (Ib-f)

TABLE 18

(Ib)

| Compound No. | $R^1$ | $R^3$ | $R^4$ | $R^5$ | $R^6$ | $R^7$ | $R^8$ |
|---|---|---|---|---|---|---|---|
| Ib-a | 3-pyridyl | phenyl | H | H | H | H | H |
| Ib-b | 4-pyridyl | 3-OiPr-phenyl | H | H | H | H | H |
| Ib-c | 4-pyridyl | 2,5-diMeO-phenyl | H | H | H | H | H |
| Ib-d | 4-pyridyl | 3-pyridyl | H | H | Cl | H | H |
| Ib-e | 4-pyridyl | 5-Me-2-furyl | H | H | H | H | H |
| Ib-f | 4-pyridyl | 2,5-diMe-3-thienyl | H | H | Cl | H | H |

The compound (I) or the pharmacologically acceptable salt thereof may directly be administered alone and is usually preferably made into various pharmaceutical preparations. The pharmaceutical preparations can be produced by a routine method of pharmaceutics by mixing the active ingredient with one or two or more pharmacologically acceptable carriers.

Examples of an administration route include oral or inhalation administration and parenteral administration such as intravenous administration.

Examples of a dosage form include tablets and injections. The tablets can be produced according to a routine method by mixing various additives, for example, lactose, starch, magnesium stearate, hydroxypropylcellulose, polyvinyl alcohol, a surfactant, and glycerin. The inhalants can be produced according to a routine method by adding, for example, lactose. The injections can be produced according to a routine method by adding water, saline, plant oil, a solubilizing agent, a preservative, and the like.

The effective amount of the compound (I) or the pharmacologically acceptable salt thereof and the number of doses thereof differ depending on a dosage form, the age, body weight, and condition of a patient, etc. Usually, 0.001 mg to 5 g, preferably 0.1 mg to 1 g, more preferably 1 to 500 mg is administered once a day or in several divided portions per day to one adult.

Hereinafter, the present invention will be described more specifically with reference to Examples. However, the technical scope of the present invention is not limited to these examples.

Example 1

STAT3 Transcription Inhibition Test

The inhibition of STAT3 transcription was evaluated by using STAT3 reporter HeLa stable cell line (Panomics Inc., catalog No. RC0003), a cell line for the reporter gene method, and performing the following method according to the appendix included therein.

STAT3 reporter HeLa stable cell line subcultured and maintained in a Dulbecco's modified Eagle's medium (DMEM) containing 10% fetal bovine serum, 100 units/mL penicillin, and 100 µg/mL streptomycin was inoculated at a concentration of 40000 cells/well to a 96-well plate (white) and attached to the plate by overnight incubation at 37° C. under 5% $CO_2$. After addition of each evaluation compound adjusted to various concentrations (adjusted with a DMSO solution), the cells were precultured for 1 hour. Then, oncostatin M for activating STAT3 was added at a final concentration 10 ng/mL, and the cells were further cultured at 37° C. under 5% $CO_2$ for 4 hours. Luciferase activity derived from the cells was determined using Steady-Glo Luciferase Assay System (Promega Corp.), and STAT3 transcriptional activity scores were calculated according to the following formula:

STAT3 transcriptional activity score (%)=100×($L_{chem}$−$L_0$)/($L_{DMSO}$−$L_0$)

$L_o$: luminescence intensity obtained without stimulation with oncostatin M
$L_{chem}$: luminescence intensity obtained by the addition of a test sample
$L_{DMSO}$: luminescence intensity obtained by the addition of only a solvent for dissolving a test sample The test results were indicated in the rate of inhibition of STAT3 transcription by each compound at a concentration of 100 µM. The results are shown in Tables 19 and 20.

TABLE 19

| Compound No. | STAT3 transcription inhibitory activity (%) | Compound No. | STAT3 transcription inhibitory activity (%) |
|---|---|---|---|
| Ia-1 | 54 | Ia-2 | >100 |
| Ia-3 | >100 | Ia-5 | >100 |
| Ia-7 | 65 | Ia-9 | 65 |
| Ia-10 | >100 | Ia-14 | 63 |
| Ia-16 | 62 | Ia-17 | 80 |
| Ia-18 | 68 | Ia-19 | 77 |
| Ia-22 | 76 | Ia-23 | 100 |
| Ia-24 | 72 | Ia-25 | 77 |
| Ia-26 | 73 | Ia-27 | 71 |
| Ia-28 | >100 | Ia-29 | 65 |
| Ia-30 | 62 | Ia-32 | 90 |
| Ia-33 | 58 | Ia-35 | 57 |
| Ia-37 | 100 | Ia-38 | >100 |
| Ia-40 | 62 | Ia-41 | >100 |
| Ia-42 | 92 | Ia-43 | 71 |
| Ia-44 | >100 | Ia-46 | 80 |

TABLE 20

| Compound No. | STAT3 transcription inhibitory activity (%) | Compound No. | STAT3 transcription inhibitory activity (%) |
|---|---|---|---|
| Ia-47 | >100 | Ia-48 | 92 |
| Ia-49 | >100 | Ia-50 | 73 |
| Ia-51 | >100 | Ia-52 | >100 |
| Ia-53 | >100 | Ia-56 | 99 |
| Ia-57 | >100 | Ia-58 | >100 |
| Ia-60 | >100 | Ia-61 | >100 |
| Ia-64 | >100 | Ia-65 | >100 |
| Ia-67 | 90 | Ia-68 | >100 |
| Ia-70 | >100 | Ia-71 | >100 |
| Ia-72 | >100 | Ia-74 | 97 |
| Ia-75 | >100 | Ia-76 | >100 |
| Ia-79 | >100 | Ia-83 | >100 |
| Ia-84 | 56 | Ia-88 | 76 |
| Ia-89 | >100 | Ia-90 | >100 |
| Ia-93 | 72 | Ia-94 | 89 |
| Ia-98 | >100 | Ia-99 | 73 |
| Ia-100 | 92 | Ia-110 | 89 |
| Ia-111 | >100 | Ia-112 | >100 |
| Ia-113 | >100 | Ia-117 | 87 |
| Ib-2 | >100 | Ib-4 | 58 |
| Ib-8 | 65 | Ia-a | 86 |
| Ia-c | 67 | Ia-i | 85 |
| Ia-j | 91 | Ib-b | >100 |
| Ib-c | >100 | Ib-d | 73 |
| Ib-e | 85 | Ib-f | 100 |

Example 2

MDA-MB-435S Cell Growth Inhibitory Activity

MDA-MB-435S diluted with phenol red-free RPMI1640 (GIBCO; 10% FBS, 20 units/ml penicillin/streptomycin) was inoculated at a concentration of 2000 cells/well to a 96-well plate (Greiner Bio-One) and cultured overnight at 37° C. in the presence of 5% $CO_2$. Then, a test sample solution (containing 2 (v/v) % DMSO) adjusted to 10 μM was added thereto at a concentration of 10 μL/well and contacted with the cells at 37° C. for 72 hours in the presence of 5% $CO_2$. Each well was washed three times with a medium. Then, after addition of 100 μL/well of a medium and 20 μL/well of CellTiter 96 AQ$_{ueous}$ One Solution Reagent (Promega Corp.), the cells were incubated at 37° C. for 2 hours in the presence of 5% $CO_2$. Absorbance at 495 nm was measured using Multiplate reader (Molecular Devices, Inc.), and the rate of inhibition of cell growth was calculated according to the following formula:

Rate of inhibition of cell growth (%)=100-100× (Abs$_{chem}$−bkgd)/(Abs$_{DMSO}$−bkgd)

Abs$_{chem}$: absorbance obtained by the addition of a test sample

Abs$_{DMSO}$: absorbance obtained by the addition of only a solvent for test sample dissolution bkgd: absorbance obtained by the addition of CellTiter 96 AQ$_{ueous}$ One Solution Reagent to a medium for cell culture The test results were indicated in the rate of inhibition of cell growth by each compound at a concentration of 20 μM. The results are shown in Tables 21 and 22.

TABLE 21

| Compound No. | Cell growth inhibitory activity (%) | Compound No. | Cell growth inhibitory activity (%) |
|---|---|---|---|
| Ia-1 | 89 | Ia-3 | 53 |
| Ia-17 | 54 | Ia-19 | 98 |
| Ia-22 | 98 | Ia-23 | 50 |
| Ia-24 | 94 | Ia-27 | 99 |
| Ia-29 | 98 | Ia-30 | >100 |
| Ia-33 | 79 | Ia-38 | 50 |
| Ia-41 | 55 | Ia-42 | 92 |
| Ia-43 | 72 | Ia-44 | 99 |
| Ia-46 | 54 | Ia-47 | 82 |
| Ia-48 | 69 | Ia-49 | 51 |
| Ia-51 | 56 | Ia-52 | 68 |

TABLE 22

| Compound No. | Cell growth inhibitory activity (%) | Compound No. | Cell growth inhibitory activity (%) |
|---|---|---|---|
| Ia-53 | 100 | Ia-57 | 64 |
| Ia-58 | 58 | Ia-60 | 100 |
| Ia-64 | 57 | Ia-65 | 69 |
| Ia-68 | 63 | Ia-70 | >100 |
| Ia-71 | 85 | Ia-74 | 82 |
| Ia-75 | 64 | Ia-76 | 84 |
| Ia-83 | 90 | Ia-93 | 67 |
| Ia-98 | 86 | Ia-99 | 93 |
| Ia-100 | 76 | Ia-110 | 65 |
| Ia-111 | 87 | Ia-112 | 69 |
| Ia-113 | 76 | Ia-117 | 85 |
| Ib-2 | 79 | Ib-8 | 80 |
| Ia-a | 89 | Ia-c | 97 |
| Ib-b | 97 | | |

Example 3

SCC-3 Cell Growth Inhibition Test

Human lymphoma SCC-3 cells purchased from Japan Health Sciences Foundation were cultured for 4 days at a density of 5000 cells/well in a 96-well plate with RPMI1640 (Sigma-Aldrich Corp.) containing 10% fetal bovine serum (FBS; GIBCO) as a culture medium.

Simultaneously with cell inoculation, each test compound diluted to various concentrations with an RPMI medium was added to each well. After 72-hour culture, cell growth inhibitory activity was determined by the MTT method (J. Immunol. Methods, 1993, 65, 581-593) using a microplate reader (NJ-2300, BioTek Instruments, Inc.).

The test results were indicated in a concentration (IC$_{50}$) at which 50% cell growth was inhibited.

The results are shown in Table 23.

TABLE 23

| Compound No. | Cell growth inhibitory activity (IC$_{50}$: μM) | Compound No. | Cell growth inhibitory activity (IC$_{50}$: μM) |
|---|---|---|---|
| Ia-1  | 5.9 | Ia-17 | 4.6 |
| Ia-19 | 2.1 | Ia-22 | 0.9 |
| Ia-24 | 1.9 | Ia-25 | 6.0 |
| Ia-33 | 1.3 | Ia-35 | 5.6 |
| Ia-44 | 1.8 | Ia-47 | 2.0 |
| Ia-52 | 2.2 | Ia-53 | 0.7 |
| Ia-60 | 2.1 | Ia-65 | 2.6 |
| Ia-67 | 2.1 | Ia-70 | 1.9 |
| Ia-71 | 0.3 | Ia-72 | 2.2 |
| Ia-74 | 0.7 | Ia-i  | 2.7 |

Example 4

Evaluation Using Human Lymphoma-Transplanted Nude Mice $1 \times 10^6$ human lymphoma SCC-3 cells (containing Matrigel) were subcutaneously transplanted to the flank part of each 6-week-old male nude mouse (BALB/cA-nu/nu, CLEA Japan, Inc.). After the transplantation, the tumor volumes [major axis (mm) and minor axis (mm)] of the SCC-3 cancer-bearing mice were measured using an electronic vernier caliper (CD-10, Mitutoyo Corp.), and tumor volumes [mm$^3$: (major axis)$_x$(minor axis)$^2$/2] were calculated. SCC-3 cancer-bearing mice whose tumor volume reached 50 to 300 mm$^3$ were selected and divided based on the tumor volumes into groups each containing 5 individuals. A test compound was suspended in a 0.5% methylcellulose solution and orally administered at a dose of 0.01 mL/g body weight once a day for 5 days (Day 0 (administration initiation day) to Day 4). To a control group, none was administered. The tumor volumes of the SCC-3 cancer-bearing mice were measured every day from the initiation of test compound administration to evaluate antitumor effect. The antitumor effect was assessed by calculating T/C (%) values according to the following formula:
V: tumor volume on every assay day
V0: tumor volume on the administration initiation day (V/V0 of the test compound group)/(V/V0 of the control group)×100
Validity determination criteria for this system adopted the method of Inaba, et al. (Cancer, 1989, 64, 1577-1582). The results are shown in Table 24.

TABLE 24

| Compound No. | Amount/dose (mg/kg) | T/C (%) | The number of deaths |
|---|---|---|---|
| Control group |     | 100 | 0/5 |
| Ia-1  | 40  | 38  | 0/5 |
| Ia-1  | 160 | 40  | 0/5 |
| Ia-22 | 40  | 56  | 0/5 |

Production Example 1

N-[5-(2-furyl)-1,3,4-oxadiazol-2-yl]-2-phenyl-4-quinolinecarboxamide (compound Ia-1)

2-phenyl-4-quinolinecarbonyl chloride was synthesized from commercially available 2-phenyl-4-quinolinecarboxylic acid and thionyl chloride according to a routine method. 2-phenyl-4-quinolinecarbonyl chloride (2.00 g, 7.47 mmol) was added in small portions to a pyridine (40 mL) solution of commercially available 2-amino-5-(2-furyl)-1,3,4-oxadiazole (1.69 g, 11.2 mmol), and the mixture was heated with stirring at 60° C. for 6 hours. To the reaction solution, methanol was added, and the solvent was distilled off. The obtained residue was triturated by the addition of water. The deposited crystal was collected by filtration, washed with methanol and then with ethyl acetate, and then recrystallized from DMF-methanol to obtain the title compound (1.23 g, 3.22 mmol) as a light brown powder (yield: 43%).
$^1$H-NMR (DMSO-d$_6$) δ: 12.87 (1H, brs), 8.51 (1H, s), 8.37 (2H, d, J=7.3 Hz), 8.28 (1H, d, J=8.3 Hz), 8.21 (1H, d, J=8.5 Hz), 8.09 (1H, t, J=1.0 Hz), 7.89 (1H, dd, J=8.3 Hz, 7.1 Hz), 7.72 (1H, dd, J=8.0 Hz, 7.3 Hz), 7.63-7.54 (3H, m), 7.33 (1H, d, J=3.7 Hz), 6.83 (1H, dd, J=3.7 Hz, 1.7 Hz).
ES-MS (m/z): 383 (M+H)$^+$.

The following compounds Ia-2 to Ia-14 were synthesized according to the method of Production Example 1 using corresponding carboxylic acid and commercially available amine instead of 2-phenyl-4-quinolinecarboxylic acid and 2-amino-5-(2-furyl)-1,3,4-oxadiazole.

Production Example 2

N-[5-(3-furyl)-1,3,4-oxadiazol-2-yl]-2-phenyl-4-quinolinecarboxamide (compound Ia-2)

$^1$H-NMR (DMSO-d$_6$) δ: 8.51 (1H, s), 8.48 (1H, s), 8.36 (2H, d, J=7.4 Hz), 8.33 (1H, d, J=7.4 Hz), 8.19 (1H, d, J=8.5 Hz), 7.97 (1H, s), 7.88 (1H, dd, J=8.5 Hz, 7.4 Hz), 7.71 (1H, dd, J=7.4 Hz, 7.4 Hz), 7.63-7.54 (3H, m), 7.01 (1H, s).
ES-MS (m/z): 383 (M+H)$^+$.

Production Example 3

2-phenyl-N-(5-phenyl-1,3,4-oxadiazol-2-yl)-4-quinolinecarboxamide (compound Ia-3)

$^1$H-NMR (DMSO-d$_6$) δ: 12.83 (1H, br), 8.49 (1H, s), 8.37 (2H, d, J=7.3 Hz), 8.32 (1H, d, J=8.3 Hz), 8.20 (1H, d, J=8.3 Hz), 7.99 (2H, d, J=7.3 Hz), 7.88 (1H, t, J=7.3 Hz), 7.71 (1H, t, J=7.3 Hz), 7.64-7.55 (6H, m).
ES-MS (m/z): 393 (M+H)$^+$.

Production Example 4

N-[5-(2-chlorophenyl)-1,3,4-oxadiazol-2-yl]-2-phenyl-4-quinolinecarboxamide (compound Ia-4)

ES-MS (m/z): 429 ($^{37}$ClM+H)$^+$, 427 ($^{35}$ClM+H)$^+$.

Production Example 5

N-[5-(4-chlorophenyl)-1,3,4-oxadiazol-2-yl]-2-phenyl-4-quinolinecarboxamide (compound Ia-5)

ES-MS (m/z): 429 ($^{37}$ClM+H)$^+$, 427 ($^{35}$ClM+H)$^+$.

Production Example 6

N-[5-(4-methoxyphenyl)-1,3,4-oxadiazol-2-yl]-2-phenyl-4-quinolinecarboxamide (compound Ia-6)

ES-MS (m/z): 423 (M+H)$^+$.

Production Example 7

N-[5-(4-nitrophenyl)-1,3,4-oxadiazol-2-yl]-2-phenyl-4-quinolinecarboxamide (compound Ia-7)

$^1$H-NMR (DMSO-d$_6$) δ: 8.43 (1H, s), 8.37-8.32 (3H, m), 8.24 (2H, d, J=7.3 Hz), 8.16 (2H, d, J=8.8 Hz), 8.10 (1H, d, J=7.8 Hz), 8.02 (1H, d, J=8.8 Hz), 7.76 (1H, m), 7.57-7.48 (3H, m).
ES-MS (m/z): 438 (M+H)$^+$.

Production Example 8

2-phenyl-N-[5-(2-pyridyl)-1,3,4-oxadiazol-2-yl]-4-quinolinecarboxamide (compound Ia-8)

$^1$H-NMR (DMSO-d$_6$) δ: 8.79 (1H, d, J=4.6 Hz), 8.51 (1H, s), 8.38-8.36 (3H, m), 8.21-8.18 (2H, m), 8.08 (1H, t, J=7.8 Hz), 7.88 (1H, t, J=8.3 Hz), 7.72 (1H, m), 7.66-7.54 (4H, m).
ES-MS (m/z): 394 (M+H)$^+$.

Production Example 9

2-phenyl-N-[5-(3-pyridyl)-1,3,4-oxadiazol-2-yl]-4-quinolinecarboxamide (compound Ia-9)

$^1$H-NMR (DMSO-d$_6$) δ: 9.17 (1H, s), 8.83 (1H, d, J=4.5 Hz), 8.51 (1H, s), 8.38-8.35 (3H, m), 8.28 (1H, brd, J=7.4 Hz), 8.21 (1H, d, J=8.5 Hz), 7.90 (1H, dd, J=8.5 Hz, 7.4 Hz), 7.73 (1H, dd, J=7.4 Hz, 7.4 Hz), 7.68 (1H, dd, J=7.9 Hz, 4.5 Hz), 7.63-7.55 (3H, m).
ES-MS (m/z): 394 (M+H)$^+$.

Production Example 10

N-[(5-phenyl-1,3,4-oxadiazol-2-yl)methyl]-4-quinolinecarboxamide (compound Ia-10)

$^1$H-NMR (DMSO-d$_6$) δ: 9.75 (1H, t, J=5.7 Hz), 8.33 (2H, d, J=8.6 Hz), 8.28 (1H, d, J=8.6 Hz), 8.25 (1H, s), 8.16 (1H, d, J=8.0 Hz), 8.04 (1H, dd, J=7.4 Hz, 1.7 Hz), 7.86 (1H, m), 7.69-7.53 (7H, m), 4.95 (2H, d, J=5.7 Hz).
ES-MS (m/z): 407 (M+H)$^+$.

Example 5

N-[5-(2-furyl)-1,3,4-oxadiazol-2-yl]-4-quinolinecarboxamide (compound Ia-11)

ES-MS (m/z): 307 (M+H)$^+$.

Example 6

2-chloro-N-[5-(2-furyl)-1,3,4-oxadiazol-2-yl]-4-quinolinecarboxamide (compound Ia-12)

$^1$H-NMR (DMSO-d$_6$) δ: 8.26 (1H, m), 8.09-8.07 (2H, m), 7.98 (1H, s), 7.93 (1H, m), 7.77 (1H, m), 7.29 (1H, s), 6.81 (1H, dd, J=3.7 Hz, 1.7 Hz).
ES-MS (m/z): 343 ($^{37}$ClM+H)$^+$, 341 ($^{35}$ClM+H)$^+$.

Example 7

2-bromo-N-[5-(2-furyl)-1,3,4-oxadiazol-2-yl]-4-quinolinecarboxamide (compound Ia-13)

ES-MS (m/z): 387 ($^{81}$BrM+H)$^+$, 385 ($^{79}$BrM+H)$^+$.

Example 8

N-[5-(2-furyl)-1,3,4-oxadiazol-2-yl]-2-piperidino-4-quinolinecarboxamide (compound Ia-14)

$^1$H-NMR (DMSO-d$_6$) δ: 8.08 (1H, s), 7.89 (1H, d, J=8.0 Hz), 7.62-7.57 (3H, m), 7.31 (1H, d, J=3.4 Hz), 7.26 (1H, m), 6.82 (1H, dd, J=3.4 Hz, 1.7 Hz), 3.78-3.76 (4H, m), 1.68-1.67 (2H, m), 1.61-1.60 (4H, m).
ES-MS (m/z): 390 (M+H)$^+$.

Example 9

N-[5-(2-furyl)-1,3,4-oxadiazol-2-yl]-2-(3-hydroxyphenyl)-4-quinolinecarboxamide (compound Ia-15)

The title compound was synthesized according to the synthesis method of a compound Ia-16 described later using 3-hydroxyphenylboronic acid instead of 3-nitrophenylboronic acid.
ES-MS (m/z): 399 (M+H)$^+$.

Example 10

N-[5-(2-furyl)-1,3,4-oxadiazol-2-yl]-2-(3-nitrophenyl)-4-quinolinecarboxamide (compound Ia-16)

Palladium (II) chloride (4 mg, 0.02 mmol), 2-dicyclohexylphosphino-2',4',6'-triisopropylbiphenyl (21 mg, 0.04 mmol), tripotassium phosphate (93 mg, 0.44 mmol), and 3-nitrophenylboronic acid (55 mg, 0.33 mmol) were added to an n-butanol (1.5 mL) suspension of the compound Ia-12 (75 mg, 0.22 mmol), and the mixture was heated with stirring at 120° C. for 10 hours. The reaction solution was concentrated. After that, to the residue, a saturated aqueous solution of sodium chloride was added, and the deposited crystal was collected by filtration, washed with water, dried, and then purified by preparative HPLC to obtain the title compound (8 mg, 0.02 mmol).

$^1$H-NMR (DMSO-d$_6$) δ: 8.77 (1H, d, J=8.3 Hz), 8.60 (1H, s), 8.39-8.36 (2H, m), 8.24 (1H, d, J=8.3 Hz), 8.00 (1H, s), 7.91-7.87 (3H, m), 7.73 (1H, d, J=1.5 Hz), 7.25 (1H, d, J=3.4 Hz), 6.78 (1H, dd, J=3.4 Hz, 1.5 Hz).
ES-MS (m/z): 428 (M+H)$^+$.

Example 11

2-(4-cyanophenyl)-N-[5-(2-furyl)-1,3,4-oxadiazol-2-yl]-4-quinolinecarboxamide (compound Ia-17)

The title compound was synthesized according to the synthesis method of a compound Ia-46 described later using 2-(4-cyanophenyl)-4-quinolinecarboxylic acid described in Reference Example 10 instead of 2-(4-fluorophenyl)-4-quinolinecarboxylic acid.

$^1$H-NMR (DMSO-d$_6$) δ: 8.61 (1H, s), 8.56 (2H, d, J=8.5 Hz), 8.32 (1H, m), 8.24 (1H, d, J=8.5 Hz), 8.09-8.10 (3H, m), 7.93 (1H, dd, J=7.4 Hz, 7.4 Hz), 7.77 (1H, dd, J=7.4 Hz, 7.4 Hz), 7.33 (1H, d, J=2.9 Hz), 6.83 (1H, brs).
ES-MS (m/z): 408 (M+H)$^+$.

Example 12

2-(2-furyl)-N-[5-(2-furyl)-1,3,4-oxadiazol-2-yl]-4-quinolinecarboxamide (compound Ia-18)

The title compound was synthesized according to the synthesis method of a compound Ia-46 described later using commercially available 2-(2-furyl)-4-quinolinecarboxylic acid, HBTU, and HOBt instead of 2-(4-fluorophenyl)-4-quinolinecarboxylic acid, HATU, and HOAt, respectively.

$^1$H-NMR (DMSO-$d_6$) δ: 8.26 (1H, s), 8.16 (1H, brs), 8.10 (1H, d, J=8.5 Hz), 8.07 (1H, s), 8.00 (1H, d, J=1.7 Hz), 7.85 (1H, dd, J=7.4 Hz, 7.4 Hz), 7.67 (1H, dd, J=8.5 Hz, 7.4 Hz), 7.48 (1H, d, J=3.4 Hz), 7.31 (1H, s), 6.81 (1H, dd, J=3.4 Hz, 1.7 Hz), 6.77 (1H, dd, J=3.4 Hz, 1.7 Hz).

ES-MS (m/z): 373 (M+H)$^+$.

The following compounds Ia-19 to Ia-27 were synthesized according to the method of Production Example 1 using corresponding carboxylic acid and commercially available amine instead of 2-phenyl-4-quinolinecarboxylic acid and 2-amino-5-(2-furyl)-1,3,4-oxadiazole.

Example 13

2-(5-chloro-2-thienyl)-N-[5-(2-furyl)-1,3,4-oxadiazol-2-yl]-4-quinolinecarboxamide (compound Ia-19)

$^1$H-NMR (DMSO-$d_6$) δ: 8.48 (1H, s), 8.17 (1H, d, J=8.3 Hz), 8.09-8.01 (3H, m), 7.86 (1H, m), 7.69 (1H, m), 7.32-7.31 (2H, m), 6.82 (1H, dd, J=3.4 Hz, 1.7 Hz).

ES-MS (m/z): 425 ($^{37}$ClM+H)$^+$, 423 ($^{35}$ClM+H)$^+$.

Example 14

N-[5-(2-furyl)-1,3,4-oxadiazol-2-yl]-2-(4-pyridyl)-4-quinolinecarboxamide (compound Ia-20)

ES-MS (m/z): 384 (M+H)$^+$.

Example 15

N-[5-(2-furyl)-1,3,4-oxadiazol-2-yl]-9-acridinecarboxamide (compound Ia-21)

ES-MS (m/z): 357 (M+H)$^+$.

Example 16

6-chloro-N-[5-(2-furyl)-1,3,4-oxadiazol-2-yl]-2-phenyl-4-quinolinecarboxamide (compound Ia-22)

$^1$H-NMR (DMSO-$d_6$) δ: 12.90 (1H, brs), 8.58 (1H, s), 8.38-8.35 (3H, m), 8.22 (1H, d, J=8.8 Hz), 8.09 (1H, d, J=2.0 Hz), 7.91 (1H, dd, J=8.8 Hz, 2.0 Hz), 7.64-7.55 (3H, m), 7.33 (1H, d, J=3.4 Hz), 6.83 (1H, dd, J=3.4 Hz, 2.0 Hz).

ES-MS (m/z): 419 ($^{37}$ClM+H)$^+$, 417 ($^{35}$ClM+H)$^+$.

Example 17

N-[5-(2-furyl)-1,3,4-oxadiazol-2-yl]-6-methoxy-2-phenyl-4-quinolinecarboxamide (compound Ia-23)

$^1$H-NMR (DMSO-$d_6$) δ: 12.75 (1H, br), 8.45 (1H, s), 8.32 (2H, d, J=7.3 Hz), 8.12-8.07 (2H, m), 7.66 (1H, br), 7.60-7.50 (4H, m), 7.32 (1H, d, J=3.4 Hz), 6.82 (1H, dd, J=3.4 Hz, 2.0 Hz), 3.92 (3H, s).

ES-MS (m/z): 413 (M+H)$^+$.

Example 18

7-bromo-N-[5-(2-furyl)-1,3,4-oxadiazol-2-yl]-2-phenyl-4-quinolinecarboxamide (compound Ia-24)

$^1$H-NMR (DMSO-$d_6$) δ: 8.56 (1H, s), 8.42 (1H, d, J=1.7 Hz), 8.36 (1H, d, J=6.9 Hz), 8.09 (1H, s), 7.95 (1H, s), 7.87 (1H, dd, J=8.6 Hz, 1.7 Hz), 7.63-7.56 (4H, m), 7.32 (1H, d, J=3.4 Hz), 6.82 (1H, d, J=1.7 Hz).

ES-MS (m/z): 463 ($^{81}$BrM+H)$^+$, 461 ($^{79}$BrM+H)$^+$.

Example 19

N-[5-(2-furyl)-1,3,4-oxadiazol-2-yl]-8-methyl-2-phenyl-4-quinolinecarboxamide (compound Ia-25)

$^1$H-NMR (DMSO-$d_6$) δ: 8.50 (1H, s), 8.41 (2H, d, J=7.3 Hz), 8.09-8.06 (2H, m), 7.75 (1H, t, J=7.1 Hz), 7.63-7.55 (4H, m), 7.32 (1H, d, J=3.4 Hz), 6.82 (1H, d, J=1.7 Hz), 2.87 (3H, s).

ES-MS (m/z): 397 (M+H)$^+$.

Example 20

7-chloro-N-[5-(2-furyl)-1,3,4-oxadiazol-2-yl]-8-methyl-2-phenyl-4-quinolinecarboxamide (compound Ia-26)

$^1$H-NMR (DMSO-$d_6$) δ: 8.55 (1H, s), 8.42 (2H, d, J=8.3 Hz), 8.13-8.08 (2H, m), 7.64-7.55 (4H, m), 7.32 (1H, d, J=3.4 Hz), 6.82 (1H, dd, J=3.4 Hz, 1.7 Hz), 2.94 (3H, s).

ES-MS (m/z): 433 ($^{37}$ClM+H)$^+$, 431 ($^{35}$ClM+H)$^+$.

Example 21

N-[5-(2-furyl)-1,3,4-oxadiazol-2-yl]-8-methyl-2-(4-tolyl)-4-quinolinecarboxamide (compound Ia-27)

$^1$H-NMR (DMSO-$d_6$) δ: 8.46 (1H, s), 8.31 (2H, d, J=7.8 Hz), 8.09-8.04 (2H, m), 7.73 (1H, d, J=6.8 Hz), 7.57 (1H, t, J=7.8 Hz), 7.41 (2H, d, J=7.8 Hz), 7.32 (1H, s), 6.82 (1H, s), 2.86 (3H, s), 2.42 (3H, s).

ES-MS (m/z): 411 (M+H)$^+$.

Example 22

7-chloro-2-(2-furyl)-N-[5-(2-furyl)-1,3,4-oxadiazol-2-yl]-8-methyl-4-quinolinecarboxamide (compound Ia-28)

The title compound was synthesized according to the synthesis method of a compound Ia-46 described later using commercially available 7-chloro-2-(2-furyl)-8-methyl-4-quinolinecarboxylic acid instead of 2-(4-fluorophenyl)-4-quinolinecarboxylic acid.

$^1$H-NMR (DMSO-$d_6$) δ: 8.28 (1H, s), 8.07-8.02 (3H, m), 7.68 (1H, d, J=9.1 Hz), 7.52 (1H, d, J=3.4 Hz), 7.31 (1H, d, J=3.4 Hz), 6.81 (1H, dd, J=3.4 Hz, 1.7 Hz), 6.79 (1H, dd, J=3.4 Hz, 1.7 Hz), 2.87 (3H, s).

ES-MS (m/z): 423 ($^{37}$ClM+H)$^+$, 421 ($^{35}$ClM+H)$^+$.

Example 23

N-[5-(2-furyl)-1,3,4-oxadiazol-2-yl]-6-methyl-2-(2-thienyl)-4-quinolinecarboxamide (compound Ia-29)

The title compound was synthesized according to the method of Production Example 1 using commercially available 6-methyl-2-(2-thienyl)-4-quinolinecarboxylic acid instead of 2-phenyl-4-quinolinecarboxylic acid.

$^1$H-NMR (DMSO-$d_6$) δ: 8.48 (1H, s), 8.35 (1H, s), 8.02 (1H, s), 7.91-7.84 (2H, m), 7.73 (1H, d, J=4.9 Hz), 7.50 (1H, d, J=8.5 Hz), 7.27 (1H, d, J=2.9 Hz), 7.21 (1H, t, J=4.4 Hz), 6.79 (1H, s), 2.51 (3H, s).

ES-MS (m/z): 403 (M+H)$^+$.

Example 24

6-chloro-N-[5-(2-furyl)-1,3,4-oxadiazol-2-yl]-2-(2-thienyl)-4-quinolinecarboxamide (compound Ia-30)

The title compound was synthesized according to the synthesis method of a compound Ia-46 described later using commercially available 6-chloro-2-(2-thienyl)-4-quinolinecarboxylic acid, HBTU, and HOBt instead of 2-(4-fluorophenyl)-4-quinolinecarboxylic acid, HATU, and HOAt, respectively.

$^1$H-NMR (DMSO-$d_6$) δ: 8.55 (1H, s), 8.27 (1H, brs), 8.14 (1H, d, J=4.0 Hz), 8.10-8.09 (2H, m), 7.87-7.83 (2H, m), 7.33 (1H, d, J=3.4 Hz), 7.29 (1H, dd, J=5.1 Hz, 4.0 Hz), 6.83 (1H, dd, J=3.4 Hz, 1.7 Hz).

ES-MS (m/z): 425 ($^{37}$ClM+H)$^+$, 423 ($^{35}$ClM+H)$^+$.

Example 25

N-[5-(2-furyl)-1,3,4-oxadiazol-2-yl]-8-methyl-2-(2-thienyl)-4-quinolinecarboxamide (compound Ia-31)

Triphenylphosphine bromide (352 mg, 0.80 mmol) was added to a methylene chloride (1 mL) solution of commercially available 8-methyl-2-(2-thienyl)-4-quinolinecarboxylic acid (108 mg, 0.40 mmol), and the mixture was stirred at room temperature for 1 hour. The reaction solution was added to a pyridine (3 mL) solution of 2-amino-5-(2-furyl)-1,3,4-oxadiazole (90.7 mg, 0.60 mmol), and the mixture was stirred at room temperature for 2 hours and then heated with stirring overnight at 60° C. The reaction solution was concentrated. After that, to the residue, water was added, and the deposited solid was collected by filtration, washed with water, dried, and then purified by preparative HPLC to obtain the title compound (22 mg, 0.05 mmol).

$^1$H-NMR (DMSO-$d_6$) δ: 12.84 (1H, br), 8.40 (1H, s), 8.08-8.02 (3H, m), 7.77 (1H, d, J=5.4 Hz), 7.69 (1H, d, J=6.8 Hz), 7.52 (1H, t, J=7.8 Hz), 7.29-7.24 (2H, m), 6.80 (1H, brs), 2.78 (3H, s).

ES-MS (m/z): 403 (M+H)$^+$.

The following compounds Ia-32 and Ia-33 were synthesized according to the method of Production Example 1 using corresponding carboxylic acid instead of 2-phenyl-4-quinolinecarboxylic acid.

Example 26

8-chloro-N-[5-(2-furyl)-1,3,4-oxadiazol-2-yl]-2-(2-thienyl)-4-quinolinecarboxamide (compound Ia-32)

$^1$H-NMR (DMSO-$d_6$) δ: 8.42 (1H, s), 8.04-7.88 (3H, m), 7.78 (1H, m), 7.63-7.54 (2H, m), 7.24-7.19 (2H, m), 6.76 (1H, dd, J=3.4 Hz, 1.5 Hz).

ES-MS (m/z): 425 ($^{37}$ClM+H)$^+$, 423 ($^{35}$ClM+H)$^+$.

Example 27

N-[5-(2-furyl)-1,3,4-oxadiazol-2-yl]-6,8-dimethyl-2-(2-thienyl)-4-quinolinecarboxamide (compound Ia-33)

$^1$H-NMR (DMSO-$d_6$) δ: 12.82 (1H, brs), 8.38 (1H, s), 8.07 (2H, m), 7.76 (2H, m), 7.56 (1H, s), 7.32 (1H, d, J=3.4 Hz), 7.25 (1H, dd, J=5.1 Hz, 3.7 Hz), 6.82 (1H, dd, J=3.4 Hz, 1.7 Hz), 2.51 (3H, s), 2.50 (3H, s)

ES-MS (m/z): 417 (M+H)$^+$..

Example 28

N-[5-(2-furyl)-1,3,4-oxadiazol-2-yl]-2-hydroxy-4-quinolinecarboxamide (compound Ia-34)

The title compound was synthesized according to the synthesis method of a compound Ia-46 described later using 2-hydroxy-4-quinolinecarboxylic acid, commercially available amine, HBTU, and HOBt instead of 2-(4-fluorophenyl)-4-quinolinecarboxylic acid, HATU, and HOAt.

$^1$H-NMR (DMSO-$d_6$) δ: 12.11 (1H, brs), 8.07 (1H, s), 7.75 (1H, brs), 7.59 (1H, dd, J=8.5 Hz, 7.4 Hz), 7.40 (1H, d, J=8.5 Hz), 7.31 (1H, d, J=3.4 Hz), 7.25 (1H, dd, J=8.5 Hz, 7.4 Hz), 6.85 (1H, s), 6.82 (1H, dd, J=3.4 Hz, 1.7 Hz).

ES-MS (m/z): 323 (M+H)$^+$.

Example 29

2-(1-butoxy)-N-[5-(2-furyl)-1,3,4-oxadiazol-2-yl]-4-quinolinecarboxamide (compound Ia-35)

The title compound was obtained according to the synthesis method of the compound Ia-15.

$^1$H-NMR (DMSO-$d_6$) δ: 12.73 (1H, brs), 8.09 (1H, d, J=8.3 Hz), 8.06 (1H, s), 7.85 (1H, d, J=8.3 Hz), 7.74 (1H, dd, J=8.3 Hz, 6.8 Hz), 7.51 (1H, dd, J=8.3 Hz, 7.3 Hz), 7.33 (1H, d, J=2.0 Hz), 7.28 (1H, m), 6.80 (1H, dd, J=3.9 Hz, 2.0 Hz), 4.48 (2H, t, J=6.8 Hz), 1.79 (2H, tt, J=7.8 Hz, 6.8 Hz), 1.49 (2H, tq, J=7.8 Hz, 7.3 Hz), 0.97 (3H, t, J=7.3 Hz).

ES-MS (m/z): 379 (M+H)$^+$.

Example 30

2-(2-fluorophenyl)-N-[5-(2-furyl)-1,3,4-oxadiazol-2-yl]-4-quinolinecarboxamide (compound Ia-36)

The title compound was synthesized according to the synthesis method of Production Example 1 using 2-(2-fluorophenyl)-4-quinolinecarboxylic acid instead of 2-phenyl-4-quinolinecarboxylic acid.

ES-MS (m/z): 401 (M+H)$^+$.

Example 31

2-(2-chlorophenyl)-N-[5-(2-furyl)-1,3,4-oxadiazol-2-yl]-4-quinolinecarboxamide (compound Ia-37)

The title compound was synthesized according to the synthesis method of a compound Ia-46 described later using commercially available 2-(2-chlorophenyl)-4-quinolinecarboxylic acid instead of 2-(4-fluorophenyl)-4-quinolinecarboxylic acid.

$^1$H-NMR (DMSO-$d_6$) δ: 8.30 (1H, brs), 8.20 (1H, d, J=8.5 Hz), 8.09-8.07 (2H, m), 7.93 (1H, m), 7.81-7.75 (2H, m), 7.68 (1H, m), 7.59-7.55 (2H, m), 7.30 (1H, d, J=3.4 Hz), 6.82 (1H, dd, J=3.4 Hz, 1.7 Hz).

ES-MS (m/z): 419 ($^{37}$ClM+H)$^+$, 417 ($^{35}$ClM+H)$^+$.

Example 32

N-[5-(2-furyl)-1,3,4-oxadiazol-2-yl]-2-(2-hydroxyphenyl)-4-quinolinecarboxamide (compound Ia-38)

2-(2-acetoxyphenyl)-N-[5-(2-furyl)-1,3,4-oxadiazol-2-yl]-4-quinolinecarboxamide was synthesized according to the method of Production Example 1 using 2-(2-acetoxyphenyl)quinolinecarboxylic acid described in Reference Example 14 instead of 2-phenyl-4-quinolinecarboxylic acid, and deprotected with potassium carbonate to obtain the title compound.

$^1$H-NMR (DMSO-$d_6$) δ: 14.27 (1H, brs), 12.92 (1H, brs), 8.70 (1H, s), 8.29 (1H, d, J=8.3 Hz), 8.27 (1H, d, J=8.8 Hz), 8.20 (1H, d, J=8.3 Hz), 8.07 (1H, d, J=1.5 Hz), 7.92 (1H, ddd, J=8.3 Hz, 8.3 Hz, 1.5 Hz), 7.75 (1H, ddd, J=8.3 Hz, 8.3 Hz, 1.5 Hz), 7.43 (1H, ddd, J=8.3 Hz, 8.3 Hz, 1.5 Hz), 7.31 (1H, d, J=3.4 Hz), 7.05-7.01 (2H, m), 6.82 (1H, dd, J=3.4 Hz, 1.5 Hz).

ES-MS (m/z): 399 (M+H)$^+$.

Example 33

N-[5-(2-furyl)-1,3,4-oxadiazol-2-yl]-2-(2-nitrophenyl)-4-quinolinecarboxamide (compound Ia-39)

The title compound was synthesized according to the synthesis method of a compound Ia-46 described later using 2-(2-nitrophenyl)-4-quinolinecarboxylic acid described in Reference Example 7, HBTU, and HOBt instead of 2-(4-fluorophenyl)-4-quinolinecarboxylic acid, HATU, and HOAt, respectively.

$^1$H-NMR (DMSO-$d_6$) δ: 8.32 (1H, d, J=7.9 Hz), 8.26 (1H, s), 8.10-8.08 (2H, m), 8.04-8.02 (2H, m), 7.93-7.89 (2H, m), 7.80-7.77 (2H, m), 7.31 (1H, d, J=2.8 Hz), 6.82 (1H, dd, J=3.4 Hz, 1.7 Hz).

ES-MS (m/z): 427 (M+H)$^+$.

Example 34

2-(2-aminophenyl)-N-[5-(2-furyl)-1,3,4-oxadiazol-2-yl]-4-quinolinecarboxamide (compound Ia-40)

The compound Ia-39 was subjected to catalytic reduction by a routine method to obtain the title compound.

$^1$H-NMR (DMSO-$d_6$) δ: 8.36 (1H, s), 8.23 (1H, d, J=7.9 Hz), 8.15 (1H, d, J=8.5 Hz), 8.08 (1H, d, J=1.1 Hz), 7.94 (1H, d, J=7.4 Hz), 7.85 (1H, ddd, J=8.5 Hz, 7.4 Hz, 1.1 Hz), 7.67 (1H, ddd, J=7.9 Hz, 7.4 Hz, 1.1 Hz), 7.32 (1H, d, J=3.4 Hz), 7.19 (1H, ddd, J=8.5 Hz, 7.4 Hz, 1.1 Hz), 6.88 (1H, dd, J=7.9 Hz, 1.1 Hz), 6.82 (1H, dd, J=3.4 Hz, 1.7 Hz), 6.70 (1H, ddd, J=7.9 Hz, 7.4 Hz, 1.1 Hz).

ES-MS (m/z): 398 (M+H)$^+$.

Example 35

2-(3-chlorophenyl)-N-[5-(2-furyl)-1,3,4-oxadiazol-2-yl]-4-quinolinecarboxamide (compound Ia-41)

The title compound was synthesized according to the synthesis method of a compound Ia-46 described later using commercially available 2-(3-chlorophenyl)-4-quinolinecarboxylic acid instead of 2-(4-fluorophenyl)-4-quinolinecarboxylic acid.

$^1$H-NMR (DMSO-$d_6$) δ: 8.56 (1H, s), 8.42 (1H, s), 8.33 (1H, m), 8.28 (1H, brd, J=8.5 Hz), 8.21 (1H, d, J=8.5 Hz), 8.07 (1H, d, J=1.7 Hz), 7.90 (1H, dd, J=8.5 Hz, 6.8 Hz), 7.73 (1H, dd, J=8.5 Hz, 6.8 Hz), 7.65-7.61 (2H, m), 7.31 (1H, d, J=3.4 Hz), 6.81 (1H, dd, J=3.4 Hz, 1.7 Hz).

ES-MS (m/z): 419 ($^{37}$ClM+H)$^+$, 417 ($^{35}$ClM+H)$^+$.

Example 36

N-[5-(2-furyl)-1,3,4-oxadiazol-2-yl]-2-(3-methoxyphenyl)-4-quinolinecarboxamide (compound Ia-42)

The title compound was synthesized according to the synthesis method of Production Example 1 using commercially available 2-(3-methoxyphenyl)-4-quinolinecarboxylic acid instead of 2-phenyl-4-quinolinecarboxylic acid.

$^1$H-NMR (DMSO-$d_6$) δ: 12.84 (1H, br), 8.50 (1H, s), 8.27 (1H, d, J=8.3 Hz), 8.20 (1H, d, J=8.8 Hz), 8.08 (1H, d, J=2.0 Hz), 7.95-7.86 (3H, m), 7.72 (1H, dd, J=8.3 Hz, 7.3 Hz), 7.52 (1H, dd, J=8.3 Hz, 7.3 Hz), 7.32 (1H, d, J=3.9 Hz), 7.13 (1H, dd, J=7.8 Hz, 2.4 Hz), 6.82 (1H, dd, J=3.9 Hz, 2.0 Hz), 3.90 (3H, s).

ES-MS (m/z): 413 (M+H)$^+$.

The following compounds Ia-43 and Ia-44 were synthesized according to the method of Production Example 1 using corresponding carboxylic acid instead of 2-phenyl-4-quinolinecarboxylic acid.

Example 37

2-(3-cyanophenyl)-N-[5-(2-furyl)-1,3,4-oxadiazol-2-yl]-4-quinolinecarboxamide (compound Ia-43)

$^1$H-NMR (DMSO-$d_6$) δ: 8.81 (1H, s), 8.72 (1H, d, J=7.9 Hz), 8.65 (1H, s), 8.30 (1H, brs), 8.25 (1H, d, J=8.5 Hz), 8.09 (1H, s), 8.04 (1H, d, J=7.4 Hz), 7.93 (1H, m), 7.84 (1H, m), 7.77 (1H, m), 7.32 (1H, s), 6.83 (1H, dd, J=3.4 Hz, 1.7 Hz).

ES-MS (m/z): 408 (M+H)$^+$.

Example 38

2-(3-tert-butoxycarbonylphenyl)-N-[5-(2-furyl)-1,3,4-oxadiazol-2-yl]-4-quinolinecarboxamide (compound Ia-44)

$^1$H-NMR (DMSO-$d_6$) δ: 8.95 (1H, brs), 8.69 (1H, brs), 8.60 (1H, br), 8.30 (1H, br), 8.19-8.15 (2H, m), 7.94-7.67 (4H, m), 7.42 (1H, brs), 6.93 (1H, brs), 1.76 (9H, s).

ES-MS (m/z): 483 (M+H)$^+$.

Example 39

2-(3-carboxyphenyl)-N-[5-(2-furyl)-1,3,4-oxadiazol-2-yl]-4-quinolinecarboxamide (compound Ia-45)

The compound Ia-44 was treated with trifluoroacetic acid to obtain the title compound.

$^1$H-NMR (DMSO-$d_6$) δ: 12.83 (1H, br), 8.92 (1H, s), 8.59 (1H, d, J=7.8 Hz), 8.55 (1H, s), 8.29 (1H, d, J=8.3 Hz), 8.23 (1H, d, J=8.3 Hz), 8.11 (1H, d, J=7.8 Hz), 8.06 (1H, d, J=2.0 Hz), 7.89 (1H, dd, J=8.3 Hz, 7.3 Hz), 7.75-7.71 (2H, m), 7.31 (1H, d, J=3.4 Hz), 6.81 (1H, dd, J=3.4 Hz, 2.0 Hz).

ES-MS (m/z): 427 (M+H)$^+$.

Example 40

2-(4-fluorophenyl)-N-[5-(2-furyl)-1,3,4-oxadiazol-2-yl]-4-quinolinecarboxamide (compound Ia-46)

Commercially available 2-amino-5-(2-furyl)-1,3,4-oxadiazole (57 mg, 0.38 mmol), HOAt (51 mg, 0.37 mmol), HATU (143 mg, 0.38 mmol), and N,N-diisopropylethylamine (87 μL, 0.50 mmol) were added to a DMF (2 mL) solution of commercially available 2-(4-fluorophenyl)-4-quinolinecarboxylic acid (67 mg, 0.25 mmol), and the mixture was stirred at room temperature for 3 days. To the reaction solution, water was added, and the deposited solid was collected by filtration, and washed with water and then with methanol and methylene chloride in this order. The obtained solid was dried to obtain the title compound (61 mg, 0.15 mmol).

$^1$H-NMR (DMSO-$d_6$) δ: 8.50 (1H, s), 8.42 (2H, dd, J=8.5 Hz, 5.1 Hz), 8.25 (1H, brd, J=7.9 Hz), 8.18 (1H, d, J=8.5 Hz), 8.07 (1H, d, J=1.7 Hz), 7.88 (1H, m), 7.71 (1H, m), 7.45-7.42 (2H, m), 7.31 (1H, d, J=3.4 Hz), 6.81 (1H, dd, J=3.4 Hz, 1.7 Hz).

ES-MS (m/z): 401 (M+H)$^+$.

The following compounds Ia-47 and Ia-48 were synthesized according to the synthesis method of Production Example 1 using corresponding carboxylic acid instead of 2-phenyl-4-quinolinecarboxylic acid.

Example 41

2-(4-chlorophenyl)-N-[5-(2-furyl)-1,3,4-oxadiazol-2-yl]-4-quinolinecarboxamide (compound Ia-47)

$^1$H-NMR (DMSO-$d_6$) δ: 12.84 (1H, brs), 8.52 (1H, s), 8.40 (2H, d, J=8.8 Hz), 8.27 (1H, brd, J=8.3 Hz), 8.20 (1H, d, J=8.3 Hz), 8.08 (1H, d, J=2.0 Hz), 7.90 (1H, dd, J=8.3 Hz, 7.3 Hz), 7.73 (1H, dd, J=8.3 Hz, 7.3 Hz), 7.68 (2H, d, J=8.8 Hz), 7.32 (1H, d, J=3.2 Hz), 6.82 (1H, dd, J=3.2 Hz, 2.0 Hz).

ES-MS (m/z): 419 ($^{37}$ClM+H)$^+$, 417 ($^{35}$ClM+H)$^+$.

Example 42

N-[5-(2-furyl)-1,3,4-oxadiazol-2-yl]-2-(4-methylphenyl)-4-quinolinecarboxamide (compound Ia-48)

$^1$H-NMR (DMSO-$d_6$) δ: 12.83 (1H, br), 8.47 (1H, s), 8.29-8.25 (3H, m), 8.17 (1H, d, J=8.3 Hz), 8.08 (1H, d, J=1.5 Hz), 7.87 (1H, dd, J=7.8 Hz, 7.3 Hz), 7.69 (1H, dd, J=7.8 Hz, 7.3 Hz), 7.41 (2H, d, J=8.3 Hz), 7.32 (1H, d, J=3.4 Hz), 6.82 (1H, dd, J=3.4 Hz, 1.5 Hz), 2.42 (3H, s).

ES-MS (m/z): 397 (M+H)$^+$.

Example 43

2-(4-difluoromethoxyphenyl)-N-[5-(2-furyl)-1,3,4-oxadiazol-2-yl]-4-quinolinecarboxamide (compound Ia-49)

The title compound was synthesized according to the synthesis method of the compound Ia-46 using commercially available 2-(4-difluoromethoxyphenyl)-4-quinolinecarboxylic acid instead of 2-(4-fluorophenyl)-4-quinolinecarboxylic acid.

$^1$H-NMR (DMSO-$d_6$) δ: 8.49 (1H, s), 8.43 (2H, d, J=8.5 Hz), 8.26 (1H, brd, J=7.9 Hz), 8.18 (1H, d, J=8.5 Hz), 8.07 (1H, d, J=1.7 Hz), 7.88 (1H, dd, J=8.5 Hz, 6.8 Hz), 7.71 (1H, dd, J=7.9 Hz, 7.4 Hz), 7.41-7.39 (2H, m), 7.40 (1H, t, J=73.6 Hz), 7.31 (1H, d, J=3.4 Hz), 6.82 (1H, dd, J=3.4 Hz, 1.7 Hz).

ES-MS (m/z): 449 (M+H)$^+$.

Example 44

N-[5-(2-furyl)-1,3,4-oxadiazol-2-yl]-2-(4-hydroxyphenyl)-4-quinolinecarboxamide (compound Ia-50)

The title compound was synthesized according to the synthesis method of the compound Ia-38 using 2-(4-acetoxyphenyl)quinolinecarboxylic acid described in Reference Example 15 instead of 2-(2-acetoxyphenyl)quinolinecarboxylic acid.

$^1$H-NMR (DMSO-$d_6$) δ: 12.79 (1H, brs), 9.94 (1H, brs), 8.60 (1H, s), 8.35 (1H, s), 8.21 (2H, d, J=7.8 Hz), 8.09 (1H, d, J=7.8 Hz), 8.05 (1H, d, J=1.5 Hz), 7.81 (1H, dd, J=7.8 Hz, 7.8 Hz), 7.62 (1H, dd, J=7.8 Hz, 7.8 Hz), 7.26 (1H, s), 6.95 (2H, dd, J=7.8 Hz, 1.5 Hz), 6.80 (1H, s).

ES-MS (m/z): 399 (M+H)$^+$.

The following compounds Ia-51 and Ia-52 were synthesized according to the synthesis method of the compound Ia-46 using corresponding carboxylic acid, HBTU, and HOBt instead of 2-(4-fluorophenyl)-4-quinolinecarboxylic acid, HATU, and HOAt, respectively.

Example 45

N-[5-(2-furyl)-1,3,4-oxadiazol-2-yl]-2-(4-methoxyphenyl)-4-quinolinecarboxamide (compound Ia-51)

ES-MS (m/z): 413 (M+H)$^+$.

Example 46

N-[5-(2-furyl)-1,3,4-oxadiazol-2-yl]-2-(4-nitrophenyl)-4-quinolinecarboxamide (compound Ia-52)

$^1$H-NMR (DMSO-$d_6$) E: 8.64 (3H, m), 8.46 (2H, d, J=8.5 Hz), 8.33 (1H, d, J=8.5 Hz), 8.26 (1H, d, J=8.5 Hz), 8.08 (1H, brs), 7.94 (1H, dd, J=8.5 Hz, 7.4 Hz), 7.79 (1H, dd, J=8.5 Hz, 7.4 Hz), 7.32 (1H, d, J=2.8 Hz), 6.83 (1H, dd, J=3.4 Hz, 1.7 Hz).

ES-MS (m/z): 428 (M+H)$^+$.

Example 47

2-(4-tert-butoxycarbonylphenyl)-N-[5-(2-furyl)-1,3,4-oxadiazol-2-yl]-4-quinolinecarboxamide (compound Ia-53)

The title compound was synthesized according to the method of Production Example 1 using 2-(4-tert-butoxycarbonylphenyl)-4-quinolinecarboxylic acid described in Reference Example 11 instead of 2-phenyl-4-quinolinecarboxylic acid.

$^1$H-NMR (DMSO-$d_6$) δ: 8.66 (1H, s), 8.52 (2H, br), 8.32-8.14 (5H, m), 7.97 (1H, br), 7.75 (1H, br), 7.38 (1H, brs), 6.92 (1H, brs), 1.76 (9H, s).

ES-MS (m/z): 483 (M+H)$^+$.

Example 48

2-(4-carboxyphenyl)-N-[5-(2-furyl)-1,3,4-oxadiazol-2-yl]-4-quinolinecarboxamide (compound Ia-54)

The compound Ia-53 was treated with trifluoroacetic acid to obtain the title compound.

$^1$H-NMR (DMSO-$d_6$) δ: 12.82 (1H, brs), 8.56 (1H, s), 8.48 (2H, d, J=8.8 Hz), 8.27 (1H, d, J=8.8 Hz), 8.22 (1H, d, J=8.8 Hz), 8.15 (2H, d, J=8.8 Hz), 8.06 (1H, d, J=2.0 Hz), 7.90 (1H, dd, J=8.8 Hz, 7.3 Hz), 7.74 (1H, dd, J=8.8 Hz, 7.3 Hz), 7.31 (1H, d, J=3.4 Hz), 6.81 (1H, dd, J=3.4 Hz, 2.0 Hz).

ES-MS (m/z): 427 (M+H)$^+$.

Example 49

N-[5-(2-furyl)-1,3,4-oxadiazol-2-yl]-2-(4-sulfamoylphenyl)-4-quinolinecarboxamide trifluoroacetate (compound Ia-55)

The title compound was synthesized according to the method of Production Example 1 using 2-(4-sulfamoylphenyl)-4-quinolinecarboxylic acid described in Reference Example 12 instead of 2-phenyl-4-quinolinecarboxylic acid.
ES-MS (m/z): 462 (M+H)$^+$.

The following compounds Ia-56 to Ia-58 were synthesized according to the synthesis method of the compound Ia-46 using corresponding carboxylic acid instead of 2-(4-fluorophenyl)-4-quinolinecarboxylic acid.

Example 50

N-[5-(2-furyl)-1,3,4-oxadiazol-2-yl]-2-(2,4-dimethylphenyl)-4-quinolinecarboxamide (compound Ia-56)

ES-MS (m/z): 411 (M+H)$^+$.

Example 51

N-[5-(2-furyl)-1,3,4-oxadiazol-2-yl]-2-(3,4-dimethoxyphenyl)-4-quinolinecarboxamide (compound Ia-57)

$^1$H-NMR (DMSO-d$_6$) δ: 8.48 (1H, s), 8.20 (1H, brd, J=8.5 Hz), 8.16 (1H, d, J=7.9 Hz), 8.09 (1H, d, J=1.7 Hz), 7.98-7.96 (2H, m), 7.86 (1H, m), 7.67 (1H, m), 7.33 (1H, d, J=3.4 Hz), 7.17 (1H, d, J=9.1 Hz), 6.83 (1H, dd, J=3.4 Hz, 1.7 Hz), 3.94 (3H, s), 3.88 (3H, s).
ES-MS (m/z): 443 (M+H)$^+$.

Example 52

N-[5-(2-furyl)-1,3,4-oxadiazol-2-yl]-2-(3,4-methylenedioxyphenyl)-4-quinolinecarboxamide (compound Ia-58)

$^1$H-NMR (DMSO-d$_6$) δ: 8.43 (1H, s), 8.21 (1H, d, J=8.5 Hz), 8.14 (1H, d, J=8.5 Hz), 8.07 (1H, s), 7.94-7.93 (2H, m), 7.85 (1H, dd, J=8.5 Hz, 7.4 Hz), 7.67 (1H, dd, J=7.4 Hz, 7.4 Hz), 7.31 (1H, s), 7.13 (1H, d, J=8.5 Hz), 6.82 (1H, d, J=3.4 Hz), 6.15 (2H, s).
ES-MS (m/z): 427 (M+H)$^+$.

Example 53

2-cyclopropyl-N-[5-(2-furyl)-1,3,4-oxadiazol-2-yl]-4-quinolinecarboxamide (compound Ia-59)

The title compound was synthesized according to the synthesis method of Production Example 1 using commercially available 2-cyclopropyl-4-quinolinecarboxylic acid instead of 2-phenyl-4-quinolinecarboxylic acid.
ES-MS (m/z): 347 (M+H)$^+$.

The following compounds Ia-60 to Ia-62 were synthesized according to the synthesis method of the compound Ia-46 using corresponding carboxylic acid instead of 2-(4-fluorophenyl)-4-quinolinecarboxylic acid.

Example 54

N-[5-(2-furyl)-1,3,4-oxadiazol-2-yl]-2-(1-naphthyl)-4-quinolinecarboxamide (compound Ia-60)

$^1$H-NMR (DMSO-d$_6$) δ: 8.33 (1H, brd, J=7.9 Hz), 8.28 (1H, d, J=7.9 Hz), 8.20 (1H, d, J=7.9 Hz), 8.15 (1H, s), 8.12-8.08 (2H, m), 8.06 (1H, dd, J=1.7 Hz), 7.94-7.87 (2H, m), 7.78 (1H, m), 7.71 (1H, m), 7.62-7.55 (2H, m), 7.29 (1H, d, J=3.4 Hz), 6.80 (1H, dd, J=3.4 Hz, 1.7 Hz).
ES-MS (m/z): 433 (M+H)$^+$.

Example 55

N-[5-(2-furyl)-1,3,4-oxadiazol-2-yl]-2-(6-methoxy-2-naphthyl)-quinolinecarboxamide (compound Ia-61)

ES-MS (m/z): 463 (M+H)$^+$.

Example 56

N-[5-(2-furyl)-1,3,4-oxadiazol-2-yl]-2-(2-pyridyl)-4-quinolinecarboxamide (compound Ia-62)

$^1$H-NMR (DMSO-d$_6$) δ: 8.85 (1H, s), 8.82 (1H, d, J=4.5 Hz), 8.67 (1H, d, J=7.9 Hz), 8.29 (1H, brs), 8.25 (1H, d, J=8.5 Hz), 8.09 (1H, m), 8.09 (1H, d, J=1.7 Hz), 7.93 (1H, m), 7.77 (1H, m), 7.60 (1H, m), 7.33 (1H, d, J=3.4 Hz), 6.83 (1H, dd, J=3.4 Hz, 1.7 Hz).
ES-MS (m/z): 384 (M+H)$^+$.

Example 57

N-[5-(2-furyl)-1,3,4-oxadiazol-2-yl]-2-(3-pyridyl)-4-quinolinecarboxamide (compound Ia-63)

The title compound was synthesized according to the synthesis method of Production Example 1 using commercially available 2-(3-pyridyl)-4-quinolinecarboxylic acid instead of 2-phenyl-4-quinolinecarboxylic acid.
ES-MS (m/z): 384 (M+H)$^+$.

The following compounds Ia-64 and Ia-65 were synthesized according to the synthesis method of the compound Ia-46 using corresponding carboxylic acid instead of 2-(4-fluorophenyl)-4-quinolinecarboxylic acid.

Example 58

N-[5-(2-furyl)-1,3,4-oxadiazol-2-yl]-2-(5-methyl-2-furyl)-4-quinolinecarboxamide (compound Ia-64)

ES-MS (m/z): 387 (M+H)$^+$.

Example 59

N-[5-(2-furyl)-1,3,4-oxadiazol-2-yl]-2-trans-styryl-4-quinolinecarboxamide (compound Ia-65)

$^1$H-NMR (DMSO-d$_6$) δ: 8.26 (1H, s), 8.18 (1H, brs), 8.12-8.09 (2H, m), 7.96 (1H, d, J=15.9 Hz), 7.86 (1H, dd, J=7.9 Hz, 7.4 Hz), 7.78 (2H, d, J=7.4 Hz), 7.68 (1H, dd, J=7.4 Hz, 7.4 Hz), 7.57 (1H, d, J=15.9 Hz), 7.47 (2H, dd, J=7.9 Hz, 7.4 Hz), 7.40 (1H, d, J=7.4 Hz), 7.33 (1H, brs), 6.83 (1H, brs).
ES-MS (m/z): 409 (M+H)$^+$.

Example 60

N-[5-(2-furyl)-1,3,4-oxadiazol-2-yl]-3-methyl-2-phenyl-4-quinolinecarboxamide (compound Ia-66)

The title compound was synthesized according to the method of Production Example 1 using commercially available 3-methyl-2-phenyl-4-quinolinecarboxylic acid instead of 2-phenyl-4-quinolinecarboxylic acid.
$^1$H-NMR (DMSO-$d_6$) δ: 8.10-8.01 (2H, m), 7.87-7.49 (8H, m), 7.24 (1H, d, J=3.4 Hz), 6.77 (1H, brs), 2.38 (3H, s).
ES-MS (m/z): 397 (M+H)$^+$.

Example 61

6-fluoro-N-[5-(2-furyl)-1,3,4-oxadiazol-2-yl]-2-phenyl-4-quinolinecarboxamide (compound Ia-67)

The title compound was synthesized according to the synthesis method of the compound Ia-46 using 6-fluoro-2-phenyl-4-quinolinecarboxylic acid described in Reference Example 17, HBTU, and HOBt instead of 2-(4-fluorophenyl)-4-quinolinecarboxylic acid, HATU, and HOAt, respectively.
$^1$H-NMR (DMSO-$d_6$) δ: 12.71 (1H, s), 8.55 (1H, d, J=4.0 Hz), 8.23-8.35 (3H, m), 8.07 (1H, s), 7.81 (1H, s), 7.71 (1H, d, J=8.2 Hz), 7.51-7.60 (3H, s), 7.31 (1H, d, J=3.3 Hz), 6.81 (1H, dd, J=3.3 Hz, 1.8 Hz).
FAB-MS (m/z): 401 (M+H)$^+$.

Example 62

6-bromo-N-[5-(2-furyl)-1,3,4-oxadiazol-2-yl]-2-phenyl-4-quinolinecarboxamide (compound Ia-68)

The title compound was synthesized according to the synthesis method of Production Example 1 using commercially available 6-bromo-2-phenyl-4-quinolinecarboxylic acid instead of 2-phenyl-4-quinolinecarboxylic acid.
ES-MS (m/z): 463 ($^{81}$BrM+H)$^+$, 461 ($^{79}$BrM+H)$^+$.

Example 63

N-[5-(2-furyl)-1,3,4-oxadiazol-2-yl]-6-iodo-2-phenyl-4-quinolinecarboxamide (compound Ia-69)

The title compound was synthesized according to the synthesis method of the compound Ia-46 using 6-iodo-2-phenyl-4-quinolinecarboxylic acid described in Reference Example 18, HBTU, and HOBt instead of 2-(4-fluorophenyl)-4-quinolinecarboxylic acid, HATU, and HOAt, respectively.
$^1$H-NMR (DMSO-$d_6$) δ: 8.69 (1H, brs), 8.54 (1H, s), 8.36 (2H, d, J=7.4 Hz), 8.15 (1H, dd, J=9.1 Hz, 1.7 Hz), 8.09 (1H, d, J=1.7 Hz), 7.97 (1H, d, J=9.1 Hz), 7.63-7.56 (3H, m), 7.34 (1H, d, J=3.4 Hz), 6.83 (1H, dd, J=3.4 Hz, 1.7 Hz).
ES-MS (m/z): 509 (M+

Example 64

N-[5-(2-furyl)-1,3,4-oxadiazol-2-yl]-6-methyl-2-phenyl-4-quinolinecarboxamide (compound Ia-70)

The title compound was synthesized according to the synthesis method of the compound Ia-31 using commercially available 6-methyl-2-phenyl-4-quinolinecarboxylic acid instead of 2-phenyl-4-quinolinecarboxylic acid.
ES-MS (m/z): 397 (M+H)$^+$.

The following compounds Ia-71 to Ia-73 were synthesized according to the synthesis method of the compound Ia-46 using corresponding carboxylic acid, commercially available amine, HBTU, and HOBt instead of 2-(4-fluorophenyl)-4-quinolinecarboxylic acid, HATU, and HOAt, respectively.

Example 65

N-[5-(2-furyl)-1,3,4-oxadiazol-2-yl]-2-phenyl-6-trifluoromethoxy-4-quinolinecarboxamide (compound Ia-71)

$^1$H-NMR (DMSO-$d_6$) δ: 8.64 (1H, s), 8.38 (2H, d, J=8.5 Hz), 8.33 (1H, d, J=9.1 Hz), 8.31 (1H, brs), 8.08 (1H, d, J=1.7 Hz), 7.89 (1H, dd, J=9.1 Hz, 2.3 Hz), 7.64-7.57 (3H, m), 7.33 (1H, d, J=3.4 Hz), 6.83 (1H, dd, J=3.4 Hz, 1.7 Hz).
ES-MS (m/z): 467 (M+H)$^+$.

Example 66

7-chloro-N-[5-(2-furyl)-1,3,4-oxadiazol-2-yl]-2-phenyl-4-quinolinecarboxamide (compound Ia-72)

$^1$H-NMR (DMSO-$d_6$) δ: 12.91 (1H, s), 8.53 (1H, s), 8.34 (2H, d, J=6.2 Hz), 8.30 (1H, s), 8.23 (1H, d, J=1.8 Hz), 8.07 (1H, s), 7.73 (1H, dd, J=9.1 Hz, 2.1 Hz), 7.59 (3H, d, J=7.7 Hz), 7.30 (1H, d, J=3.3 Hz), 6.80 (1H, dd, J=3.3 Hz, 1.8 Hz).
FAB-MS (m/z): 417 (M+H)$^+$.

Example 67

8-chloro-N-[5-(2-furyl)-1,3,4-oxadiazol-2-yl]-2-phenyl-4-quinolinecarboxamide (compound Ia-73)

$^1$H-NMR (DMSO-$d_6$) δ: 12.90 (1H, s), 8.62 (1H, s), 8.42 (1H, d, J=6.6 Hz), 8.37 (1H, d, J=6.2 Hz), 8.21 (1H, d, J=7.7 Hz), 8.07 (2H, d, J=5.9 Hz), 7.57-7.70 (4H, m), 7.31 (1H, d, J=3.3 Hz), 6.80 (1H, dd, J=3.3 Hz, 1.8 Hz),
FAB-MS (m/z): 417 (M+H)$^+$.

Example 68

6,8-dichloro-N-[5-(2-furyl)-1,3,4-oxadiazol-2-yl]-2-phenyl-4-quinolinecarboxamide (compound Ia-74)

The title compound was synthesized according to the synthesis method of the compound Ia-46 using commercially available 6,8-dichloro-2-phenyl-4-quinolinecarboxylic acid instead of 2-(4-fluorophenyl)-4-quinolinecarboxylic acid.
$^1$H-NMR (DMSO-$d_6$) δ: 8.68 (1H, s), 8.42 (2H, d, J=8.5 Hz), 8.33 (1H, brs), 8.23 (1H, d, J=2.3 Hz), 8.07 (1H, d, J=1.7 Hz), 7.63-7.59 (3H, m), 7.32 (1H, d, J=3.4 Hz), 6.82 (1H, dd, J=3.4 Hz, 1.7 Hz).
ES-MS (m/z): 453 ($^{37}$Cl$^{35}$ClM+H)$^+$, 451 ($^{35}$Cl$^{35}$ClM+H)$^+$.

The following compounds Ia-75 and Ia-76 were synthesized according to the synthesis method of the compound Ia-16 using the compound Ia-69 instead of the compound Ia-12 and corresponding boronic acid instead of 3-nitrophenylboronic acid.

Example 69

N-[5-(2-furyl)-1,3,4-oxadiazol-2-yl]-2,6-diphenyl-4-quinolinecarboxamide (compound Ia-75)

ES-MS (m/z): 459 (M+H)$^+$.

Example 70

N-[5-(2-furyl)-1,3,4-oxadiazol-2-yl]-2-phenyl-6-(4-pyridyl)-4-quinolinecarboxamide (compound Ia-76)

$^1$H-NMR (DMSO-d$_6$) δ: 9.33 (1H, brs), 8.50 (3H, br), 8.24-8.09 (4H, brm), 7.86 (1H, brs), 7.69 (2H, brs), 7.57-7.51 (3H, brm), 7.09 (1H, brs), 6.68 (1H, brs).
ES-MS (m/z): 460 (M+H)$^+$.

The following compounds Ia-77 and Ia-78 were synthesized according to the synthesis method of Production Example 1 using corresponding carboxylic acid instead of 2-phenyl-4-quinolinecarboxylic acid.

Example 71

6-chloro-2-(4-chlorophenyl)-N-[5-(2-furyl)-1,3,4-oxadiazol-2-yl]-4-quinolinecarboxamide (compound Ia-77)

$^1$H-NMR (DMSO-d$_6$) δ: 8.54 (1H, s), 8.47 (1H, brs), 8.36 (2H, d, J=8.3 Hz), 8.18 (1H, d, J=8.8 Hz), 8.01 (1H, d, J=2.0 Hz), 7.87 (1H, d, J=8.8 Hz), 7.65 (2H, d, J=8.3 Hz), 7.25 (1H, d, J=3.4 Hz), 6.78 (1H, dd, J=3.4 Hz, 2.0 Hz).
ES-MS (m/z): 453 ($^{37}$Cl$^{35}$ClM+H)$^+$, 451 ($^{35}$Cl$^{35}$ClM+H)$^+$.

Example 72

6-bromo-N-[5-(2-furyl)-1,3,4-oxadiazol-2-yl]-2-(5-methyl-2-thienyl)-4-quinolinecarboxamide (compound Ia-78)

$^1$H-NMR (DMSO-d$_6$) δ: 8.49 (1H, brs), 8.37 (1H, s), 8.00 (1H, d, J=1.5 Hz), 7.92-7.86 (3H, m), 7.24 (1H, d, J=3.4 Hz), 6.95 (1H, d, J=3.9 Hz), 6.77 (1H, dd, J=3.4 Hz, 1.5 Hz), 2.53 (3H, s).
ES-MS (m/z): 483 ($^{81}$BrM+H)$^+$, 481 ($^{79}$BrM+H)$^+$.

The following compounds Ia-79 to Ia-83 were synthesized according to the synthesis method of the compound Ia-46 using corresponding carboxylic acid and commercially available amine instead of 2-(4-fluorophenyl)-4-quinolinecarboxylic acid and 2-amino-5-(2-furyl)-1,3,4-oxadiazole, respectively.

Example 73

8-chloro-2-(2-furyl)-N-[5-(2-furyl)-1,3,4-oxadiazol-2-yl]-4-quinolinecarboxamide (compound Ia-79)

$^1$H-NMR (DMSO-d$_6$) δ: 8.36 (1H, s), 8.14 (1H, brs), 8.07-8.04 (3H, m), 7.63 (1H, t, J=7.9 Hz), 7.54 (1H, d, J=3.4 Hz), 7.31 (1H, s), 6.80 (2H, brs).
ES-MS (m/z): 409 ($^{37}$ClM+H)$^+$, 407 ($^{35}$ClM+H)$^+$.

Example 74

N-[5-(2-furyl)-1,3,4-oxadiazol-2-yl]-7-methyl-2-phenyl-4-quinolinecarboxamide (compound Ia-80)

$^1$H-NMR (DMSO-d$_6$) δ: 8.41 (1H, s), 8.35 (2H, d, J=7.4 Hz), 8.17 (1H, brd, J=8.5 Hz), 8.08 (1H, d, J=1.7 Hz), 8.00 (1H, s), 7.62-7.54 (4H, m), 7.32 (1H, d, J=3.4 Hz), 6.83 (1H, dd, J=3.4 Hz, 1.7 Hz), 2.59 (3H, s).
ES-MS (m/z): 397 (M+H)$^+$.

Production Example 11

N-(5-methyl-1,3,4-oxadiazol-2-yl)-2-phenyl-4-quinolinecarboxamide (compound Ia-81)

$^1$H-NMR (DMSO-d$_6$) δ: 8.45 (1H, s), 8.36 (2H, d, J=7.4 Hz), 8.20-8.18 (2H, m), 7.88 (1H, dd, J=8.5 Hz, 7.4 Hz), 7.71 (1H, dd, J=7.9 Hz, 7.4 Hz), 7.62-7.56 (3H, m), 2.55 (3H, s).
ES-MS (m/z): 331 (M+H)$^+$.

Production Example 12

N-(5-ethyl-1,3,4-oxadiazol-2-yl)-2-phenyl-4-quinolinecarboxamide (compound Ia-82)

$^1$H-NMR (DMSO-d$_6$) δ: 12.50 (1H, brs), 8.45 (1H, s), 8.36 (2H, d, J=7.4 Hz), 8.20-8.18 (2H, m), 7.88 (1H, dd, J=8.5 Hz, 6.8 Hz), 7.71 (1H, dd, J=8.5 Hz, 7.4 Hz), 7.62-7.54 (3H, m), 2.90 (2H, q, J=7.4 Hz), 1.31 (3H, t, J=7.4 Hz).
ES-MS (m/z): 345 (M+H)$^+$.

Production Example 13

N-(5-benzyl-1,3,4-oxadiazol-2-yl)-2-phenyl-4-quinolinecarboxamide (compound Ia-83)

$^1$H-NMR (DMSO-d$_6$) δ: 12.53 (1H, br), 8.43 (1H, s), 8.34 (2H, d, J=7.8 Hz), 8.18-8.16 (2H, m), 7.86 (1H, dd, J=8.3 Hz, 7.3 Hz), 7.69 (1H, dd, J=8.3 Hz, 7.3 Hz), 7.61-7.52 (3H, m), 7.41-7.29 (5H, m), 4.30 (2H, s).
ES-MS (m/z): 407 (M+H)$^+$.

The following compounds Ia-84 and Ia-85 were synthesized according to the method of Production Example 1 using corresponding commercially available amine instead of 2-amino-5-(2-furyl)-1,3,4-oxadiazole.

Production Example 14

N-[5-(5-nitro-2-furyl)-1,3,4-oxadiazol-2-yl]-2-phenyl-4-quinolinecarboxamide (compound Ia-84)

$^1$H-NMR (DMSO-d$_6$) δ: 8.60 (1H, s), 8.39 (2H, d, J=8.5 Hz), 8.30 (1H, d, J=7.9 Hz), 8.22 (1H, d, J=7.9 Hz), 7.95 (1H, d, J=4.0 Hz), 7.90 (1H, m), 7.73 (1H, m), 7.71 (1H, d, J=4.0 Hz), 7.64-7.58 (3H, m).

Production Example 15

N-(5-ethoxycarbonyl-1,3,4-oxadiazol-2-yl)-2-phenyl-4-quinolinecarboxamide (compound Ia-85)

$^1$H-NMR (DMSO-d$_6$) δ: 8.49 (1H, s), 8.36 (2H, d, J=7.4 Hz), 8.26 (1H, d, J=8.5 Hz), 8.20 (1H, d, J=8.5 Hz), 7.89 (1H, dd, J=8.5 Hz, 7.4 Hz), 7.72 (1H, dd, J=8.5 Hz, 7.4 Hz), 7.63-7.56 (3H, m), 4.46 (2H, q, J=6.8 Hz), 1.37 (3H, t, J=6.8 Hz).
ES-MS (m/z): 389 (M+H)$^+$.

Production Example 16

N-(5-morpholino-1,3,4-oxadiazol-2-yl)-2-phenyl-4-quinolinecarboxamide (compound Ia-86)

The title compound was synthesized according to the synthesis method of the compound Ia-46 using commercially available 2-amino-5-morpholino-1,3,4-oxadiazole instead of 2-amino-5-(2-furyl)-1,3,4-oxadiazole.

¹H-NMR (CDCl₃) δ: 8.45-8.10 (5H, brm), 7.72-7.42 (5H, brm), 4.24-3.49 (8H, brm).
ES-MS (m/z): 402 (M+H)⁺.

Example 75

N-[5-(2-furyl)-1,3,4-oxadiazol-2-yl]-6-hydroxy-2-phenyl-4-quinolinecarboxamide (compound Ia-87)

A saturated aqueous solution of sodium bicarbonate (1.5 mL) was added in small portions to a methanol (6.7 mL) solution of a compound Ia-91 (0.1476 g, 0.335 mmol) described later, and the mixture was stirred at room temperature for 3 hours. The reaction solution was subjected to extraction with dichloromethane, washed with saturated saline, and dried over anhydrous sodium sulfate, and then, the solvent was distilled off. The obtained residue was fractionated by silica gel column chromatography, and the solvent was distilled off to obtain the title compound (0.0856 g, 0.215 mmol) as a pale yellow powder.

¹H-NMR (DMSO-d₆) δ: 12.74 (1H, brs), 10.31 (1H, s), 8.37 (1H, s), 8.32-8.28 (2H, m), 8.08-8.03 (2H, m), 7.59-7.48 (4H, m), 7.41 (1H, dd, J=9.0, 2.4 Hz), 7.30 (1H, d, J=3.4 Hz), 6.82 (1H, m).
ES-MS (m/z): 399 (M+H)⁺.

Example 76

N-[5-(2-furyl)-1,3,4-oxadiazol-2-yl]-6-[2-(dimethylamino)ethoxy]-2-phenyl-4-quinolinecarboxamide (compound Ia-88)

Dimethylaminoethanol (0.0334 g, 0.375 mmol) and triphenylphosphine (0.0984 g, 0.375 mmol) were added to a tetrahydrofuran (5.0 mL) solution of the compound Ia-87 (0.0996 g, 0.250 mmol). To the mixture a toluene solution (171 μL) of 2.2 mmol/L azodicarboxylic acid diethyl ester was added in small portions, and the mixture was stirred at room temperature for 15 hours. The solvent was distilled off. The obtained residue was fractionated by silica gel column chromatography, and the solvent was distilled off to obtain the title compound (0.0434 g, 0.0924 mmol) as a pale yellow powder.

¹H-NMR (CDCl₃) δ: 8.66 (1H, d, J=2.8 Hz), 8.52 (1H, s), 8.17-8.15 (2H, m), 8.04 (1H, d, J=9.2 Hz), 7.61 (1H, s), 7.50-7.54 (2H, m), 7.46-7.44 (1H, m), 7.31-7.27 (1H, m), 7.16 (1H, d, J=3.6 Hz), 6.56 (1H, s), 4.33 (2H, t, J=7.0 Hz), 3.00 (2H, t, J=7.0 Hz), 2.44 (6H, s).
ES-MS (m/z): 470 (M+H)⁺.

Example 77

N-[5-(2-furyl)-1,3,4-oxadiazol-2-yl]-6-(2-methoxyethoxy)-2-phenyl-4-quinolinecarboxamide (compound Ia-89)

The title compound was synthesized according to the synthesis method of the compound Ia-88 using methoxyethanol instead of dimethylaminoethanol.

¹H-NMR (CDCl₃) δ: 8.62 (1H, d, J=2.8 Hz), 8.58 (1H, s), 8.17-8.15 (2H, m), 8.12-8.09 (1H, m), 7.60 (1H, s), 7.54-7.45 (3H, m), 7.37-7.34 (1H, m), 7.18 (1H, d, J=3.6 Hz), 6.53 (1H, s), 4.29 (2H, t, J=5.2 Hz), 3.88 (2H, t, J=5.2 Hz), 3.41 (3H, s).
ES-MS (m/z): 457 (M+H)⁺.

Example 78

6-benzyloxy-N-[5-(2-furyl)-1,3,4-oxadiazol-2-yl]-2-phenyl-4-quinolinecarboxamide (compound Ia-90)

The title compound was synthesized according to the synthesis method of the compound Ia-88 using benzyl alcohol instead of dimethylaminoethanol.

¹H-NMR (CDCl₃) δ: 8.72 (1H, d, J=2.7 Hz), 8.64 (1H, s), 8.18-8.11 (3H, m), 7.57-7.32 (10H, m), 7.17 (1H, d, J=3.7 Hz), 6.51 (1H, m), 5.26 (2H, s).
ES-MS (m/z): 489 (M+H)⁺.

Example 79

6-acetoxy-N-[5-(2-furyl)-1,3,4-oxadiazol-2-yl]-2-phenyl-4-quinolinecarboxamide (compound Ia-91)

The title compound was synthesized according to the method of Production Example 1 using 6-acetoxy-2-phenyl-4-quinolinecarboxylic acid described in Reference Example 21 instead of 2-phenyl-4-quinolinecarboxylic acid.

¹H-NMR (DMSO-d₆) δ: 12.73 (1H, brs), 8.55 (1H, s), 8.35-8.23 (3H, m), 8.23 (1H, d, J=9.0 Hz), 8.08-8.03 (1H, m), 7.70 (1H, dd, J=9.1 Hz, 2.6 Hz), 7.64-7.54 (3H, m), 7.35 (1H, d, J=3.5 Hz), 6.82 (1H, dd, J=3.5 Hz, 1.8 Hz), 2.35 (3H, s).
ES-MS (m/z): 441 (M+H)⁺.

The following compounds Ia-92 to Ia-94 were synthesized according to the synthesis method of the compound Ia-46 using corresponding carboxylic acid, HBTU, and HOBt instead of 2-(4-fluorophenyl)-4-quinolinecarboxylic acid, HATU, and HOAt, respectively.

Example 80

6-acetylamino-N-[5-(2-furyl)-1,3,4-oxadiazol-2-yl]-2-phenyl-4-quinolinecarboxamide (compound Ia-92)

¹H-NMR (DMSO-d₆) δ: 10.28 (1H, s), 8.82 (1H, s), 8.25 (1H, s), 8.14 (1H, d, J=2.4 Hz), 8.06 (1H, d, J=3.4 Hz), 8.01 (1H, d, J=3.4 Hz), 8.07 (1H, s), 7.93 (1H, s), 7.50-7.41 (3H, m), 7.08 (1H, d, J=3.3 Hz), 6.72 (1H, dd, J=3.3 Hz, 1.8 Hz), 2.08 (3H, s).
FAB-MS (m/z): 440 (M+H)⁺.

Example 81

N-[5-(2-furyl)-1,3,4-oxadiazol-2-yl]-2-phenyl-6-propionylamino-4-quinolinecarboxamide (compound Ia-93)

¹H-NMR (DMSO-d₆) δ: 10.19 (1H, s), 8.82 (1H, s), 8.08-8.20 (4H, m), 8.00 (1H, s), 7.91 (1H, s), 7.51-7.45 (3H, m), 7.05 (1H, d, J=3.3 Hz), 6.71 (1H, dd, J=3.3 Hz, 1.8 Hz), 2.38 (2H, q, J=7.6 Hz), 1.09 (3H, t, J=7.6 Hz).
FAB-MS (m/z): 454 (M+H)⁺.

Example 82

6-butyrylamino-N-[5-(2-furyl)-1,3,4-oxadiazol-2-yl]-2-phenyl-4-quinolinecarboxamide (compound Ia-94)

¹H-NMR (DMSO-d₆) δ: 10.24 (1H, s), 8.77 (1H, s), 8.27 (1H, s), 8.21 (2H, d, J=7.0 Hz), 8.08-8.03 (2H, m), 8.01 (1H, s), 7.55-7.46 (4H, m), 7.11 (1H, d, J=3.3 Hz), 6.74 (1H, dd, J=3.3 Hz, 1.8 Hz), 2.34 (2H, q, J=8.3 Hz), 1.66-1.56 (2H, m), 0.91 (3H, t, J=7.3 Hz).

FAB-MS (m/z): 468 (M+H)$^+$.

Example 83

6-cyano-N-[5-(2-furyl)-1,3,4-oxadiazol-2-yl]-2-phenyl-4-quinolinecarboxamide (compound Ia-95)

HOBt (0.0351 g, 0.260 mmol) and 1-ethyl-3-(3-dimethylaminopropyl)carbodiimide (EDC) (0.0460 g, 0.240 mmol) were added to a dimethylformamide (5.0 mL) solution of 6-cyano-2-phenyl-4-quinolinecarboxylic acid (0.0548 g, 0.200 mmol) described in Reference Example 22 and triethylamine (0.0223 g, 0.220 mmol), and the mixture was stirred at room temperature for 30 minutes. Commercially available 2-amino-5-(2-furyl)-1,3,4-oxadiazole (0.0332 g, 0.220 mmol) was added thereto, and the mixture was stirred at room temperature. The reaction solution was subjected to extraction with dichloromethane, washed with water and saturated saline, and dried over anhydrous sodium sulfate, and then, the solvent was distilled off. The obtained residue was fractionated by silica gel column chromatography, and the solvent was distilled off to obtain the title compound (0.001 g, 0.0024 mmol) as an amorphous substance.

ES-MS (m/z): 408 (M+H)$^+$.

The following compounds Ia-96 to Ia-100 were synthesized according to the synthesis method of the compound Ia-16 using the compound Ia-69 instead of the compound Ia-12 and corresponding boronic acid instead of 3-nitrophenylboronic acid.

Example 84

6-(2-fluorophenyl)-N-[5-(2-furyl)-1,3,4-oxadiazol-2-yl]-2-phenyl-4-quinolinecarboxamide (compound Ia-96)

ES-MS (m/z): 477 (M+H)$^+$.

Example 85

6-(4-fluorophenyl)-N-[5-(2-furyl)-1,3,4-oxadiazol-2-yl]-2-phenyl-4-quinolinecarboxamide (compound Ia-97)

ES-MS (m/z): 477 (M+H)$^+$.

Example 86

N-[5-(2-furyl)-1,3,4-oxadiazol-2-yl]-6-(4-hydroxyphenyl)-2-phenyl-4-quinolinecarboxamide (compound Ia-98)

$^1$H-NMR (DMSO-d$_6$) δ: 9.15 (2H, brs), 8.43 (1H, brs), 8.19 (2H, brd, J=6.8 Hz), 8.10 (1H, brd, J=8.3 Hz), 7.98 (1H, brd, J=6.8 Hz), 7.82 (1H, brs), 7.60 (2H, brd, J=8.3 Hz), 7.53-7.45 (3H, m), 7.04 (1H, brs), 6.83 (2H, brd, J=8.3 Hz), 6.66 (1H, brs).

ES-MS (m/z): 475 (M+H)$^+$.

Example 87

N-[5-(2-furyl)-1,3,4-oxadiazol-2-yl]-6-(3-thienyl)-2-phenyl-4-quinolinecarboxamide (compound Ia-99)

$^1$H-NMR (DMSO-d$_6$) δ: 9.30 (1H, brs), 8.47 (1H, brs), 8.19 (2H, brd, J=7.3 Hz), 8.09 (2H, brs), 7.85-7.84 (2H, brs), 7.59 (1H, brs), 7.54-7.47 (4H, m), 7.07 (1H, brs), 6.67 (1H, brs).

ES-MS (m/z): 465 (M+H)$^+$.

Example 88

N-[5-(2-furyl)-1,3,4-oxadiazol-2-yl]-6-(3-pyridyl)-2-phenyl-4-quinolinecarboxamide (compound Ia-100)

$^1$H-NMR (DMSO-d$_6$) δ: 9.34 (1H, brs), 8.98 (1H, brs), 8.50 (2H, brs), 8.21 (2H, brd, J=7.3 Hz), 8.17 (1H, brd, J=8.8 Hz), 8.07 (2H, brs), 7.81 (1H, brs), 7.54-7.49 (3H, m), 7.34 (1H, br), 7.02 (1H, brs), 6.65 (1H, brs).

ES-MS (m/z): 460 (M+H)$^+$.

Example 89

2-(2-acetylaminophenyl)-N-[5-(2-furyl)-1,3,4-oxadiazol-2-yl]-4-quinolinecarboxamide (compound Ia-101)

The compound Ia-40 was acetylated by a routine method to obtain the title compound.

ES-MS (m/z): 440 (M+H)$^+$.

Example 90

N-[5-(2-furyl)-1,3,4-oxadiazol-2-yl]-2-(2-methanesulfonylaminophenyl)-4-quinolinecarboxamide (compound Ia-102)

The compound Ia-40 was methanesulfonylated by a routine method to obtain the title compound.

ES-MS (m/z): 476 (M+H)$^+$.

Example 91

2-(4-aminophenyl)-N-[5-(2-furyl)-1,3,4-oxadiazol-2-yl]-4-quinolinecarboxamide (compound Ia-103)

The compound Ia-52 was subjected to catalytic reduction by a routine method to obtain the title compound.

ES-MS (m/z): 398 (M+H)$^+$.

The following compounds Ia-104 and Ia-105 were synthesized according to the synthesis method of the compound Ia-46 using corresponding carboxylic acid, HBTU, and HOBt instead of 2-(4-fluorophenyl)-4-quinolinecarboxylic acid, HATU, and HOAt, respectively.

Example 92

2-(4-acetylphenyl)-N-[5-(2-furyl)-1,3,4-oxadiazol-2-yl]-4-quinolinecarboxamide (compound Ia-104)

ES-MS (m/z): 425 (M+H)$^+$.

Example 93

N-[5-(2-furyl)-1,3,4-oxadiazol-2-yl]-2-(4-methylthiophenyl)-4-quinolinecarboxamide (compound Ia-105)

ES-MS (m/z): 429 (M+H)$^+$.

Example 94

N-[5-(2-furyl)-1,3,4-oxadiazol-2-yl]-2-(4-methanesulfonylphenyl)-4-quinolinecarboxamide (compound Ia-106)

The compound Ia-105 was oxidized with mCPBA to obtain the title compound.
ES-MS (m/z): 461 (M+H)$^+$.

The following compounds Ia-107 to Ia-120 were synthesized according to the synthesis method of the compound Ia-46 using corresponding carboxylic acid and commercially available amine instead of 2-(4-fluorophenyl)-4-quinolinecarboxylic acid and 2-amino-5-(2-furyl)-1,3,4-oxadiazole, respectively.

Production Example 17

N-[5-(2-furyl)-1,3,4-oxadiazol-2-yl]-2-(2-thienyl)-4-quinolinecarboxamide (compound Ia-107)

ES-MS (m/z): 389 (M+H)$^+$.

Example 95

N-[5-(2-furyl)-1,3,4-oxadiazol-2-yl]-6,8-dimethyl-2-(5-methyl-2-thienyl)-4-quinolinecarboxamide (compound Ia-108)

ES-MS (m/z): 431 (M+H)$^+$.

Example 96

2-(5-ethyl-2-thienyl)-N-[5-(2-furyl)-1,3,4-oxadiazol-2-yl]-6,8-dimethyl-4-quinolinecarboxamide (compound Ia-109)

ES-MS (m/z): 445 (M+H)$^+$.

Example 97

6-chloro-2-phenyl-N-(5-phenyl-1,3,4-oxadiazol-2-yl)-4-quinolinecarboxamide (compound Ia-110)

$^1$H-NMR (DMSO-d$_6$) δ: 8.59 (1H, s), 8.41 (1H, brs), 8.37 (2H, d, J=6.8 Hz), 8.21 (1H, d, J=9.1 Hz), 8.01-8.00 (2H, m), 7.91 (1H, dd, J=9.1 Hz, 2.3 Hz), 7.65-7.57 (6H, m).
ES-MS (m/z): 429 ($^{37}$ClM+H)$^+$, 427 ($^{35}$ClM+H)$^+$.

Example 98

N-(5-phenyl-1,3,4-oxadiazol-2-yl)-2-phenyl-6-trifluoromethoxy-4-quinolinecarboxamide (compound Ia-111)

$^1$H-NMR (DMSO-d$_6$) δ: 12.86 (1H, br), 8.65 (1H, s), 8.39-8.32 (4H, m), 8.01-8.00 (2H, m), 7.88 (1H, d, J=9.3 Hz), 7.65-7.56 (6H, m).
ES-MS (m/z): 477 (M+H)$^+$.

Example 99

6-chloro-N-[5-(2-chlorophenyl)-1,3,4-oxadiazol-2-yl]-2-phenyl-4-quinolinecarboxamide (compound Ia-112)

$^1$H-NMR (DMSO-d$_6$) δ: 8.58 (1H, s), 8.40-8.36 (3H, m), 8.21 (1H, d, J=8.5 Hz), 7.99 (1H, d, J=9.1 Hz), 7.95 (1H, s), 7.91 (1H, dd, J=9.1 Hz, 2.3 Hz), 7.75 (1H, dd, J=7.9 Hz, 1.1 Hz), 7.67 (1H, ddd, J=7.9 Hz, 7.9 Hz, 1.1 Hz), 7.63-7.57 (3H, m).
ES-MS (m/z): 463 ($^{37}$ClM+H)$^+$, 461 ($^{35}$ClM+H)$^+$.

Example 100

N-[5-(2-chlorophenyl)-1,3,4-oxadiazol-2-yl]-2-phenyl-6-trifluoromethoxy-4-quinolinecarboxamide (compound Ia-113)

$^1$H-NMR (DMSO-d$_6$) δ: 12.95 (1H, br), 8.65 (1H, s), 8.39-8.32 (4H, m), 8.01 (2H, d, J=8.3 Hz), 7.89 (1H, d, J=9.3 Hz), 7.72 (2H, d, J=7.8 Hz), 7.65-7.57 (3H, m).
ES-MS (m/z): 513 ($^{37}$ClM+H)$^+$, 511 ($^{35}$ClM+H)$^+$.

Example 101

6-chloro-N-[5-(4-chlorophenyl)-1,3,4-oxadiazol-2-yl]-2-phenyl-4-quinolinecarboxamide (compound Ia-114)

$^1$H-NMR (DMSO-d$_6$) δ: 8.58 (1H, s), 8.41 (1H, brs), 8.36 (2H, d, J=7.4 Hz), 8.21 (1H, d, J=9.1 Hz), 8.01 (2H, d, J=8.5 Hz), 7.91 (1H, dd, J=9.1 Hz, 2.3 Hz), 7.72 (2H, d, J=9.1 Hz), 7.53-7.57 (3H, m).
ES-MS (m/z): 463 ($^{37}$ClM+H)$^+$, 461 ($^{35}$ClM+H)$^+$.

Example 102

N-[5-(4-chlorophenyl)-1,3,4-oxadiazol-2-yl]-2-phenyl-6-trifluoromethoxy-4-quinolinecarboxamide (compound Ia-115)

ES-MS (m/z): 513 ($^{37}$ClM+H)$^+$, 511 ($^{35}$ClM+H)$^+$.

Example 103

6-chloro-N-[5-(4-methoxyphenyl)-1,3,4-oxadiazol-2-yl]-2-phenyl-4-quinolinecarboxamide (compound Ia-116)

$^1$H-NMR (DMSO-d$_6$) δ: 8.58 (1H, s), 8.39 (1H, brs), 8.36 (2H, d, J=7.9 Hz), 8.21 (1H, d, J=9.1 Hz), 7.95-7.90 (3H, m), 7.63-7.57 (3H, m), 7.18 (2H, d, J=9.1 Hz), 3.87 (3H, s).
ES-MS (m/z): 459 ($^{37}$ClM+H)$^+$, 457 ($^{35}$ClM+H)$^+$.

Example 104

N-[5-(4-methoxyphenyl)-1,3,4-oxadiazol-2-yl]-2-phenyl-6-trifluoromethoxy-4-quinolinecarboxamide (compound Ia-117)

$^1$H-NMR (DMSO-d$_6$) δ: 8.65 (1H, s), 8.39 (2H, d, J=7.4 Hz), 8.35-8.33 (2H, m), 7.95 (2H, d, J=8.5 Hz), 7.90 (1H, m), 7.65-7.59 (3H, m), 7.19 (2H, d, J=8.5 Hz), 3.88 (3H, s).
ES-MS (m/z): 507 (M+H)$^+$.

Example 105

6-chloro-N-[5-(4-nitrophenyl)-1,3,4-oxadiazol-2-yl]-2-phenyl-4-quinolinecarboxamide (compound Ia-118)

ES-MS (m/z): 472 (M+H)$^+$.

Example 106

N-[5-(4-nitrophenyl)-1,3,4-oxadiazol-2-yl]-2-phenyl-6-trifluoromethoxy-4-quinolinecarboxamide (compound Ia-119)

ES-MS (m/z): 522 (M+H)$^+$.

Example 107

N-[5-(3-furyl)-1,3,4-oxadiazol-2-yl]-2-phenyl-6-trifluoromethoxy-4-quinolinecarboxamide (compound Ia-120)

$^1$H-NMR (DMSO-d$_6$) δ: 12.82 (1H, br), 8.64 (1H, s), 8.53 (1H, s), 8.43-8.37 (2H, m), 8.33 (2H, d, J=9.3 Hz), 7.98 (1H, s), 7.89 (1H, d, J=8.8 Hz), 7.64-7.58 (3H, m), 7.02 (1H, s).
ES-MS (m/z): 467 (M+H)$^+$.

Example 108

6-chloro-2-phenyl-N-[5-(2-thienyl)-1,3,4-oxadiazol-2-yl]-4-quinolinecarboxamide (compound Ia-121)

The title compound was synthesized according to the synthesis method of a compound Ia-122 described later using 4-(6-chloro-2-phenyl-4-quinolinecarbonyl)-1-(2-thiophenecarbonyl)thiosemicarbazide described in Reference Example 37 instead of 4-(2-phenyl-6-trifluoromethoxy-4-quinolinecarbonyl)-1-(2-thiophenecarbonyl)thiosemicarbazide.
ES-MS (m/z): 435 ($^{37}$ClM+H)$^+$, 433 ($^{35}$ClM+H)$^+$.

Example 109

2-phenyl-N-[5-(2-thienyl)-1,3,4-oxadiazol-2-yl]-6-trifluoromethoxy-4-quinolinecarboxamide (compound Ia-122)

p-toluenesulfonyl chloride (32.7 mg, 0.17 mmol) was added to a pyridine (2 mL) solution of 4-(2-phenyl-6-trifluoromethoxy-4-quinolinecarbonyl)-1-(2-thiophenecarbonyl)thiosemicarbazide (70 mg, 0.14 mmol) described in Reference Example 28, and the mixture was stirred overnight at room temperature. The reaction solution was concentrated. After that, to the residue, water was added, and the deposited crystal was collected by filtration, washed with water, dried, and then purified by silica gel column chromatography to obtain the title compound (16 mg, 0.03 mmol).
ES-MS (m/z): 483 (M+H)$^+$.

The following compounds Ia-123 to Ia-130 were synthesized according to the synthesis method of the compound Ia-122 using corresponding thiosemicarbazide instead of 4-(2-phenyl-6-trifluoromethoxy-4-quinolinecarbonyl)-1-(2-thiophenecarbonyl)thiosemicarbazide.

Production Example 18

N-[5-(3-methyl-2-furyl)-1,3,4-oxadiazol-2-yl]-2-phenyl-4-quinolinecarboxamide (compound Ia-123)

ES-MS (m/z): 397 (M+H)$^+$.

Production Example 19

N-[5-(5-methyl-2-furyl)-1,3,4-oxadiazol-2-yl]-2-phenyl-4-quinolinecarboxamide (compound Ia-124)

ES-MS (m/z): 397 (M+H)$^+$.

Production Example 20

N-[5-(4,5-dimethyl-2-furyl)-1,3,4-oxadiazol-2-yl]-2-phenyl-4-quinolinecarboxamide (compound Ia-125)

ES-MS (m/z): 411 (M+H)$^+$.

Production Example 21

N-[5-(2-benzofuryl)-1,3,4-oxadiazol-2-yl]-2-phenyl-4-quinolinecarboxamide (compound Ia-126)

ES-MS (m/z): 433 (M+H)$^+$.

Production Example 22

N-[5-(2-methyl-4-thiazolyl)-1,3,4-oxadiazol-2-yl]-2-phenyl-4-quinolinecarboxamide (compound Ia-127)

ES-MS (m/z): 414 (M+H)$^+$.

Production Example 23

N-[5-(2,4-dimethyl-5-thiazolyl)-1,3,4-oxadiazol-2-yl]-2-phenyl-4-quinolinecarboxamide (compound Ia-128)

ES-MS (m/z): 427 (M+H)$^+$.

Production Example 24

N-[5-(3-methoxyphenyl)-1,3,4-oxadiazol-2-yl]-2-phenyl-4-quinolinecarboxamide (compound Ia-129)

ES-MS (m/z): 423 (M+H)$^+$.

Production Example 25

N-(5-cyanomethyl-1,3,4-oxadiazol-2-yl)-2-phenyl-4-quinolinecarboxamide (compound Ia-130)

ES-MS (m/z): 356 (M+H)$^+$.

Production Example 26

N-[5-(2-furyl)-1,3,4-oxadiazol-2-yl]-N-methyl-2-phenyl-4-quinolinecarboxamide (compound Ia-131)

The compound Ia-1 (620 mg, 1.62 mmol) was added to a DMF (20 mL) suspension of 60% sodium hydride (102 mg, 2.55 mmol), and the mixture was stirred at 50° C. for 2 hours. The reaction solution was cooled to room temperature. Methyl iodide (434 μL, 6.97 mmol) was added thereto, and the mixture was stirred at room temperature for 1 hour. The reaction solution was concentrated. After that, to the residue, water was added. The mixture was subjected to extraction with methylene chloride and dried over anhydrous sodium sulfate, and then, the solvent was distilled off. The obtained residue was purified by silica gel column chromatography to obtain the title compound.

$^1$H-NMR (CDCl$_3$) δ: 8.21 (1H, d, J=7.9 Hz), 8.10 (2H, dd, J=7.9 Hz, 1.2 Hz), 7.87-7.86 (2H, m), 7.77 (1H, ddd, J=8.5 Hz, 7.3 Hz, 1.2 Hz), 7.58 (1H, ddd, J=8.5 Hz, 7.3 Hz, 1.2 Hz), 7.47-7.53 (3H, m), 7.43 (1H, brs), 7.26-7.24 (1H, m), 6.39 (1H, dd, J=3.7 Hz, 1.8 Hz), 3.77 (3H, s).

ES-MS (m/z): 397 (M+H)$^+$.

Production Example 27

N-[5-(2-tetrahydrofuryl)-1,3,4-oxadiazol-2-yl]-2-phenyl-4-quinolinecarboxamide (compound Ia-132)

The title compound was synthesized according to the synthesis method of the compound Ia-122 using 4-(2-phenyl-4-quinolinecarbonyl)-1-(2-tetrahydrofurancarbonyl)thiosemicarbazide described in Reference Example 38 instead of 4-(2-phenyl-6-trifluoromethoxy-4-quinolinecarbonyl)-1-(2-thiophenecarbonyl)thiosemicarbazide.

ES-MS (m/z): 387 (M+H)$^+$.

The following compounds Ib-1 to Ib-5 were synthesized according to the method of Production Example 1 using corresponding carboxylic acid chloride and commercially available amine instead of 2-phenyl-4-quinolinecarbonyl chloride and 2-amino-5-(2-furyl)-1,3,4-oxadiazole.

Production Example 28

2-phenyl-N-(1,3,4-thiadiazol-2-yl)-4-quinolinecarboxamide (compound Ib-1)

$^1$H-NMR (DMSO-d$_6$) δ: 9.35 (1H, s), 8.53 (1H, s), 8.38 (2H, d, J=8.3 Hz), 8.24-8.19 (2H, m), 7.88 (1H, dd, J=8.3 Hz, 1.2 Hz), 7.70 (1H, dd, J=8.3 Hz, 1.2 Hz), 7.63-7.54 (3H, m).

ES-MS (m/z): 333 (M+H)$^+$.

Production Example 29

N-(5-bromo-1,3,4-thiadiazol-2-yl)-2-phenyl-4-quinolinecarboxamide (compound Ib-2)

$^1$H-NMR (DMSO-d$_6$) δ: 13.86 (1H, brs), 8.54 (1H, s), 8.37 (2H, d, J=8.8 Hz), 8.25 (1H, d, J=8.3 Hz), 8.20 (1H, d, J=8.8 Hz), 7.89 (1H, dd, J=8.3 Hz, 7.3 Hz), 7.71 (1H, dd, J=8.3 Hz, 7.3 Hz), 7.63-7.54 (3H, m).

ES-MS (m/z): 413 ($^{81}$BrM+H)$^+$, 411 ($^{79}$BrM+H)$^+$.

Production Example 30

N-(5-phenyl-1,3,4-thiadiazol-2-yl)-2-phenyl-4-quinolinecarboxamide (compound Ib-3)

$^1$H-NMR (DMSO-d$_6$) δ: 8.57 (1H, s), 8.39 (2H, d, J=8.5 Hz), 8.28 (1H, d, J=8.0 Hz), 8.21 (1H, d, J=8.5 Hz), 8.06-8.03 (2H, m), 7.89 (1H, m), 7.72 (1H, m), 7.64-7.55 (5H, m), 7.39 (1H, m).

ES-MS (m/z): 409 (M+H)$^+$.

Production Example 31

N-[5-(2-furyl)-1,3,4-thiadiazol-2-yl]-2-phenyl-4-quinolinecarboxamide (compound Ib-4)

$^1$H-NMR (DMSO-d$_6$) E: 8.57 (1H, s), 8.39 (2H, d, J=8.0 Hz), 8.28 (1H, d, J=8.5 Hz), 8.20 (1H, d, J=8.5 Hz), 8.02 (1H, s), 7.89 (1H, m), 7.72 (1H, m), 7.64-7.54 (3H, m), 7.32 (1H, d, J=3.4 Hz), 6.79 (1H, m).

ES-MS (m/z): 399 (M+H)$^+$.

Production Example 32

2-phenyl-N-[5-(4-pyridyl)-1,3,4-thiadiazol-2-yl]-4-quinolinecarboxamide (compound Ib-5)

$^1$H-NMR (DMSO-d$_6$) δ: 8.72 (2H, dd, J=4.6 Hz, 1.7 Hz), 8.52 (1H, s), 8.32 (2H, d, J=8.5 Hz), 8.22 (1H, d, J=8.0 Hz), 8.14 (1H, d, J=8.3 Hz), 7.96 (2H, d, J=4.6 Hz, 1.7 Hz), 7.83 (1H, m), 7.65 (1H, m), 7.57-7.48 (3H, m).

ES-MS (m/z): 410 (M+H)$^+$.

The following compounds Ib-6 to Ib-10 were synthesized according to the synthesis method of the compound Ia-46 using corresponding carboxylic acid and commercially available amine instead of 2-(4-fluorophenyl)-4-quinolinecarboxylic acid and 2-amino-5-(2-furyl)-1,3,4-oxadiazole, respectively.

Production Example 33

N-[5-(2-tetrahydrofuryl)-1,3,4-thiadiazol-2-yl]-2-phenyl-4-quinolinecarboxamide (compound Ib-6)

$^1$H-NMR (DMSO-d$_6$) δ: 8.52 (1H, s), 8.38 (2H, d, J=9.1 Hz), 8.24-8.19 (2H, m), 7.89 (1H, ddd, J=8.5 Hz, 7.9 Hz, 1.1 Hz), 7.71 (1H, ddd, J=8.5 Hz, 7.9 Hz, 1.1 Hz), 7.63-7.55 (3H, m), 5.33 (1H, dd, J=7.4 Hz, 5.7 Hz), 4.02 (1H, dd, J=14.7 Hz, 8.5 Hz), 3.90 (1H, dd, J=14.7 Hz, 6.8 Hz), 2.45 (1H, m), 2.16 (1H, m), 2.07-1.98 (2H, m).

ES-MS (m/z): 403 (M+H)$^+$.

Example 110

2-phenyl-6-chloro-N-[5-(4-pyridyl)-1,3,4-thiadiazol-2-yl]-4-quinolinecarboxamide (compound Ib-7)

$^1$H-NMR (500M Hz, DMSO-d$_6$) δ: 8.77 (2H, d, J=5.7 Hz), 8.66 (1H, s), 8.47 (1H, brs), 8.38 (2H, d, J=6.8 Hz), 8.21 (1H, d, J=9.1 Hz), 8.01 (2H, d, J=5.1 Hz), 7.91 (1H, dd, J=9.1 Hz, 2.3 Hz), 7.64-7.58 (3H, m).

ES-MS (m/z): 446 ($^{37}$ClM+H)$^+$, 444 ($^{35}$ClM+H)$^+$.

Example 111

2-phenyl-N-[5-(4-pyridyl)-1,3,4-thiadiazol-2-yl]-6-trifluoromethoxy-4-quinolinecarboxamide (compound Ib-8)

$^1$H-NMR (DMSO-d$_6$) δ: 8.78 (2H, d, J=6.3 Hz), 8.73 (1H, s), 8.41 (2H, d, J=7.9 Hz), 8.36-8.33 (2H, m), 8.03 (2H, dd, J=6.3 Hz, 1.1 Hz), 7.90 (1H, d, J=7.4 Hz), 7.65-7.59 (3H, m).

ES-MS (m/z): 494 (M+H)$^+$.

Example 112

6-chloro-N-[5-(2-furyl)-1,3,4-thiadiazol-2-yl]-2-phenyl-4-quinolinecarboxamide (compound Ib-9)

Example 113

N-[5-(2-furyl)-1,3,4-thiadiazol-2-yl]-2-phenyl-6-trifluoromethoxy-4-quinolinecarboxamide (compound Ib-10)

The following compounds Ic-1 and Ic-2 were synthesized according to the method of Production Example 1 using corresponding commercially available amine instead of 2-amino-5-(2-furyl)-1,3,4-oxadiazole.

Production Example 34

2-phenyl-N-(1,3,4-triazol-2-yl)-4-quinolinecarboxamide (compound Ic-1)

$^1$H-NMR (DMSO-d$_6$) δ: 8.50 (1H, s), 8.31 (2H, d, J=8.3 Hz), 8.20 (1H, d, J=8.5 Hz), 7.97 (1H, br), 7.87 (1H, m), 7.82 (1H, d, J=8.3 Hz), 7.66 (1H, m), 7.61-7.53 (4H, m).
ES-MS (m/z): 316 (M+H)$^+$.

Production Example 35

N-(5-phenyl-1,3,4-triazol-2-ylmethyl)-2-phenyl-4-quinolinecarboxamide (compound Ic-2)

$^1$H-NMR (CDCl$_3$) δ: 8.18-8.13 (2H, m), 8.06 (2H, d, J=7.9 Hz), 7.93-7.90 (3H, m), 7.70 (1H, m), 7.50-7.35 (7H, m), 4.88 (2H, d, J=5.5 Hz).
ES-MS (m/z): 406 (M+H)$^+$.

Example 114

A tablet is prepared by a routine method using composition consisting of 10 mg of the compound (Ia-71), 70 mg of lactose, 15 mg of starch, 4 mg of polyvinyl alcohol, and 1 mg of magnesium stearate (100 mg in total).

Example 115

According to a routine method, injectable distilled water is added to composition consisting of 70 mg of the compound (Ia-53), 50 mg of purified soybean oil, 10 mg of egg yolk lecithin, and 25 mg of glycerin, so that the total volume is 100 mL, and the mixture is charged into a vial and then sterilized by heating to prepare an injection.

Reference Example 1

Synthesis of 2-amino-5-(3-furyl)-1,3,4-oxadiazole

Thionyl chloride (3 mL) was added to a dichloromethane (10 mL) solution of 3-furancarboxylic acid (2.50 g, 22.3 mmol) under ice cooling, and the mixture was heated to reflux for 2 hours. The solvent was distilled off. After that, the residue was concentrated by the addition of toluene and added to a THF (50 mL) solution of thiosemicarbazide (4.47 g, 49.1 mmol) under ice cooling, and the mixture was stirred overnight at room temperature. To the reaction solution, a saturated aqueous solution of sodium bicarbonate was added. The mixture was subjected to extraction with ethyl acetate and dried over anhydrous sodium sulfate, and then, the solvent was distilled off to obtain 1-(3-furoyl)thiosemicarbazide (3.03 g, 16.4 mmol) (yield: 74%).

An isopropanol (15 mL) solution of 1-(3-furoyl)thiosemicarbazide (1.50 g, 8.10 mmol), a 4 mol/L aqueous sodium hydroxide solution (3.04 mL, 12.2 mmol), and 1,3-dibromo-5,5-dimethylhydantoin (1.74 g, 6.09 mmol) were added to an aqueous (3 mL) solution of potassium iodide (403 mg, 2.43 mmol) under ice cooling, and the mixture was stirred at room temperature for 2 hours. To the reaction solution, a saturated aqueous solution of sodium bisulfite and a saturated aqueous solution of sodium chloride were added. The mixture was subjected to extraction with ethyl acetate and dried over anhydrous sodium sulfate, and then, the solvent was distilled off. The obtained residue was washed with water to obtain the title compound (686 mg, 4.54 mmol) (yield: 56%).
$^1$H-NMR (CDCl$_3$+DMSO-d$_6$) δ: 7.92 (1H, s), 7.52 (1H, d, J=1.8 Hz), 6.82 (1H, d, J=1.8 Hz), 6.07 (2H, brs).
ES-MS (m/z): 152 (M+H)$^+$.

Reference Example 2

Synthesis of 2-bromo-4-quinolinecarboxylic acid

Phosphorus oxybromide (5.00 g, 17.4 mmol) was added to commercially available 2-hydroxy-4-quinolinecarboxylic acid (1.00 g, 5.29 mmol), and the mixture was heated with stirring at 90° C. for 4 hours. The reaction solution was added to ice water. To the mixture, sodium chloride was added, and the deposited crystal was collected by filtration, washed with water, and dried to obtain the title compound.

Reference Example 3

Synthesis of 2-chloro-4-quinolinecarboxylic acid methyl ester

Potassium carbonate (5.55 g, 40.2 mmol) and methyl iodide (1.88 mL, 30.2 mmol) were added to a DMF (25 mL) solution of commercially available 2-chloro-4-quinolinecarboxylic acid (4.17 g, 20.1 mmol), and the mixture was stirred overnight at room temperature in an argon atmosphere. The reaction solution was added to a saturated aqueous solution of sodium chloride, and the deposited crystal was collected by filtration, washed with water, and dried to obtain the title compound (3.53 g, 15.9 mmol) as a pale yellow solid.
ES-MS (m/z): 224 ($^{37}$ClM+H)$^+$, 222 ($^{35}$ClM+H)$^+$.

Reference Example 4

Synthesis of 2-chloro-4-quinolinecarboxylic acid benzyl ester

The title compound was obtained according to the method of Reference Example 3 using benzyl bromide instead of methyl iodide.
ES-MS (m/z): 300 ($^{37}$ClM+H)$^+$, 298 ($^{35}$ClM+H)$^+$.

Reference Example 5

Synthesis of 2-(4-nitrophenyl)-4-quinolinecarboxylic acid (1) PdCl$_2$(dppf).CH$_2$Cl$_2$ (184 mg, 0.23 mmol), tripotassium phosphate (624 mg, 4.51 mmol), and 4-nitrophenylboronic acid (958 mg, 4.51 mmol) were added to a 1,4-dioxane (5 mL)/DMF (1 mL) mixed solution of 2-chloro-4-quinolinecarboxylic acid methyl ester (500 mg, 2.26 mmol) obtained in Reference Example 3, and the mixture was heated with stirring overnight at 85° C. in an argon atmosphere. After the reaction solution was concentrated, to the residue, a saturated aqueous solution of sodium chloride and methylene chloride were added, and insoluble matter was filtered off through celite. After that, the residue was subjected to extraction with methylene chloride and dried over anhydrous sodium sulfate. The solvent was distilled off, and the obtained residue was purified by silica gel column chromatography to obtain 2-(4-nitrophenyl)-4-quinolinecarboxylic acid methyl ester (549 mg, 1.78 mmol).

ES-MS (m/z): 309 (M+H)$^+$.

(2) 2-(4-nitrophenyl)-4-quinolinecarboxylic acid methyl ester obtained above was hydrolyzed with an aqueous sodium hydroxide solution to obtain the title compound.

ES-MS (m/z): 295 (M+H)$^+$.

Reference Example 6

Synthesis of 2-(4-acetylphenyl)-4-quinolinecarboxylic acid (1) PdCl$_2$(dppf).CH$_2$Cl$_2$ (138 mg, 0.17 mmol), tripotassium phosphate (715 mg, 3.37 mmol), and 4-acetylphenylboronic acid (414 mg, 2.52 mmol) were added to a 1,4-dioxane (5 mL)/DMF (1 mL) mixed solution of 2-chloro-4-quinolinecarboxylic acid benzyl ester (500 mg, 1.68 mmol) obtained in Reference Example 4, and the mixture was heated with stirring at 85° C. for 10 hours in an argon atmosphere. After the reaction solution was concentrated, to the residue, a saturated aqueous solution of sodium chloride and methylene chloride were added, and insoluble matter was filtered off through celite. After that, the residue was subjected to extraction with methylene chloride and dried over anhydrous sodium sulfate. The solvent was distilled off, and the obtained residue was purified by silica gel column chromatography to obtain 2-(4-acetylphenyl)-4-quinolinecarboxylic acid benzyl ester (434 mg, 1.14 mmol).

ES-MS (m/z): 382 (M+H)$^+$.

(2) 2-(4-acetylphenyl)-4-quinolinecarboxylic acid benzyl ester obtained above was hydrogenated using palladium-carbon to obtain the title compound.

ES-MS (m/z): 292 (M+H)$^+$.

Reference Example 7

Synthesis of 2-(2-nitrophenyl)-4-quinolinecarboxylic acid

The title compound was obtained according to the method of Reference Example 5 using 2-nitrophenylboronic acid instead of 4-nitrophenylboronic acid.

ES-MS (m/z): 295 (M+H)$^+$.

Reference Example 8

Synthesis of 2-(3-cyanophenyl)-4-quinolinecarboxylic acid

The title compound was obtained according to the method of Reference Example 5 using 3-cyanophenylboronic acid instead of 4-nitrophenylboronic acid.

ES-MS (m/z): 275 (M+H)$^+$.

Reference Example 9

Synthesis of 2-(3-tert-butoxycarbonylphenyl)-4-quinolinecarboxylic acid

The title compound was obtained according to the method of Reference Example 5 using 3-tert-butoxycarbonylphenylboronic acid instead of 4-nitrophenylboronic acid.

ES-MS (m/z): 350 (M+H)$^+$.

Reference Example 10

Synthesis of 2-(4-cyanophenyl)-4-quinolinecarboxylic acid

The title compound was obtained according to the method of Reference Example 5 using corresponding 4-cyanophenylboronic acid instead of 4-nitrophenylboronic acid.

ES-MS (m/z): 275 (M+H)$^+$.

Reference Example 11

Synthesis of 2-(4-tert-butoxycarbonylphenyl)-4-quinolinecarboxylic acid

The title compound was obtained according to the method of Reference Example 5 using 4-tert-butoxycarbonylphenylboronic acid instead of 4-nitrophenylboronic acid.

ES-MS (m/z): 350 (M+H)$^+$.

Reference Example 12

Synthesis of 2-(4-sulfamoylphenyl)-4-quinolinecarboxylic acid

The title compound was obtained according to the method of Reference Example 5 using 4-sulfamoylphenylboronic acid pinacol ester instead of 4-nitrophenylboronic acid.

ES-MS (m/z): 329 (M+H)$^+$.

Reference Example 13

Synthesis of 2-(4-methylthiophenyl)-4-quinolinecarboxylic acid (1) 2-(4-methylthiophenyl)-4-quinolinecarboxylic acid methyl ester was obtained according to the method of Reference Example 5 (1) using 4-methylthiophenylboronic acid instead of 4-nitrophenylboronic acid.

ES-MS (m/z): 310 (M+H)$^+$.

(2) 2-(4-methylthiophenyl)-4-quinolinecarboxylic acid methyl ester obtained above was hydrolyzed with an aqueous sodium hydroxide solution to obtain the title compound.

ES-MS (m/z): 296 (M+H)$^+$.

Reference Example 14

Synthesis of 2-(2-acetoxyphenyl)-4-quinolinecarboxylic acid (1) 2-(2-hydroxyphenyl)-4-quinolinecarboxylic acid benzyl ester was obtained according to the method of Reference Example 6 (1) using 2-hydroxyphenylboronic acid instead of 4-acetylphenylboronic acid.

ES-MS (m/z): 356 (M+H)$^+$.

(2) Acetic anhydride (1 mL) was added to a pyridine (10 mL)) solution of 2-(2-hydroxyphenyl)-4-quinolinecarboxylic acid benzyl ester (1.09 g, 3.07 mmol) obtained above, and the mixture was stirred at room temperature for 7 hours. The reaction solution was concentrated, and then, the residue was purified by silica gel column chromatography to obtain 2-(2-acetoxyphenyl)-4-quinolinecarboxylic acid benzyl ester (940 mg, 2.34 mmol).

ES-MS (m/z): 398 (M+H)$^+$.

(3) A suspension of 50% hydrated 10% palladium-carbon (180 mg) in water (1 mL) was added to a methanol (10 mL) solution of 2-(2-acetoxyphenyl)-4-quinolinecarboxylic acid benzyl ester (940 mg, 2.34 mmol) obtained above, and the mixture was stirred for 7 hours in a hydrogen atmosphere. The catalyst was filtered off through celite, and then, the solvent was distilled off to obtain the title compound (610 mg, 1.99 mmol).

ES-MS (m/z): 308 (M+H)$^+$.

Reference Example 15

Synthesis of 2-(4-acetoxyphenyl)-4-quinolinecarboxylic acid

The title compound was obtained according to the method of Reference Example 14 using 4-hydroxyphenylboronic acid instead of 2-hydroxyphenylboronic acid.

ES-MS (m/z): 308 (M+H)$^+$.

Reference Example 16

Synthesis of 2-phenyl-6-trifluoromethoxy-4-quinolinecarboxylic acid

Commercially available 5-trifluoromethoxyisatin (5.66 g, 24.5 mmol) was added in small portions to an ethanol (75 mL) solution of potassium hydroxide (85%, 3.60 g, 54.5 mmol) under ice cooling. To the mixture, acetophenone (3.00 mL, 25.7 mmol) was further added, and then, the mixture was heated to reflux for 1 hour. After the reaction solution was concentrated, water was added to the residue, and then concentrated hydrochloric acid (4.47 mL, 53.6 mmol) was added thereto. The deposited crystal was collected by filtration, washed with water, and dried. The crude crystal was dissolved in a saturated aqueous solution of sodium bicarbonate and washed with diisopropyl ether, and then, concentrated hydrochloric acid was added until a crystal was deposited. The deposited crystal was collected by filtration, washed with water, and dried to obtain the title compound (7.06 g, 21.2 mmol) as an ocherous powder.

ES-MS (m/z): 334 (M+H)$^+$.

Reference Example 17

Synthesis of 6-fluoro-2-phenyl-4-quinolinecarboxylic acid

The title compound was obtained according to the method of Reference Example 16 using 5-fluoroisatin instead of 5-trifluoromethoxyisatin.

FAB-MS (m/z): 268 (M+H)$^+$.

Reference Example 18

Synthesis of 6-iodo-2-phenyl-4-quinolinecarboxylic acid

The title compound was obtained according to the method of Reference Example 16 using 5-iodoisatin instead of 5-trifluoromethoxyisatin.

ES-MS (m/z): 376 (M+H)$^+$.

Reference Example 19

Synthesis of 7-chloro-2-phenyl-4-quinolinecarboxylic acid

The title compound was obtained according to the method of Reference Example 16 using 6-chloroisatin instead of 5-trifluoromethoxyisatin.

FAB-MS (m/z): 284 (M+H)$^+$.

Reference Example 20

Synthesis of 7-bromo-2-phenyl-4-quinolinecarboxylic acid

The title compound was obtained according to the method of Reference Example 16 using 6-bromoisatin instead of 5-trifluoromethoxyisatin.

FAB-MS (m/z): 284 (M+H)$^+$.

Reference Example 21

Synthesis of 6-acetoxy-2-phenyl-4-quinolinecarboxylic acid (1) Indium chloride (0.4977 g, 2.25 mmol) and ethyl pyruvate (1.3064 g, 11.3 mmol) were added to an acetonitrile (15.0 mL) solution of 4-benzylideneaminophenol (0.8875 g, 4.50 mmol), and the mixture was heated with stirring at 90° C. for 27 minutes with microwave irradiation. To the reaction solution, water and saturated saline were added. The mixture was subjected to extraction with dichloromethane and dried over anhydrous sodium sulfate, and then, the solvent was distilled off. The obtained residue was purified by silica gel column chromatography, and the solvent was distilled off to obtain 6-hydroxy-2-phenyl-4-quinolinecarboxylic acid ethyl ester (0.264 g, 0.900 mmol) as a pale yellow powder.

ES-MS (m/z): 294 (M+H)$^+$.

(2) An aqueous sodium hydroxide solution (0.3184 g/30.0 mL) was added to a tetrahydrofuran (30.0 mL) solution of 6-hydroxy-2-phenyl-4-quinolinecarboxylic acid ethyl ester (1.1120 g, 3.79 mmol) obtained above, and the mixture was stirred at room temperature for 3 hours. To the reaction solution, dichloromethane (30.0 mL) and acetic anhydride (2.0 mL) were added. The mixture was washed with water and saturated saline and dried over anhydrous sodium sulfate, and then, the solvent was distilled off. The obtained residue was purified by silica gel column chromatography to obtain the title compound (1.0903 mg, 3.55 mmol) as a pale yellow powder.

ES-MS (m/z): 308 (M+H)$^+$.

Reference Example 22

Synthesis of 6-cyano-2-phenyl-4-quinolinecarboxylic acid (1) Zinc cyanide (0.3394 g, 2.89 mmol) and tetrakis(triphenylphosphine)palladium (0.1647 g, 0.143 mmol) were added to a dimethylformamide (14.0 mL) solution of 6-bromo-2-phenyl-4-quinolinecarboxylic acid methyl ester (0.9749 g, 2.85 mmol), and the mixture was heated with stirring at 150° C. for 10 minutes with microwave irradiation. To the reaction solution, water and a saturated aqueous solution of sodium chloride were added. The mixture was subjected to extraction with ethyl acetate and dried over anhydrous sodium sulfate, and then, the solvent was distilled off. The obtained residue was purified by silica gel column chromatography, and the solvent was distilled off to obtain 6-cyano-2-phenyl-4-quinolinecarboxylic acid methyl ester (0.6614 g, 2.29 mmol) as a pale yellow powder.

ES-MS (m/z): 289 (M+H)$^+$.

(2) An aqueous sodium hydroxide solution was added to a tetrahydrofuran (20.0 mL) solution of 6-cyano-2-phenyl-4-quinolinecarboxylic acid methyl ester (0.6354 g, 2.20 mmol) obtained above, and the mixture was stirred at room temperature for 3 hours. To the reaction solution, dichloromethane was added. The mixture was neutralized with 1 N hydrochloric acid, and then washed with water and saturated saline, and dried over anhydrous sodium sulfate. After that, the solvent was distilled off. The obtained residue was purified by silica gel column chromatography to obtain the title compound (0.5852 g, 2.13 mmol) as a pale yellow powder.

ES-MS (m/z): 275 (M+H)$^+$.

Reference Example 23

Synthesis of 6-nitro-2-phenyl-4-quinolinecarboxylic acid

The title compound was obtained according to the method of Reference Example 16 using 5-nitroisatin instead of 5-trifluoromethoxyisatin.

FAB-MS (m/z): 295 (M+H)$^+$.

Reference Example 24

Synthesis of 6-amino-2-phenylquinoline-4-carboxylic acid 6-nitro-2-phenyl-4-quinolinecarboxylic acid obtained in Reference Example 23 was reduced with tin chloride/hydrochloric acid by a routine method to obtain the title compound.

FAB-MS (m/z): 265 (M+H)$^+$.

Reference Example 25

Synthesis of 6-acetylamino-2-phenyl-4-quinolinecarboxylic acid

The title compound was obtained according to the method of Reference Example 26 using acetyl chloride instead of propionyl chloride.

FAB-MS (m/z): 307 (M+H)$^+$.

Reference Example 26

Synthesis of 2-phenyl-6-propionylamino-4-quinolinecarboxylic acid 6-amino-2-phenylquinoline-4-carboxylic acid (378 mg, 1.4 mmol) was suspended in pyridine (0.2 mL) and anhydrous THF (25 mL), and propionyl chloride (370 mg, 4 mmol) was added dropwise to the suspension with vigorous stirring. After reflux for 1.5 hours, the reaction solution was concentrated to approximately 10 mL. To the residue, ethyl acetate was added, and the deposited precipitate was collected by filtration and washed with water and ethyl ether. The crystal was recrystallized from glacial acetic acid to obtain the title compound (362 mg, 1.13 mmol) as a yellow powder.

FAB-MS (m/z): 321 (M+H)$^+$.

Reference Example 27

Synthesis of 6-butyrylamino-2-phenyl-4-quinolinecarboxylic acid

The title compound was obtained according to the method of Reference Example 26 using butyryl chloride instead of propionyl chloride.

FAB-MS (m/z): 335 (M+H)$^+$.

Reference Example 28

Synthesis of 4-(2-phenyl-6-trifluoromethoxy-4-quinolinecarbonyl)-1-(2-thiophenecarbonyl)thiosemicarbazide Oxalyl chloride (129 µL, 1.50 mmol) and methylene chloride (3 mL) were added to a methylene chloride (2 mL) solution of 2-phenyl-6-trifluoromethoxy-4-quinolinecarboxylic acid (100 mg, 0.30 mmol) described in Reference Example 16, and the mixture was stirred at room temperature for 1 hour. After that, oxalyl chloride (129 µL, 1.50 mmol) was added, and the mixture was further stirred for 2 hours. The reaction solution was concentrated, and the residue was dissolved in anhydrous acetonitrile (1 mL). To the solution, potassium thiocyanate (146 mg, 1.50 mmol) was added, and the mixture was stirred at room temperature for 1 hour. To the reaction solution, commercially available 2-thiophenecarbohydrazide (64 mg, 0.45 mmol) was added, and the mixture was stirred overnight at room temperature. To the reaction solution, methanol was added, and the mixture was concentrated. To the residue, a saturated aqueous solution of sodium chloride was added, and the deposited crystal was collected by filtration, washed with water, dried, and then purified by silica gel column chromatography to obtain the title compound (71 mg, 0.14 mmol).

ES-MS (m/z): 517 (M+H)$^+$.

Reference Example 29

Synthesis of 1-(3-methyl-2-furoyl)-4-(2-phenyl-4-quinolinecarbonyl)thiosemicarbazide (1) 3-methylfuran-2-carbohydrazide was obtained according to the method of Reference Example 30 (1) described later by using 3-methylfuran-2-carbonyl chloride and benzyl carbazate instead of 5-methylfuran-2-carbonyl chloride and tert-butyl carbazate and performing hydrogenation instead of treatment with trifluoroacetic acid.

(2) From 3-methylfuran-2-carbohydrazide obtained above, the title compound was obtained according to the method of Reference Example 30 (2) described later.

ES-MS (m/z): 431 (M+H)$^+$.

Reference Example 30

Synthesis of 1-(5-methyl-2-furoyl)-4-(2-phenyl-4-quinolinecarbonyl)thiosemicarbazide (1) Tert-butyl carbazate (549 mg, 4.15 mmol) was added to a methylene chloride (10 mL) solution of commercially available 5-methylfuran-2-carbonyl chloride (500 mg, 3.46 mmol) under ice cooling, and the mixture was stirred at room temperature for 1 hour. The reaction solution was concentrated, and then, the residue was dissolved in methylene chloride (10 mL). To the solution, trifluoroacetic acid (2 mL) was added, and the mixture was stirred at room temperature for 1.5 hours. The reaction solution was concentrated to obtain 5-methylfuran-2-carbohydrazide.

ES-MS (m/z): 141 (M+H)$^+$.

(2) 2-phenyl-4-quinolinecarbonyl isothiocyanate was prepared from 2-phenyl-4-quinolinecarbonyl chloride according to Reference Example 28 and reacted with 5-methylfuran-2-carbohydrazide obtained above to obtain the title compound.

ES-MS (m/z): 431 (M+H)$^+$.

Reference Example 31

Synthesis of 1-(4,5-dimethyl-2-furoyl)-4-(2-phenyl-4-quinolinecarbonyl)thiosemicarbazide (1) Tert-butyl carbazate (350 mg, 2.65 mmol), HBTU (1.01 g, 2.66 mmol), and N,N-diisopropylethylamine (923 µL, 5.30 mmol) were added to a methylene chloride (5 mL) solution of commercially available 4,5-dimethylfurancarboxylic acid (248 mg, 1.77 mmol), and the mixture was stirred overnight at room temperature. After the reaction solution was concentrated, to the residue, a saturated aqueous solution of sodium bicarbonate was added, and the mixture was subjected to extraction with methylene chloride and dried over anhydrous sodium sulfate, and then, the solvent was distilled off. The obtained residue was dissolved in methylene chloride (6 mL). To the solution, trifluoroacetic acid (1.5 mL) was added, and the mixture was stirred at room temperature for 1.5 hours. The reaction solution was concentrated to obtain 4,5-dimethylfuran-2-carbohydrazide.

(2) 2-phenyl-4-quinolinecarbonyl isothiocyanate was prepared from 2-phenyl-4-quinolinecarbonyl chloride according to Reference Example 28 and reacted with 4,5-dimethylfuran-2-carbohydrazide obtained above to obtain the title compound.

ES-MS (m/z): 445 (M+H)$^+$.

Reference Example 32

Synthesis of 1-(2-benzofurancarbonyl)-4-(2-phenyl-4-quinolinecarbonyl)thiosemicarbazide The title compound was obtained in the same way as in Reference Example 31 using 2-benzofurancarboxylic acid instead of 4,5-dimethylfurancarboxylic acid.

ES-MS (m/z): 467 (M+H)$^+$.

Reference Example 33

Synthesis of 1-(2-methyl-4-thiazolylcarbonyl)-4-(2-phenyl-4-quinolinecarbonyl)thiosemicarbazide The title compound was obtained according to the method of Reference Example 28 using 2-phenyl-4-quinolinecarboxylic acid instead of 2-phenyl-6-(trifluoromethoxy)-4-quinolinecarboxylic acid and commercially available 2-methyl-4-thiazolecarbohydrazide instead of 2-thiophenecarbohydrazide.

ES-MS (m/z): 448 (M+H)$^+$.

Reference Example 34

Synthesis of 1-(2,4-dimethyl-5-thiazolylcarbonyl)-4-(2-phenyl-4-quinolinecarbonyl)thiosemicarbazide The title compound was obtained in the same way as in Reference Example 28 using 2-phenyl-4-quinolinecarboxylic acid instead of 2-phenyl-6-(trifluoromethoxy)-4-quinolinecarboxylic acid and commercially available 2,4-dimethyl-5-thiazolecarbohydrazide instead of 2-thiophenecarbohydrazide.

ES-MS (m/z): 462 (M+H)$^+$.

Reference Example 35

Synthesis of 1-(3-methoxybenzoyl)-4-(2-phenyl-4-quinolinecarbonyl)thiosemicarbazide The title compound was obtained according to the method of Reference Example 28 using 2-phenyl-4-quinolinecarboxylic acid instead of 2-phenyl-6-(trifluoromethoxy)-4-quinolinecarboxylic acid and commercially available 3-methoxybenzoylhydrazide instead of 2-thiophenecarbohydrazide.

ES-MS (m/z): 457 (M+H)$^+$.

Reference Example 36

Synthesis of 1-cyanomethylcarbonyl-4-(2-phenyl-4-quinolinecarbonyl)thiosemicarbazide The title compound was obtained according to the method of Reference Example 28 using 2-phenyl-4-quinolinecarboxylic acid instead of 2-phenyl-6-(trifluoromethoxy)-4-quinolinecarboxylic acid and commercially available cyanoacetylhydrazide instead of 2-thiophenecarbohydrazide.

ES-MS (m/z): 390 (M+H)$^+$.

Reference Example 37

Synthesis of 4-(6-chloro-2-phenyl-4-quinolinecarbonyl)-1-(2-thiophenecarbonyl)thiosemicarbazide The title compound was obtained according to the method of Reference Example 28 using 6-chloro-2-phenyl-4-quinolinecarboxylic acid instead of 2-phenyl-6-(trifluoromethoxy)-4-quinolinecarboxylic acid.

ES-MS (m/z): 468 ($^{37}$ClM+H)$^+$, 466 ($^{35}$ClM+H)$^+$.

Reference Example 38

Synthesis of 4-(2-phenyl-4-quinolinecarbonyl)-1-(2-tetrahydrofurancarbonyl)thiosemicarbazide The title compound was obtained in the same way as in Reference Example 29 using 2-tetrahydrofurancarboxylic acid instead of 3-methylfurancarboxylic acid.

ES-MS (m/z): 421 (M+H)$^+$.

INDUSTRIAL APPLICABILITY

A quinolinecarboxamide derivative of the present invention having STAT3 inhibitory activity can be used as an anti-cancer agent or the like for various cancers.

The invention claimed is:
1. A method of inhibiting a STAT3 activity, comprising administering to a subject in need thereof a STAT3 inhibitor comprising a quinolinecarboxamide derivative represented by the formula (I), as an active ingredient:

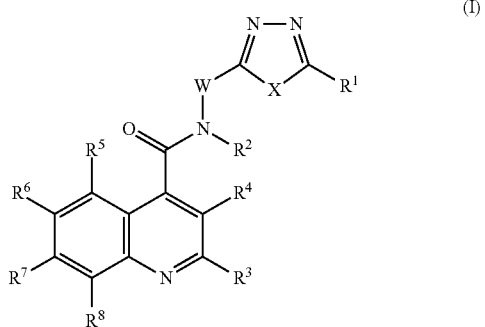

wherein $R^1$, $R^2$, $R^3$, $R^4$, $R^5$, $R^6$, $R^7$, and $R^8$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, wherein any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring;

W represents a single bond or a substituted or unsubstituted alkylene group; and X represents an oxygen atom, a sulfur atom, or $NR^{34}$ (wherein $R^{34}$ is as defined above in $R^9$), wherein when X is a sulfur group, $R^1$ is not a substituted alkyl group, or a pharmacologically acceptable salt thereof.

2. The method according to claim 1, wherein X is an oxygen atom, and the quinolinecarboxamide derivative is represented by the formula (Ia):

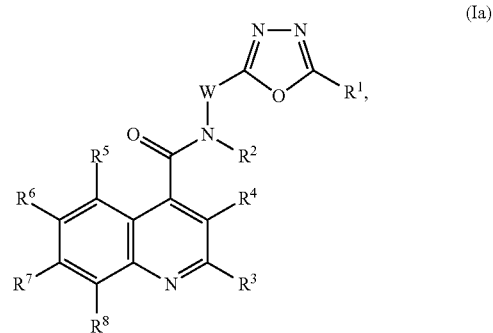

or a pharmacologically acceptable salt thereof.

3. The method according to claim 2, wherein W in the quinolinecarboxamide derivative of the formula (Ia) is a single bond,
or a pharmacologically acceptable salt thereof.

4. The method according to claim 3, wherein $R^1$ and $R^3$ in the quinolinecarboxamide derivative of the formula (Ia) are the same or different and each are a substituted or unsubstituted aryl group, a substituted or unsubstituted aromatic heterocyclic group, a styryl group, or an alkoxy group,
or a pharmacologically acceptable salt thereof.

5. The method according to claim 4, wherein the aryl group is present in the quinolinecarboxamide derivative of the formula (Ia) and is a phenyl group or a naphthyl group,
or a pharmacologically acceptable salt thereof.

6. The method according to claim 4, wherein the aromatic heterocyclic group is present in the quinolinecarboxamide derivative of the formula (Ia) and is a furyl group or a thienyl group, or a pharmacologically acceptable salt thereof.

7. The method according to claim 4, wherein $R^1$ in the quinolinecarboxamide derivative of the formula (Ia) is a furyl group, and $R^3$ is a substituted or unsubstituted phenyl group, a substituted or unsubstituted naphthyl group, a substituted or unsubstituted furyl group, a substituted or unsubstituted thienyl group, or a styryl group, or a pharmacologically acceptable salt thereof.

8. The method according to claim 7, wherein $R^6$ in the quinolinecarboxamide derivative of the formula (Ia) is a fluorine atom, a chlorine atom, a bromine atom, a methyl group, a phenyl group, a hydroxyphenyl group, a thienyl group, a pyridyl group, a methoxy group, or a trifluoromethoxy group, or a pharmacologically acceptable salt thereof.

9. The method according to claim 4 or 5, wherein $R^1$ in the quinolinecarboxamide derivative of the formula (Ia) is a substituted or unsubstituted phenyl group, and $R^3$ is a phenyl group, or a pharmacologically acceptable salt thereof.

10. The method according to claim 9, wherein $R^6$ in the quinolinecarboxamide derivative of the formula (Ia) is a chlorine atom or a trifluoromethoxy group, or a pharmacologically acceptable salt thereof.

11. The method according to claim 2, wherein $R^2$ in the quinolinecarboxamide derivative of the formula (Ia) is a hydrogen atom, or a pharmacologically acceptable salt thereof.

12. The method according to claim 1, wherein X is a sulfur atom, and the quinolinecarboxamide derivative is represented by the formula (Ib):

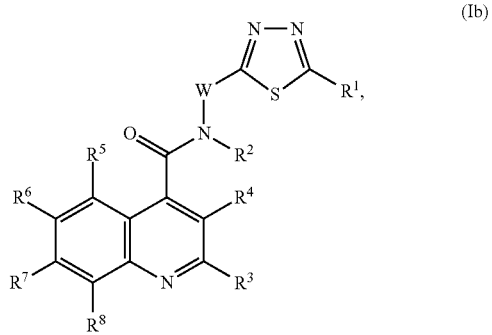

(Ib)

or a pharmacologically acceptable salt thereof.

13. The method according to claim 12, wherein W in the quinolinecarboxamide derivative of the formula (Ib) is a single bond, or a pharmacologically acceptable salt thereof.

14. The method according to claim 13, wherein $R^1$ and $R^3$ in the quinolinecarboxamide derivative of the formula (Ib) are the same or different and each are a substituted or unsubstituted aryl group or a substituted or unsubstituted aromatic heterocyclic group, or a pharmacologically acceptable salt thereof.

15. The method according to claim 14, wherein $R^1$ in the quinolinecarboxamide derivative of the formula (Ib) is a pyridyl group, and $R^3$ is a substituted or unsubstituted phenyl group, a substituted or unsubstituted furyl group, a substituted or unsubstituted thienyl group, or a pyridyl group, or a pharmacologically acceptable salt thereof.

16. The method according to claim 15, wherein $R^2$ in the quinolinecarboxamide derivative of the formula (Ib) is a hydrogen atom, or a pharmacologically acceptable salt thereof.

17. A method for treating cancer comprising administering to a subject in need thereof an anticancer agent comprising a STAT3 inhibitor, wherein the STAT3 inhibitor comprises a quinolinecarboxamide derivative represented by the formula (I) or a pharmacologically acceptable salt thereof, as an active ingredient:

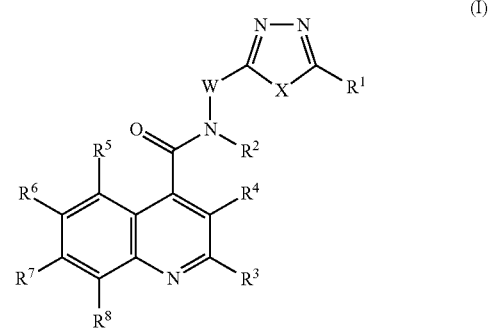

(I)

wherein $R^1$, $R^2$, $R^3$, $R^4$, $R^5$, $R^6$, $R^7$, and $R^8$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, wherein any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring;

W represents a single bond or a substituted or unsubstituted alkylene group; and X represents an oxygen atom, a sulfur atom, or $NR^{34}$ (wherein $R^{34}$ is as defined in $R^9$), wherein when X is a sulfur group, $R^1$ is not a substituted alkyl group.

18. A quinolinecarboxamide derivative, represented by the formula (I-1):

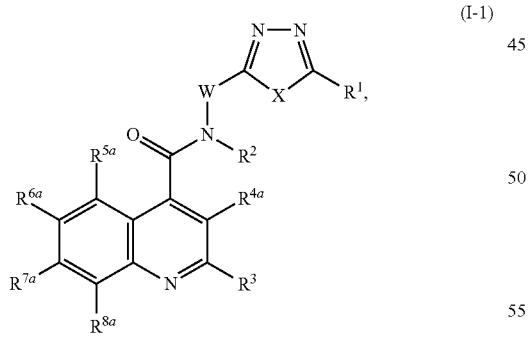

(I-1)

wherein $R^1$, $R^2$, $R^3$, $R^{5a}$, $R^{6a}$, $R^{7a}$ and $R^{8a}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group), $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, and any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring, $R^{4a}$ is a hydrogen atom, an unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group), $OR^{14}$ (wherein $R^{14}$ is as defined above in $R^9$), $OCOR^{15}$ (wherein $R^{15}$ is as defined above in $R^9$), $S(O)mR^{16}$ (wherein in represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, and any two adjacent s of $R^3$ to $R^8$ may be linked together to form a substituted or unsubstituted alicyclic hydrocarbon ring, alicyclic heterocyclic ring, aromatic hydrocarbon ring, or aromatic heterocyclic ring, wherein at least one group of $R^{4a}$, $R^{5a}$, $R^{6a}$, $R^{7a}$, and $R^{8a}$ represents a group other than a hydrogen atom;

W represents a single bond or a substituted or unsubstituted alkylene group; and X represents an oxygen atom, a sulfur atom, or $NR^{34}$ (wherein $R^{34}$ is as defined above in $R^9$), or a pharmacologically acceptable salt thereof.

19. The quinolinecarboxamide derivative according to claim 18, represented by the formula (I-1a):

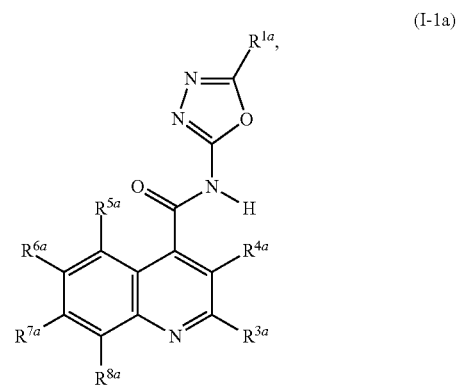

(I-1a)

wherein $R^{1a}$ and $R^{3a}$ are the same or different and each represent a substituted or unsubstituted aryl group or a substituted or unsubstituted aromatic heterocyclic group, or a pharmacologically acceptable salt thereof.

20. The quinolinecarboxamide derivative according to claim 19, wherein in $R^{1a}$ and $R^{3a}$, the aryl group is present and is a phenyl group, and/or the aromatic heterocyclic group is present and is a furyl group or a thienyl group, or a pharmacologically acceptable salt thereof.

21. The quinolinecarboxamide derivative according to claim 19 or 20, wherein $R^{1a}$ is a furyl group, and $R^{3a}$ is a substituted or unsubstituted phenyl group, a furyl group, or a thienyl group, or a pharmacologically acceptable salt thereof.

22. The quinolinecarboxamide derivative according to claim 19, wherein at least one group of $R^{4a}$, $R^{5a}$, $R^{6a}$, $R^{7a}$, and $R^{8a}$ is a fluorine atom, a chlorine atom, a bromine atom, a methyl group, a phenyl group, a hydroxyphenyl group, a thienyl group, a pyridyl group, a methoxy group, or a trifluoromethoxy group, or a pharmacologically acceptable salt thereof.

23. The quinolinecarboxamide derivative according to claim 19 or 20, wherein $R^{1a}$ is a substituted or unsubstituted phenyl group, and $R^{3a}$ is a phenyl group, or a pharmacologically acceptable salt thereof.

24. The quinolinecarboxamide derivative according to claim 19, wherein $R^{6a}$ is a chlorine atom or a trifluoromethoxy group, or a pharmacologically acceptable salt thereof.

25. A quinolinecarboxamide derivative represented by the formula (I-2):

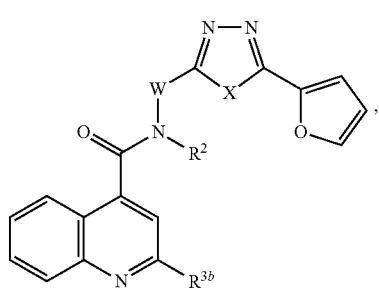

wherein $R^{3b}$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group other than a phenyl group, a substituted or unsubstituted aralkyl group, a substituted or unsubstituted aromatic heterocyclic group other than 2-thienyl, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group), $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom;

$R^2$ is a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in R⁹), or a group which is formed by linking R¹⁹ and R²⁰ together represents a nitrogen-containing heterocyclic group), N(R²⁴)C(=Q₂)NR²⁵R²⁶ (wherein Q² represents an oxygen atom, a sulfur atom, NR²⁷ (wherein R²⁷ is as defined above in R⁹), NCN, CHNO₂, or C(CN)₂, R²⁴ is as defined above in R⁹, and R²⁵ and R²⁶ are the same or different and are as defined above in R¹¹ and R¹², respectively), N(R²⁸)SO₂NR²⁹R³⁰ (wherein R²⁸ is as defined above in R⁹, and R²⁹ and R³⁰ are the same or different and are as defined above in R¹¹ and R¹², respectively), SiR³¹R³²R³³ (wherein R³¹, R³², and R³³ are the same or different and are each as defined above in R⁹), a nitro group, a cyano group, or a halogen atom, wherein any two adjacent groups of R³ to R⁸ may be linked together to form a substituted or unsubstituted alicyclic hydrocarbon ring, alicyclic heterocyclic ring, aromatic hydrocarbon ring, or aromatic heterocyclic ring;

W represents a single bond or a substituted or unsubstituted alkylene group; and X represents an oxygen atom, a sulfur atom, or NR³⁴ (wherein R³⁴ is as defined above in R⁹), or a pharmacologically acceptable salt thereof.

26. The quinolinecarboxamide derivative according to claim 25, represented by the formula (I-2a):

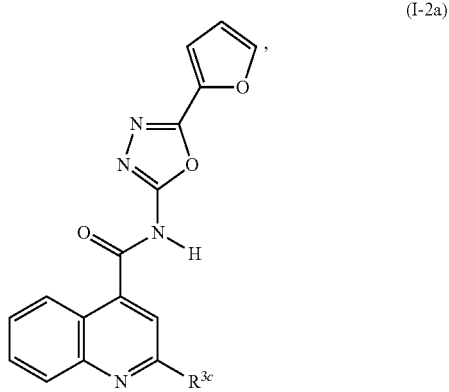

(I-2a)

wherein R³ᶜ represents a substituted phenyl group, a substituted or unsubstituted naphthyl group, a substituted or unsubstituted furyl group, a substituted thienyl group, a styryl group, or an alkoxy group, or a pharmacologically acceptable salt thereof.

27. A method of inhibiting a STAT3 activity, comprising administering to a subject in need thereof a STAT3 inhibitor comprising a quinolinecarboxamide derivative represented by the formula (I-1), as an active ingredient:

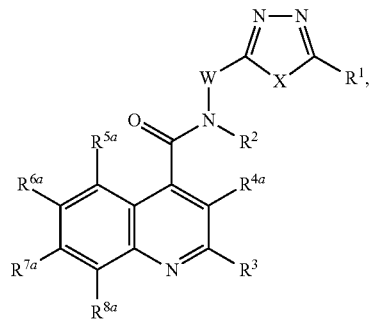

(I-1)

wherein

R¹, R², R³, R⁵ᵃ, R⁶ᵃ, R⁷ᵃ, and R⁸ᵃ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR⁹ (wherein R⁹ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR¹⁰ (wherein R¹⁰ is as defined above in R⁹), C(=Q¹)NR¹¹R¹² (wherein Q¹ represents an oxygen atom, a sulfur atom, or NR¹³ (wherein R¹³ is as defined above in R⁹), and R¹¹ and R¹² are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking R¹¹ and R¹² together represents a nitrogen-containing heterocyclic group), OR¹⁴ (wherein R¹⁴ is as defined above in R⁹), OCOR¹⁵ (wherein R¹⁵ is as defined above in R⁹), S(O)mR¹⁶ (wherein m represents 0, 1, or 2, and R¹⁶ is as defined above in R⁹), SO₂NR¹⁷R¹⁸ (wherein R¹⁷ and R¹⁸ are the same or different and are as defined above in R¹¹ and R¹², respectively), NR¹⁹R²⁰ (wherein R¹⁹ and R²⁰ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR²¹ (wherein R²¹ is as defined above in R⁹), COOR²² (wherein R²² is as defined above in R⁹), or SO₂R²³ (wherein R²³ is as defined above in R⁹), or a group which is formed by linking R¹⁹ and R²⁰ together represents a nitrogen-containing heterocyclic group), N(R²⁴)C(=Q²)NR²⁵R²⁶ (wherein Q² represents an oxygen atom, a sulfur atom, NR²⁷ (wherein R²⁷ is as defined above in R⁹), NCN, CHNO₂, or C(CN)₂, R²⁴ is as defined above in R⁹, and R²⁵ and R²⁶ are the same or different and are as defined above in R¹¹ and R¹², respectively), N(R²⁸)SO₂NR²⁹R³⁰ (wherein R²⁸ is as defined above in R⁹, and R²⁹ and R³⁰ are the same or different and are as defined above in R¹¹ and R¹², respectively), SiR³¹R³²R³³ (wherein R³¹, R³², and R³³ are the same or different and are each as defined above in R⁹), a nitro group, a cyano group, or a halogen atom, and any two adjacent groups of R³ to R⁸ may be linked together to form a substituted or unsubstituted alicyclic hydrocarbon ring, alicyclic heterocyclic ring, aromatic hydrocarbon ring, or aromatic heterocyclic ring, R⁴ᵃ is a hydrogen atom, an unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR⁹ (wherein R⁹ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR¹⁰ (wherein R¹⁰ is as defined above in R⁹), C(=Q¹)NR¹¹R¹² (wherein Q¹ represents an oxygen atom, a sulfur atom, or NR¹³ (wherein R¹³ is as defined above in R⁹), and R¹¹ and R¹² are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking R¹¹ and R¹² together represents a nitrogen-containing heterocyclic group), OR¹⁴ (wherein R¹⁴ is as defined above in R⁹), OCOR¹⁵ (wherein R¹⁵ is as defined above in R⁹), S(O)ₘR¹⁶ (wherein m represents 0, 1, or 2, and R¹⁶ is as defined above in R⁹), SO₂NR¹⁷R¹⁸ (wherein R¹⁷ and R¹⁸ are the same or different and are as defined above in R¹¹ and R¹², respectively), NR¹⁹R²⁰ (wherein R¹⁹ and R²⁰ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR²¹ (wherein R²¹ is as defined above in R⁹), COOR²² (wherein R²² is as defined above in R⁹), or SO₂R²³ (wherein R²³ is as defined above in R⁹), or a group which is formed by linking R¹⁹ and R²⁰ together represents a nitrogen-containing heterocyclic group), N(R²⁴)C(=Q²)NR²⁵R²⁶ (wherein Q² represents an oxygen atom, a sulfur atom, NR²⁷ (wherein R²⁷ is as defined above in R⁹), NCN, CHNO₂, or C(CN)₂, R²⁴ is as defined above in R⁹, and R²⁵ and R²⁶ are the same or different and are as defined above in R¹¹ and R¹², respectively), N(R²⁸)SO₂NR²⁹R³⁰ (wherein R²⁸ is as defined above in R⁹, and R²⁹ and R³⁰ are the same or different and are as defined above in R¹¹ and R¹², respectively), SiR³¹R³²R³³ (wherein R³¹, R³², and R³³ are the same or different and are each as defined above in R⁹), a nitro group, a cyano group, or a halogen atom, and any two adjacent groups of R³ to R⁸ may be linked together to form a substituted or unsubstituted alicyclic hydrocarbon ring, alicyclic heterocyclic ring, aromatic hydrocarbon ring, or aromatic heterocyclic ring, wherein at least one group of R⁴ᵃ, R⁵ᵃ, R⁶ᵃ, R⁷ᵃ, and R⁸ᵃ represents a group other than a hydrogen atom;

W represents a single bond or a substituted or unsubstituted alkylene group; and X represents an oxygen atom, a sulfur atom, or NR³⁴ (wherein R³⁴ is as defined above in R⁹), or a pharmacologically acceptable salt thereof.

28. A method of inhibiting a STAT3 activity, comprising administering to a subject in need thereof a STAT3 inhibitor comprising a quinolinecarboxamide derivative represented by the formula (I-2), as an active ingredient:

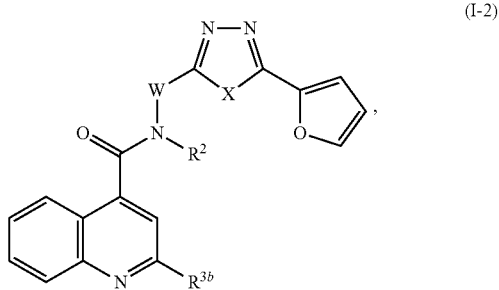

(I-2)

wherein R³ᵇ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group other than a phenyl group, a substituted or unsubstituted aralkyl group, a substituted or unsubstituted aromatic heterocyclic group other than 2-thienyl, a substituted or unsubstituted aromatic heterocyclic alkyl group, COR⁹ (wherein R⁹ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR$^{10}$ (wherein R$^{10}$ is as defined above in R$^9$), C(=Q$^1$)NR$^{11}$R$^{12}$ (wherein Q$^1$ represents an oxygen atom, a sulfur atom, or NR$^{13}$ (wherein R$^{13}$ is as defined above in R$^9$), and R$^{11}$ and R$^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking R$^{11}$ and R$^{12}$ together represents a nitrogen-containing heterocyclic group), OR$^{14}$ (wherein R$^{14}$ is as defined above in R$^9$), OCOR$^{15}$ (wherein R$^{15}$ is as defined above in R$^9$), S(O)mR$^{16}$ (wherein m represents 0, 1, or 2, and R$^{16}$ is as defined above in R$^9$), SO$_2$NR$^{17}$R$^{18}$ (wherein R$^{17}$ and R$^{18}$ are the same or different and are as defined above in R$^{11}$ and R$^{12}$, respectively), NR$^{19}$R$^{20}$ (wherein R$^{19}$ and R$^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^{21}$ (wherein R$^{21}$ is as defined above in R$^9$), COOR$^{22}$ (wherein R$^{22}$ is as defined above in R$^9$), or SO$_2$R$^{23}$ (wherein R$^{23}$ is as defined above in R$^9$), or a group which is formed by linking R$^{19}$ and R$^{20}$ together represents a nitrogen-containing heterocyclic group), N(R$^{24}$)C(=Q$^2$)NR$^{25}$R$^{26}$ (wherein Q$^2$ represents an oxygen atom, a sulfur atom, NR$^{27}$ (wherein R$^{27}$ is as defined above in R$^9$), NCN, CHNO$_2$, or C(CN)$_2$, R$^{24}$ is as defined above in R$^9$, and R$^{25}$ and R$^{26}$ are the same or different and are as defined above in R$^{11}$ and R$^{12}$, respectively), N(R$^{28}$)SO$_2$NR$^{29}$R$^{30}$ (wherein R$^{28}$ is as defined above in R$^9$, and R$^{29}$ and R$^{30}$ are the same or different and are as defined above in R$^{11}$ and R$^{12}$, respectively), SiR$^{31}$R$^{32}$R$^{33}$ (wherein R$^{31}$, R$^{32}$ and R$^{33}$ are the same or different and are each as defined above in R$^9$), a nitro group, a cyano group, or a halogen atom;

R$^2$ is a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^9$ (wherein R$^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR$^{10}$ (wherein R$^{10}$ is as defined above in R$^9$), C(=Q$^1$)NR$^{11}$R$^{12}$ (wherein Q$^1$ represents an oxygen atom, a sulfur atom, or NR$^{13}$ (wherein R$^{13}$ is as defined above in R$^9$), and R$^{11}$ and R$^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking R$^{11}$ and R$^{12}$ together represents a nitrogen-containing heterocyclic group], OR$^{14}$ (wherein R$^{14}$ is as defined above in R$^9$), OCOR$^{15}$ (wherein R$^{15}$ is as defined above in R$^9$), S(O)mR$^{16}$ (wherein m represents 0, 1, or 2, and R$^{16}$ is as defined above in R$^9$), SO$_2$NR$^{17}$R$^{18}$ (wherein R$^{17}$ and R$^{18}$ are the same or different and are as defined above in R$^{11}$ and R$^{12}$, respectively), NR$^{19}$R$^{20}$ (wherein R$^{19}$ and R$^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^{21}$ (wherein R$^{21}$ is as defined above in R$^9$), COOR$^{22}$ (wherein R$^{22}$ is as defined above in R$^9$), or SO$_2$R$^{23}$ (wherein R$^{23}$ is as defined above in R$^9$), or a group which is formed by linking R$^{19}$ and R$^{20}$ together represents a nitrogen-containing heterocyclic group), N(R$^{24}$)C(=Q$^2$)NR$^{25}$R$^{26}$ (wherein Q$^2$ represents an oxygen atom, a sulfur atom, NR$^{27}$ (wherein R$^{27}$ is as defined above in R$^9$), NCN, CHNO$_2$, or C(CN)$_2$, R$^{24}$ is as defined above in R$^9$, and R$^{25}$ and R$^{26}$ are the same or different and are as defined above in R$^{11}$ and R$^{12}$, respectively), N(R$^{28}$)SO$_2$NR$^{29}$R$^{30}$ (wherein R$^{28}$ is as defined above in R$^9$, and R$^{29}$ and R$^{30}$ are the same or different and are as defined above in R$^{11}$ and R$^{12}$, respectively), SiR$^{31}$R$^{32}$R$^{33}$ (wherein R$^{31}$, R$^{32}$, and R$^{33}$ are the same or different and are each as defined above in R$^9$), a nitro group, a cyano group, or a halogen atom, wherein any two adjacent groups of R$^3$ to R$^8$ may be linked together to form a substituted or unsubstituted alicyclic hydrocarbon ring, alicyclic heterocyclic ring, aromatic hydrocarbon ring, or aromatic heterocyclic ring;

W represents a single bond or a substituted or unsubstituted alkylene group; and X represents an oxygen atom, a sulfur atom, or NR$^{34}$ (wherein R$^{34}$ is as defined above in R$^9$), or a pharmacologically acceptable salt thereof.

29. A method for treating cancer, comprising administering to a subject in need thereof a STAT3 inhibitor comprising a quinolinecarboxamide derivative represented by the formula (I-1), as an active ingredient:

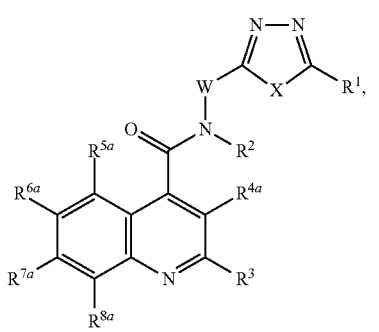

(I-1)

wherein $R^1$, $R^2$, $R^3$, $R^{5a}$, $R^{6a}$, $R^{7a}$, and $R^{8a}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group), $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, and any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring, $R^{4a}$ is a hydrogen atom, an unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^9$ (wherein $R^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{10}$ (wherein $R^{10}$ is as defined above in $R^9$), $C(=Q^1)NR^{11}R^{12}$ (wherein $Q^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group), $OR^{14}$ (wherein $R^{14}$ is as defined above in $R^9$), $OCOR^{15}$ (wherein $R^{15}$ is as defined above in $R^9$), $S(O)mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^{21}$ (wherein R$^{21}$ is as defined above in R$^9$), COOR$^{22}$ (wherein R$^{22}$ is as defined above in R$^{19}$), or SO$_2$R$^{23}$ (wherein R$^{23}$ is as defined above in R$^9$), or a group which is formed by linking R$^{19}$ and R$^{20}$ together represents a nitrogen-containing heterocyclic group), N(R$^{24}$)C(=Q$^2$)NR$^{25}$R$^{26}$ (wherein Q$^2$ represents an oxygen atom, a sulfur atom, NR$^{27}$ (wherein R$^{27}$ is as defined above in R$^9$), NCN, CHNO$_2$, or C(CN)$_2$, R$^{24}$ is as defined above in R$^9$, and R$^{25}$ and R$^{26}$ are the same or different and are as defined above in R$^{11}$ and R$^{12}$, respectively), N(R$^{28}$)SO$_2$NR$^{29}$R$^{30}$ (wherein R$^{28}$ is as defined above in R$^9$, and R$^{29}$ and R$^{30}$ are the same or different and are as defined above in R$^{11}$ and R$^{12}$, respectively), SiR$^{31}$R$^{32}$R$^{33}$ (wherein R$^{31}$, R$^{32}$, and R$^{33}$ are the same or different and are each as defined above in R$^9$), a nitro group, a cyano group, or a halogen atom, and any two adjacent groups of R$^3$ to R$^8$ may be linked together to form a substituted or unsubstituted alicyclic hydrocarbon ring, alicyclic heterocyclic ring, aromatic hydrocarbon ring, or aromatic heterocyclic ring, wherein at least one group of R$^{4a}$, R$^{5a}$, R$^{6a}$, R$^{7a}$, and R$^{8a}$ represents a group other than a hydrogen atom;

W represents a single bond or a substituted or unsubstituted alkylene group; and X represents an oxygen atom, a sulfur atom, or NR$^{34}$ (wherein R$^{34}$ is as defined above in R$^9$), or a pharmacologically acceptable salt thereof.

30. A method for treating cancer, comprising administering to a subject in need thereof a STAT3 inhibitor comprising a quinolinecarboxamide derivative represented by the formula (I-2), as an active ingredient:

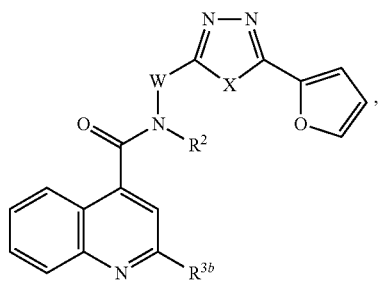

(I-2)

wherein R$^{3b}$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group other than a phenyl group, a substituted or unsubstituted aralkyl group, a substituted or unsubstituted aromatic heterocyclic group other than 2-thienyl, a substituted or unsubstituted aromatic heterocyclic alkyl group, COR$^9$ (wherein R$^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstrtuted aromatic heterocyclic alkyl group), COOR$^{10}$ (wherein R$^{10}$ is as defined above in R$^9$), C(=Q$^1$)NR$^{11}$R$^{12}$ (wherein Q$^1$ represents an oxygen atom, a sulfur atom, or NR$^{13}$ (wherein R$^{13}$ is as defined above in R$^9$), and R$^{11}$ and R$^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking R$^{11}$ and R$^{12}$ together represents a nitrogen-containing heterocyclic group), OR$^{14}$ (wherein R$^{14}$ is as defined above in R$^9$), OCOR$^{15}$ (wherein R$^{15}$ is as defined above in R$^9$), S(O)mR$^{16}$ (wherein m represents 0, 1, or 2, and R$^{16}$ is as defined above in R$^9$), SO$_2$NR$^{17}$, R$^{18}$ (wherein R$^{17}$ and R$^{18}$ are the same or different and are as defined above in R$^{11}$ and R$^{12}$, respectively), NR$^{19}$R$^{20}$ (wherein R$^{19}$ and R$^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^{21}$ (wherein R$^{21}$ is as defined above in R$^9$), COOR$^{22}$ (wherein R$^{22}$ is as defined above in R$^9$), or SO$_2$R$^{23}$ (wherein R$^{23}$ is as defined above in R$^9$), or a group which is formed by linking R$^{19}$ and R$^{20}$ together represents a nitrogen-containing heterocyclic group), N(R$^{24}$)C(=Q$^2$)NR$^{25}$R$^{26}$ (wherein Q$^2$ represents an oxygen atom, a sulfur atom, NR$^{27}$ (wherein R$^{27}$ is as defined above in R$^9$), NCN, CHNO$_2$, or C(CN)$_2$, R$^{24}$ is as defined above in R$^9$, and R$^{25}$ and R$^{26}$ are the same or different and are as defined above in R$^{11}$ and R$^{12}$, respectively), N(R$^{28}$)SO$_2$NR$^{29}$R$^{30}$ (wherein R$^{28}$ is as defined above in R$^9$, and R$^{29}$ and R$^{30}$ are the same or different and are as defined above in R$^{11}$ and R$^{12}$, respectively), SiR$^{31}$R$^{32}$R$^{33}$ (wherein R$^{31}$, R$^{32}$, and R$^{33}$ are the same or different and are each as defined above in R$^9$), a nitro group, a cyano group, or a halogen atom;

R$^2$ is a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, COR$^9$ (wherein R$^9$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group), COOR$^{10}$ (wherein R$^{10}$ is as defined above in R$^9$), C(=Q$^1$)NR$^{11}$R$^{12}$ (wherein Q$^1$ represents an oxygen atom, a sulfur atom, or $NR^{13}$ (wherein $R^{13}$ is as defined above in $R^9$), and $R^{11}$ and $R^{12}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, or a substituted or unsubstituted aromatic heterocyclic alkyl group, or a group which is formed by linking $R^{11}$ and $R^{12}$ together represents a nitrogen-containing heterocyclic group], $OR^{14}$ (wherein $R^{14}$ is as defined above in $R^9$), $OCOR^{15}$ (wherein $R^{15}$ is as defined above in $R^9$), $S(O)_mR^{16}$ (wherein m represents 0, 1, or 2, and $R^{16}$ is as defined above in $R^9$), $SO_2NR^{17}R^{18}$ (wherein $R^{17}$ and $R^{18}$ are the same or different and are as defined above in $R^{11}$ and $R^{12}$, respectively), $NR^{19}R^{20}$ (wherein $R^{19}$ and $R^{20}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{21}$ (wherein $R^{21}$ is as defined above in $R^9$), $COOR^{22}$ (wherein $R^{22}$ is as defined above in $R^9$), or $SO_2R^{23}$ (wherein $R^{23}$ is as defined above in $R^9$), or a group which is formed by linking $R^{19}$ and $R^{20}$ together represents a nitrogen-containing heterocyclic group), $N(R^{24})C(=Q^2)NR^{25}R^{26}$ (wherein $Q^2$ represents an oxygen atom, a sulfur atom, $NR^{27}$ (wherein $R^{27}$ is as defined above in $R^9$), NCN, $CHNO_2$, or $C(CN)_2$, $R^{24}$ is as defined above in $R^9$, and $R^{25}$ and $R^{26}$ are the same or different and are as defined above in $R^{11}$ and $R^{12}$, respectively), $N(R^{28})SO_2NR^{29}R^{30}$ (wherein $R^{28}$ is as defined above in $R^9$, and $R^{29}$ and $R^{30}$ are the same or different and are as defined above in $R^{11}$ and $R^{12}$, respectively), $SiR^{31}R^{32}R^{33}$ (wherein $R^{31}$, $R^{32}$, and $R^{33}$ are the same or different and are each as defined above in $R^9$), a nitro group, a cyano group, or a halogen atom, wherein any two adjacent groups of $R^3$ to $R^8$ may be linked together to form a substituted or unsubstituted alicyclic hydrocarbon ring, alicyclic heterocyclic ring, aromatic hydrocarbon ring, or aromatic heterocyclic ring;

W represents a single bond or a substituted or unsubstituted alkylene group; and X represents an oxygen atom, a sulfur atom, or $NR^{34}$ (wherein $R^{34}$ is as defined above in $R^9$), or a pharmacologically acceptable salt thereof.

* * * * *